United States Patent [19]
Funk

[11] 4,193,116
[45] Mar. 11, 1980

[54] ANALYSIS INSTRUMENT

[75] Inventor: David B. Funk, Virden, Ill.

[73] Assignee: Dickey-john Corporation, Auburn, Ill.

[21] Appl. No.: 890,502

[22] Filed: Mar. 29, 1978

Related U.S. Application Data

[63] Continuation-in-part of Ser. No. 791,641, Apr. 27, 1977, abandoned.

[51] Int. Cl.² .............................................. G01R 27/26
[52] U.S. Cl. ................................. 364/556; 324/61 R; 364/497; 364/567
[58] Field of Search ............... 364/497, 498, 526, 481, 364/567, 556; 324/61 R, 65 R

[56] References Cited

U.S. PATENT DOCUMENTS

| | | | |
|---|---|---|---|
| 3,776,642 | 12/1973 | Anson et al. | 356/188 |
| 3,794,911 | 2/1974 | Fathauer | 324/61 QS |
| 3,828,173 | 8/1974 | Knrpler | 356/188 X |
| 3,861,788 | 1/1975 | Webster | 356/188 X |
| 3,909,598 | 9/1975 | Collins et al. | 364/567 |
| 4,050,016 | 9/1977 | Marsh et al. | 324/61 R |
| 4,058,766 | 11/1977 | Vogel et al. | 324/61 R |
| 4,080,563 | 3/1978 | Marsh et al. | 324/61 R |
| 4,093,991 | 6/1978 | Christie Jr., et al. | 364/498 X |
| 4,121,151 | 10/1978 | Funk et al. | 324/61 R |

*Primary Examiner*—Edward J. Wise
*Attorney, Agent, or Firm*—Trexler, Wolters, Bushnell & Fosse, Ltd.

[57] ABSTRACT

An analysis instrument for measuring selected constituents present in a sample of a material such as a bulk commodity includes a test cell to receive the sample. The test cell comprises a capacitor whose electrical properties are modified in accordance with the dielectric constant of the sample, which dielectric constant is a function of the contents of the sample. Weight and temperature sensors are provided for producing signals corresponding to the weight and temperature of the sample in the test cell. An electronic measuring circuit is connected to a test circuit including the test cell capacitor and to the weight and temperature sensors for producing an indication of the contents of the sample. The measuring circuit produces the indication by correcting a measurement taken across the test cell in accordance with the variation in the temperature of the sample from a reference temperature and the variation in the bulk density of the sample from a reference bulk density. Control circuits are provided for controlling the overall operation of the analysis instrument in accordance with predetermined instructions stored therein and with operator instructions from a control panel.

35 Claims, 22 Drawing Figures

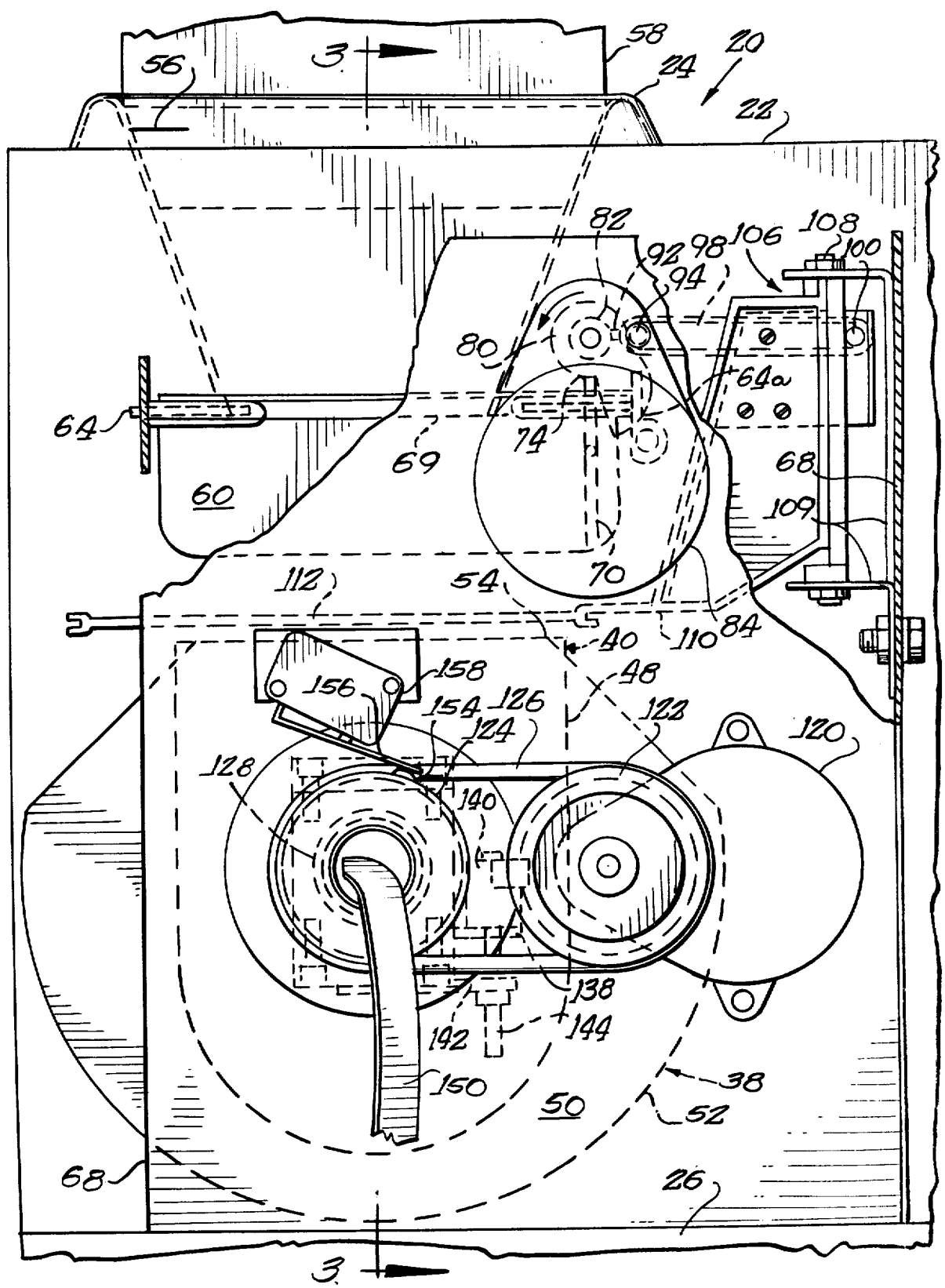

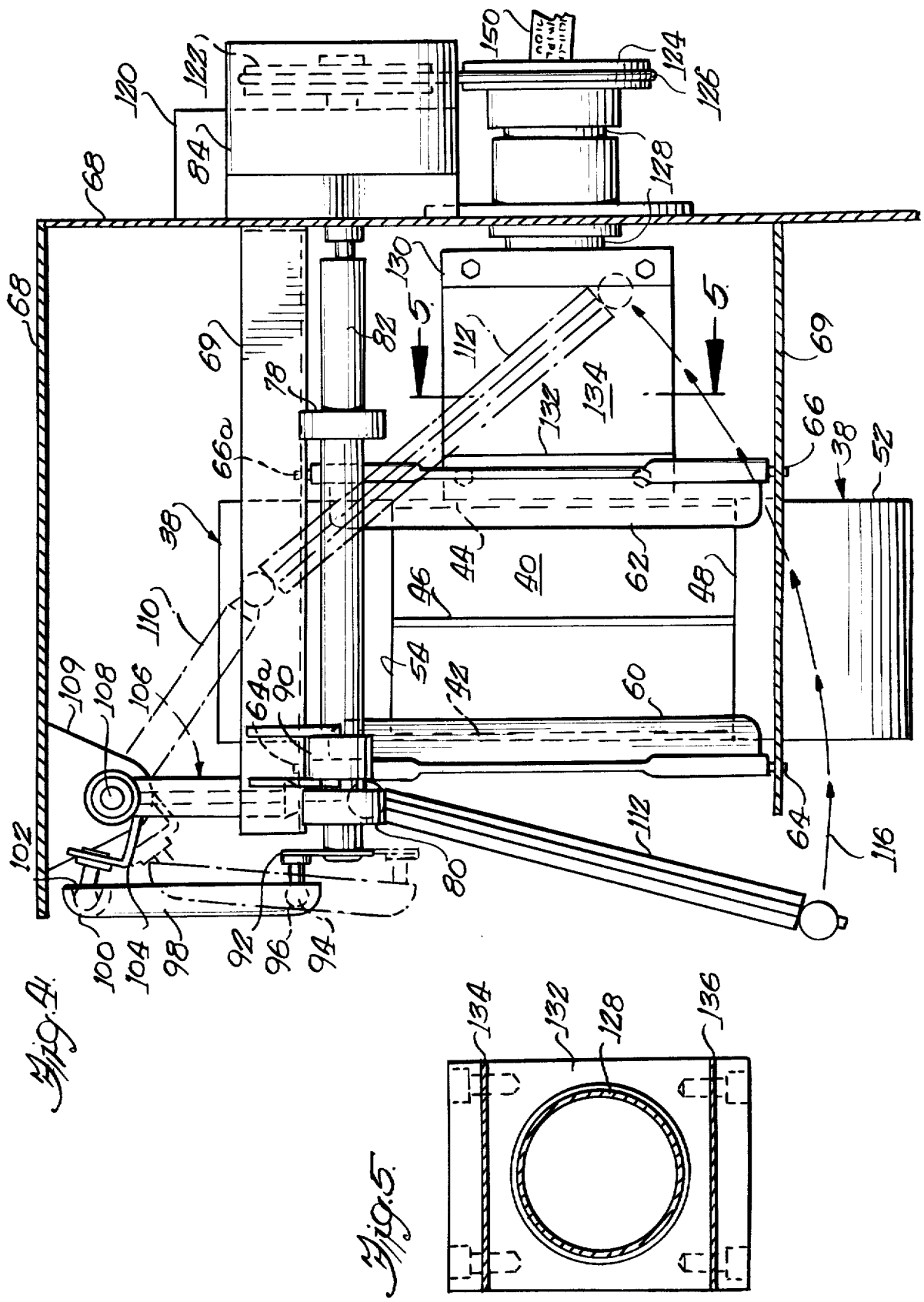

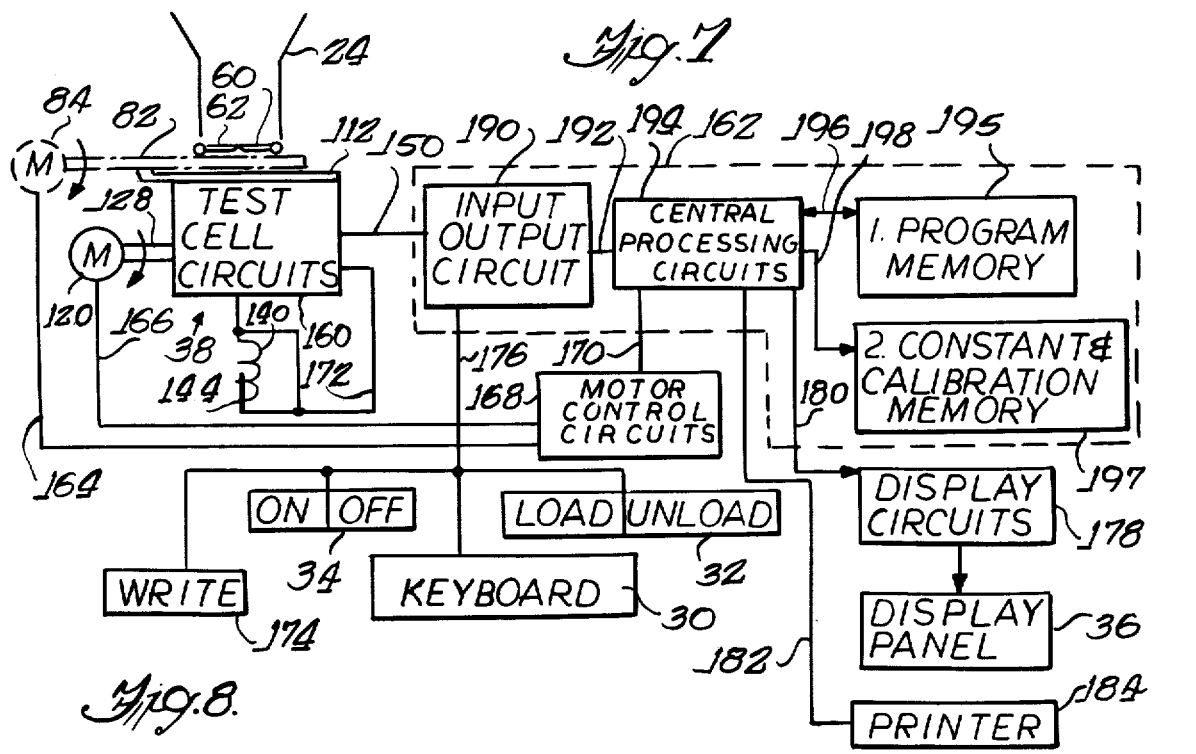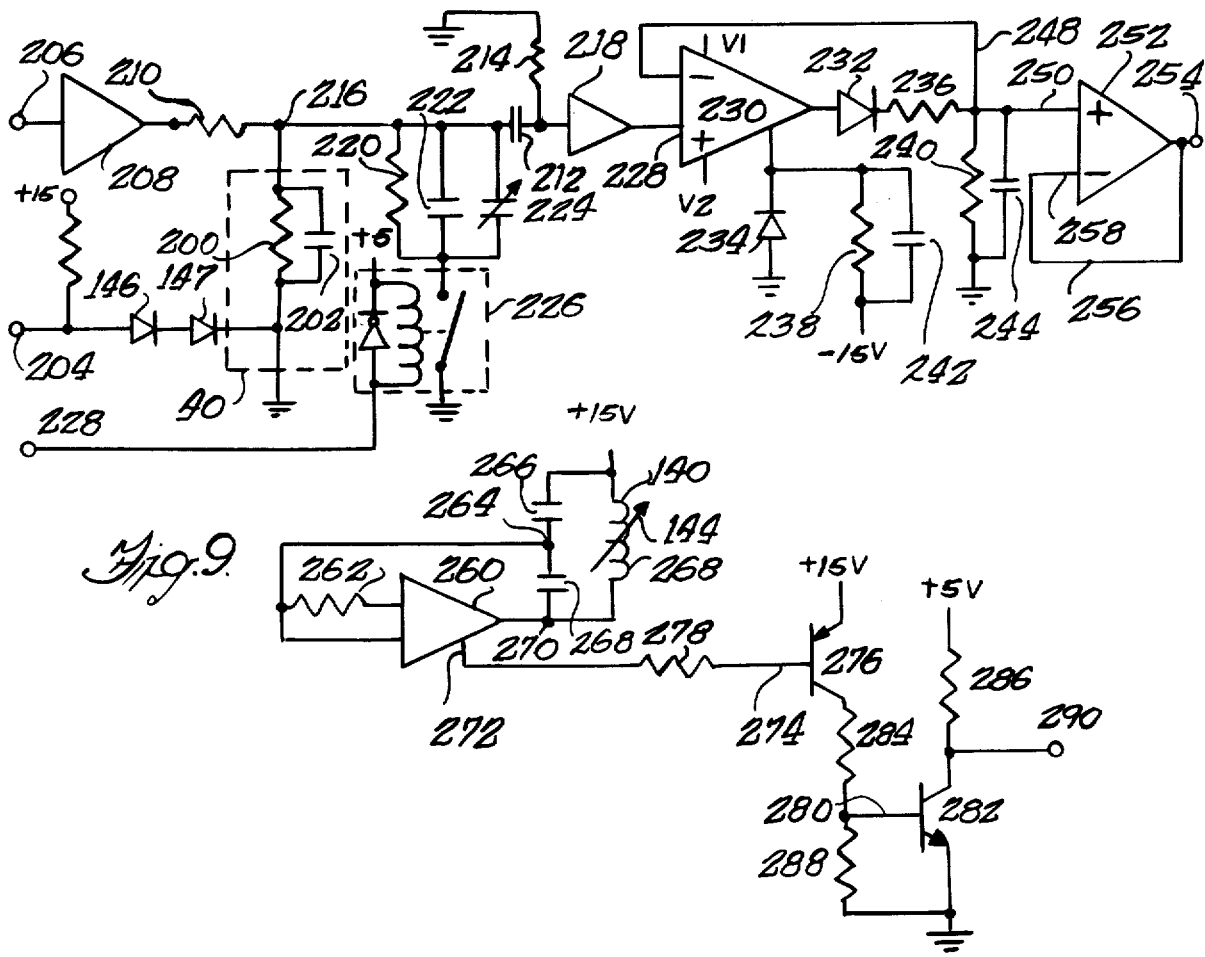

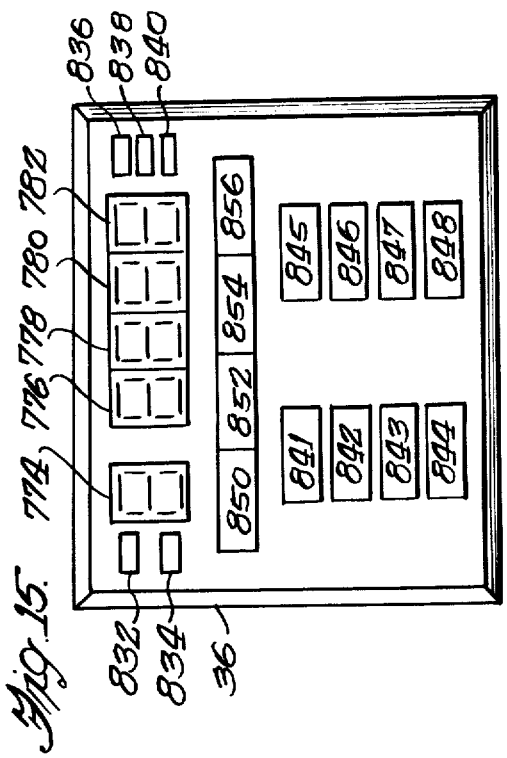
Fig. 15.
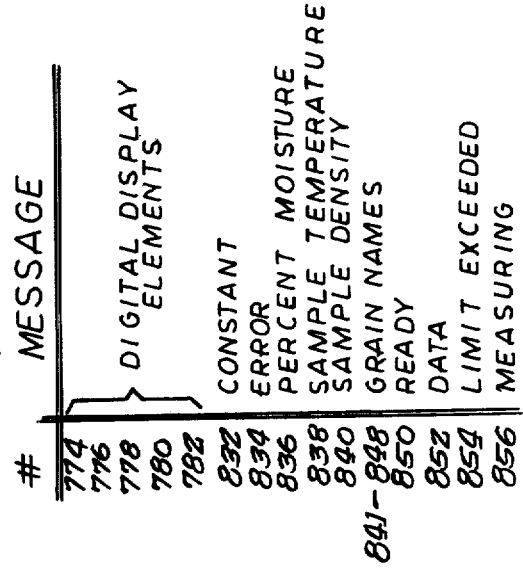
Fig. 16.
| # | MESSAGE |
|---|---|
| 774 | DIGITAL DISPLAY ELEMENTS |
| 776 | |
| 778 | |
| 780 | |
| 782 | |
| 832 | CONSTANT |
| 834 | ERROR |
| 836 | PERCENT MOISTURE |
| 838 | SAMPLE TEMPERATURE |
| 840 | SAMPLE DENSITY |
| 841-848 | GRAIN NAMES |
| 850 | READY |
| 852 | DATA |
| 854 | LIMIT EXCEEDED |
| 856 | MEASURING |
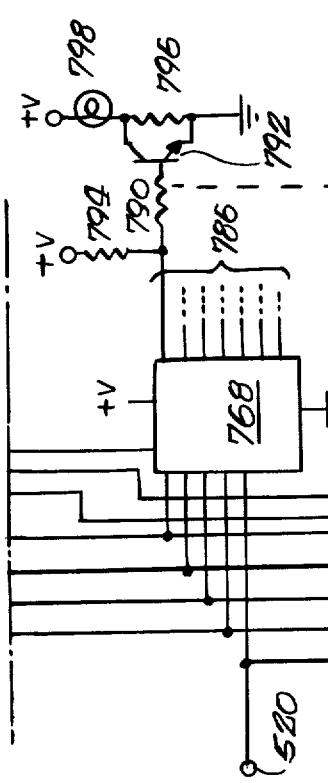
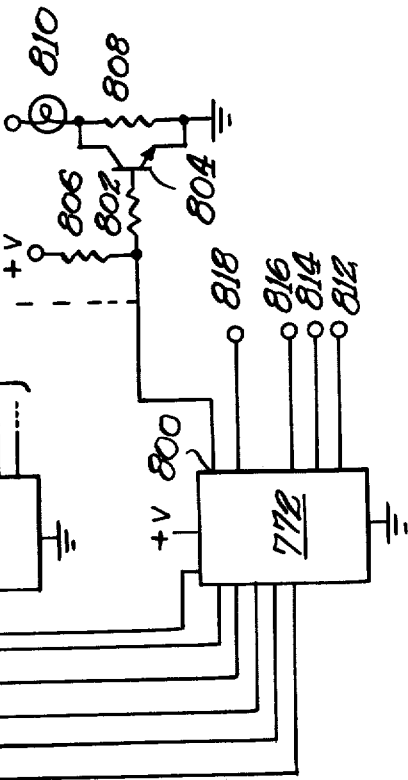
Fig. 14B.

ANALYSIS INSTRUMENT

CROSS REFERENCE TO RELATED APPLICATION

This application is a continuation-in-part of Ser. No. 791,641, filed Apr. 27, 1977, abandoned.

BACKGROUND OF THE INVENTION

This invention relates to material analysis apparatus, and more particularly to apparatus for measuring the contents of a bulk commodity, such as a grain. The description will be facilitated by addressing the specific problem of measuring the moisture content of a farm grain, such as corn, soybeans or the like.

In measuring the moisture content of a grain, it is known to use a test cell that comprises a capacitor in which the grain sample is introduced and to obtain a reading representative of a moisture content based upon an electrical measurement of the grain filled capacitor. In the past, such measurements have been made by connecting the test cell as a capacitor in the tank circuit of an oscillator and inferring the capacitance of the test cell from a measurement of the frequency of the oscillator. This approach is limited by the assumption that the test cell represents an ideal or pure capacitor, failing to take into account the conductance of a real capacitor, also present in the test cell. Thus, some degree of error is inherent in this method of measurement. Also, the real capacitor of the test cell has a complex admittance comprising a capacitive component and a frequency dependent resistive component often called the loss factor. Thus, the above measurement also fails to take into account the frequency dependent resistive component.

The dielectric constant of a material causes a change in the electrical properties of a capacitor when the material is introduced in its field region, compared to the properties of the same capacitor when its field region is devoid of material. In general, the dielectric constant of a material is a function of the physical properties or constituents of the material. Thus the dielectric constant and therefore the properties or constituents of a material may be derived by introducing the material into a test cell constructed as a capacitor and measuring the change in voltage across the test cell as compared to the voltage across the empty test cell with the same signal applied thereto. If the test cell is included in an electrical network in which other components are of known fixed values and a known signal is applied to the network, voltage or gain measurements taken across the test cell filled with the sample material can be used to calculate the dielectric constant of the material. It can be shown that the conductance of the test cell capacitor with a material of known bulk conductivity therein is proportional to the capacitance of the evacuated capacitor. Thus, it is possible to eliminate the effects of the conductance and allow for the effects of both the capacitive and the frequency dependent resistive components of the real capacitor comprising the test cell by correlating separate voltage measurements taken across the test cell when empty and when filled with the sample, with signals of at least two different frequencies applied to the test cell.

Since grain moisture is defined as a percentage by weight of moisture, it has been necessary in previous moisture testing apparatus to first weigh a sample and then introduce the sample into the test cell. A preliminary moisture reading may then be obtained on the instrument either by use of a properly calibrated meter or calculating moisture from a readout on the instrument in conjunction with a chart. After this preliminary moisture calculation has been obtained, however, it is necessary to apply a correction factor for the temperature of the sample. Thus, it is necessary to measure the temperature of the sample and by reference to a suitable table or chart obtain a temperature corrected moisture reading. Also, in the case of farm grains, the moisture reading must be corrected in accordance with the variance of the bulk density of the sample from a standard bulk density. Thus, it is necessary to determine the volume of the sample being tested, in addition to its weight, to determine the density thereof. Then an additional calculation must be made, or chart referred to, to obtain a moisture content reading corrected for bulk density.

It can be seen that the foregoing procedures are relatively cumbersome when carried out with prior art apparatus due to the inconvenience of performing multiple separate measuring steps, in order to obtain a value of moisture content as corrected for bulk density and temperature. Also, it is inconvenient to perform several calculations and/or to refer to charts or tables to derive this final corrected value of moisture content.

OBJECTS AND SUMMARY OF THE INVENTION

Accordingly, it is a general object of this invention to provide an analysis instrument which is convenient to use, in high speed in operation, and automatically performs all measurements and computations necessary to obtain the contents of a sample.

A more specific object of this invention is to provide an analysis instrument in accordance with the foregoing object, for measuring the moisture content of a sample in accordance with the dielectric constant of the sample.

Still another object of this invention is to provide an analysis instrument in accordance with the foregoing objects, adapted to measure the bulk density of the sample, and automatically modify the moisture measurement in accordance with the variation of the bulk density of the sample from a reference standard bulk density.

Yet another object of this invention is to provide an analysis instrument, in accordance with the foregoing objects, further adapted to measure the temperature of the sample and to modify the moisture measurement according to the variation of the temperature of the sample from a reference temperature.

A further object of this invention is to provide an analysis instrument in accordance with the foregoing objects, adapted to perform the foregoing measurements and computations automatically to provide a readout representative of the moisture content of the sample as corrected for bulk density and temperature of the sample as a percentage of total weight.

Briefly, and in accordance with the foregoing objects, an analysis instrument according to the present invention comprises a test cell for receiving a sample of the material to be tested, the test cell comprising a capacitor whose electrical properties are modified in accordance with the dielectric constant of the sample, which dielectric constant is a function of the contents thereof. The analysis instrument further includes circuit means including means for applying two electrical signals of different predetermined frequencies to the test cell and means for applying the two electrical signals to the test cell when the test cell is empty and for again applying the two electrical signals to the test cell when the sample is received therein. The analysis instrument also includes test circuit means including the test cell capacitor for receiving the applied signals and for producing test signals in response thereto, the test signals corresponding to the dielectric constant of the material. The circuit means further include measurement circuits for receiving the test signals and providing an indication corresponding to the contents of the material in accordance with the test signals.

In a preferred embodiment, the instrument includes means for producing a weight signal corresponding to the weight of the sample and the measurement circuit includes means for receiving the weight signal and producing a bulk density signal in response thereto corresponding to the bulk density of the sample, and for providing an indication of the bulk density of the sample in accordance with the bulk density signal. The measurement circuit further includes means for modifying the moisture indication according to the variation of the bulk density of the sample from a predetermined reference bulk density in accordance with the bulk density signal. In a preferred embodiment, the analysis instrument also includes means for producing a temperature signal corresponding to the temperature of the sample, the measurement circuits further including means for receiving a temperature signal and producing an indication of the temperature of the sample in accordance therewith and means for modifying the moisture indication according to the variation of the sample temperature from a predetermined reference temperature in accordance with the temperature signal.

Also in a preferred embodiment, the circuit means further include control circuit means for automatically controlling, in a sequence, the applications of the two applied electrical signals to the test cell, the reception of the test, temperature, and weight signals by the measurement circuit, the providing of the moisture temperature and bulk density indications and the modifying of the moisture indication, in accordance with predetermined instructions stored in the control circuit means and in accordance with operator instructions from a control panel.

The foregoing, as well as other objects, features and advantages of the present invention will be appreciated from a consideration of the following detailed description together with the accompanying drawings in which like reference numerals are used throughout to designate like elements and components.

BRIEF DESCRIPTION OF THE DRAWINGS

FIG. 2 is an enlarged view, partially cut away, of a portion of the instrument of FIG. 1, taken generally along the line 2—2 of FIG. 1;

FIG. 4 is a view of the instrument of FIGS. 1, 2 and 3, taken generally along the line 4—4 of FIG. 3;

FIG. 5 is a view of a portion of FIG. 4 taken generally along the line 5—5 of FIG. 4;

FIG. 7 is a block diagram of the electrical components of the instrument of the present invention;

FIGS. 8 and 9 are detailed schematic diagrams of circuits included in the test cell circuits of FIG. 7;

FIGS. 14A and 14B are a detailed schematic diagram of the display circuits of FIG. 7;

FIG. 15 is an elevational view of the readout and display panel of the moisture tester of FIG. 1;

FIG. 16 is a representation, in tabular form, of the elements of the display panel of FIG. 15;

DETAILED DESCRIPTION

The following detailed description is facilitated by addressing the problem of measuring the moisture of a sample of a farm grain. Thus, the analysis instrument of the present invention will be referred to hereinafter as a moisture tester.

Figure 1:
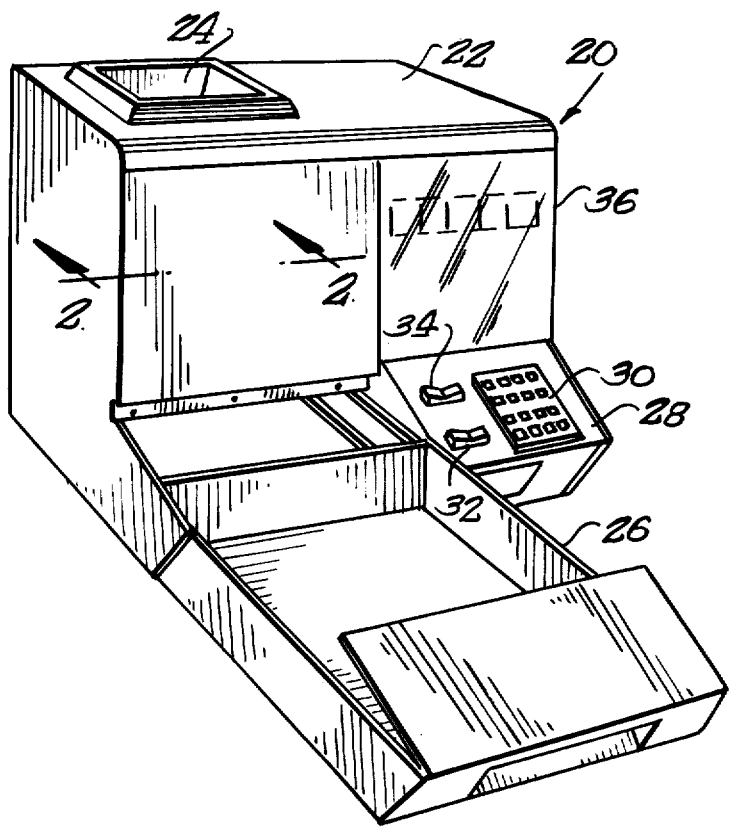
FIG. 1 is a perspective view of an analysis instrument incorporating features of the present invention.

Referring now to FIG. 1 a moisture tester 20 comprises a housing 22, having a hopper 24 mounted at the top thereof for receiving a quantity of material whose moisture content is to be measured. The moisture tester 20 also includes a drawer 26 slidably mounted in the bottom portion thereof to receive the sample material subsequent to testing and to effect the removal thereof from the tester. The sample door 26 is also removable from the moisture tester 20 to provide for the use of other suitable means in its place to effect removal of sample material after testing thereof. The moisture tester 20 also includes a control panel 28 including a keyboard comprising a four- by four array of control switches 30 which may comprise push button type switches, a load-unload switch 32 and an on/off switch 34. The operation of these controls is further explained hereinbelow. The moisture tester 20 also includes a display panel 36, the structure and operation of which are explained hereinbelow.

Figure 3:
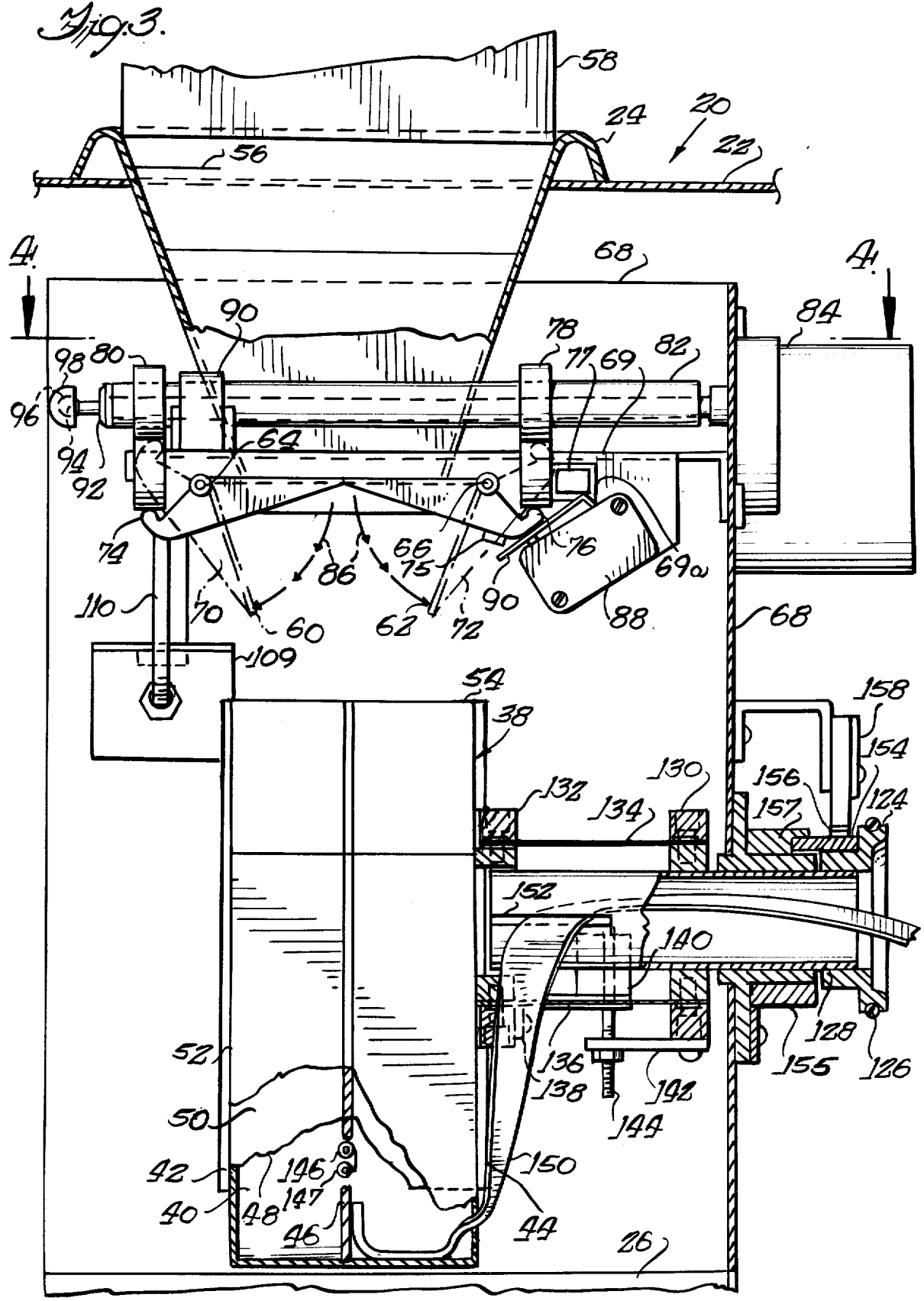
FIG. 3 is a view of the instrument of FIGS. 1 and 2, taken generally along the line 3—3 of FIG. 2.

Referring now to FIGS. 2, 3 and 4, the sample handling portion of the moisture tester 20 is illustrated in greater detail. A test cell assembly 38 includes a test cell 40 to receive a sample of the material to be tested, which comprises a capacitor made up of generally flat, U-shaped end plates or electrodes 42 and 44 constructed of suitable conductor material, and a somewhat larger flat center plate 46 which comprises printed circuit board material having both sides thereof copper plated to define a center electrode of generally the same dimensions as the electrodes 42 and 44 and to define suitable interconnecting wiring patterns generally outside of the electrode surfaces for circuit elements to be mounted on the plate 46 described hereinbelow. An enclosure or wall member 48 comprises two pieces of suitable insulating material shaped to define enclosures between the respective end electrodes 42, 44 and the center plate 46. An outer enclosure member 52 of the test cell assembly 38 is constructed of a suitable insulating material, the end electrodes 42 and 44 preferably being mounted on the outside of the enclosure member 52 and the center plate 46 being generally co-planar with a cross section of the enclosure 52 and mounted substantially centrally therein. The wall member 48 and enclosure 52 define between them a chamber 50, which provides a suitable enclosed space for containing the aforementioned wiring patterns formed on the center plate 46 and the circuit elements mounted thereon. It will be noted that the test cell 40 is provided with a substantially rectangular opening 54, defined by the end electrodes 42, 44 and the side portions of wall member 48, and substantially level with the top of the test cell 40, through which a sample of material tested is introduced, as described below.

A hopper 24 is mounted directly above the test cell assembly 38 to receive a quantity of grain to be tested, and is provided with a fill line or indicator mark 56 to show the minimum amount of material necessary to assure proper filling of the test cell 40. A hopper extension member 58 may be removably mounted over the hopper 24 to assure filling thereof with material well over the minimum filling mark 56. A pair of doors 60 and 62 are mounted below the hopper 24 to define a bottom thereof. The doors 60 and 62 are mounted upon hinge pins 64 and 64a and 66 and 66a so as to be selectively rotatable about the hinge pins 64 and 64a and 66 and 66a, the ends of which are in turn respectively affixed to opposite ends of a mounting plate 69 affixed to an inner housing 68 suitably positioned within the housing 22. The doors 60 and 62 are provided with support members 70 and 72 each including an ear or actuator member 74 and 76 at an end thereof radially outwardly from the respective hinge pins 64 and 66. A pair of cams 78 and 80 are mounted for rotation upon a horizontally extending shaft 82 which is driven by a motor 84 attached to the inner housing 68, the cams 78 and 80 being in engagement with the ears or actuator members 74 and 76 of the door support members 70 and 72, respectively. Thus, the doors 60 and 62 are selectively openable in the direction indicated by the arrows 86 via the action of cams 78 and 80, whose rotation by shaft 82 via the motor 84 allows doors 60 and 62 to rotate about hinge pins 64 and 66, respectively. A magnetically actuatable reed-type switch 88 is mounted on a non-magnetizable plate 69a affixed to the plate 69 and a magnet 75 is mounted on the support member 72 of the door 62 actuating the switch 77 to provide an indication to electronic control circuitry to be described later herein, when the doors 60 and 62 are fully opened. A switch 88 is mounted on the plate 69 and includes a actuator 90, to be actuated by the support member 72 when the doors 60, 62 are fully closed to provide a similar indication. The shaft 82 is also mounted by suitable bearing means 90 mounted upon the plate 69 at a portion thereof remote from the motor 84 to insure smooth and even rotation of the shaft 82. The shaft 82 is also provided with radially extending arm or member 92 fixed to its end opposite the motor 84 which includes a first ball member 94 attached to the radially outward end thereof to rotate at a fixed radius about the center of the shaft 82. The ball member 94 is fixed in a socket 96 which forms a first end of a linkage member 98, the opposite end thereof defining a second socket 100 in which is fixed a second ball member 102. The second ball member 102 includes a linkage 104 formed at its end opposite the socket 100 and attached by suitable means to a strike off assembly 106. Strike off assembly 106 includes a shaft 108 rotatably mounted on means 109 attached to housing 68, and a linkage 110 affixed to rotate together with the shaft 108 and including an elongate, strike off arm 112 positioned parallel to and just above the level open top portion 54 of the test cell 40. It will be appreciated from the foregoing that as the shaft 82 rotates, the member 92 and ball 94 affixed thereto rotate about the shaft 82, thereby actuating the linkage member 98 to pull the ball member 102 and attached linkage 104 in such a manner as to actuate the strike off assembly 106 to move or rotate the linkage 110 thereof and its elongate strike off arm 112 about the shaft 108 substantially as indicated by the arrows 116 so that the elongate strike off arm 112 passes over the open top 54 of the test cell 40, moving completely from one end to the other thereof to the position indicated in FIG. 4 by the dotted lines. Similarly, continued rotation of the shaft 82 by the motor 84 returns the wiper arm assembly 106 to its original position and via the cams 78 and 80 again closes the doors 60 and 62. The strike off arm 112 preferably comprises a semi-rigid elongate member and an extension spring generally coextensive with and attached to the elongate member to compensate for irregularly shaped sample material as it strikes off the excess while moving across the top of the test cell 40.

It will be noted that the relative positioning of the cams 78 and 80 and member 92 upon the shaft 82 are such that the movement of the strike off assembly 106 and the strike off arm 112 thereof are synchronized with the opening and closing of the doors 60 and 62, so that the strike off arm moves across the open top 54 of the test cell 40 shortly after the opening of the doors 60 and 62. Thus, it will become apparent that the motor 84 via the shaft 82 controls a sequence of operation wherein sample material is first released via the doors 60 and 62 from the hopper 24 into the test cell 40, over-filling the test cell 40 and subsequently, the strike off arm 112 is moved across and level with the open top 54 of the test cell 40 as described, and strikes off and carries away excess sample material from the top 54 thereof, the doors 60, 62 being simultaneously closed, resulting in the test cell 40 being filled with sample material of a constant predetermined volume as set by the leveling action of the strike off arm 112. Thus, the described indication given by the switch 88 also corresponds to the strike-off operation being completed.

Referring now again to the test cell assembly 38, it will be seen that a motor 120 is provided along with a pair of pulleys 122, 124 and a drive belt 126 therebetween to drive a shaft 128 which is connected to rotate the test cell assembly 38 as follows. A first collar 130 is attached to the shaft 128 for rotation therewith. A second collar 132 is attached to the test cell assembly 38 to rotate in unison therewith, an interior opening of the collar 132 being clear of the shaft 128. The amount of clearance provided for the shaft 128 by the interior opening of the collar 132 effectively defines limits of movement of the test cell assembly 38 with respect to the motor 120 and shaft 128. A pair of flexure plates 134 and 136 are attached between the respective collars 130 and 132 so that the test cell assembly 38 may be rotated through 180° by the motor 120 via the shaft 128 and via the collars 130 and 132 and connecting flexure plates 134 and 136 in order to unload or remove the sample material from the test cell 40, when testing is completed. FIG. 5 illustrates a view of the collar 132 and flexure plates 134 and 136 taken generally along the line 5—5 of FIG. 4.

The collars 130 and 132 and flexure plates 134 and 136 also form a portion of weighing means for measuring the weight of the sample contained in the test cell 40. A suitable mounting means 138 is attached to the collar 132 for holding a coil 140. Similarly, a mounting member 142 is attached to the collar 130 and holds a shaft or core member 144. The opposite end of shaft or core member 144 extends through the center of the coil 140. Thus the coil 140 and shaft 144 comprises a variable inductor. The flexure plates 134 and 136 are adapted to flex or give somewhat in response to the weight of sample material introduced into the test cell 40 so as to provide some relative movement between the collar 130 attached to the shaft 128 and the collar 132 attached to the test cell assembly 38. Thus, it will be appreciated that the coil 140 attached to the collar 132 and the core member 144 attached to the collar 130 will experience a relative change in their positions due to the flexing of flexure plates 134 and 136, said movement being in proportion to the weight of the sample material introduced into the test cell 40. The change in inductance provide by the relative movement between the coil 140 and core member 144 will correspond to the relative movement therebetween, and therefore to the weight of the sample material in the test cell 40. Suitable wires or leads are provided (not shown) to energize the coil 140 to produce a weight signal thereacross proportional to the inductance thereof and to connect the coil to a suitable weighing circuit in the chamber 50 to be described hereinbelow. It will be appreciated that the aforementioned limits of movement defined by the clearance of the collar 132 about the shaft 128 serves to protect the coil 140 and core member 144 from possible damage due to large deflections of the plates 134, 136 which might otherwise occur during loading of a sample into the test cell or when the moisture tester is being transported.

The test cell 40 also includes, mounted in the middle plate 46 thereof, a pair of temperature sensors 146, 147 to provide a signal corresponding to the temperature of the sample to be contained therein. It will be appreciated that the positioning of the temperature sensors 146, 147 substantially in the central, interior portion of the test cell 40, provides an optimum temperature reading, as the sample material, once introduced into the test cell 40, will substantially surround the sensors 146, 147. Suitable printed circuit conductors are provided on the plate 46 from the temperature sensors 146, 147 to the chamber 50 containing the test cell circuits. A suitable electrical cable 150, in the form of a flat ribbon-type cable is provided to connect the circuit components in the chamber 50 of the test cell assembly 38 with the other measurement and control circuits of the moisture tester. The flat cable 150 is directed through a suitable slot 152 provided therefore in the shaft 128, the shaft 128 being hollow to allow the passage of cable 150 therethrough to exit at the end thereof through a suitable opening provided therefore in the pulley 124. The cable 150 includes a plurality of leads or wires adapted to make appropriate connections between the circuits of the test cell 40 and measurement and control circuits of the moisture tester to be described in detail hereinbelow.

The pulley 124 is further provided with a raised stop member 154 which is adapted to engage second and third stop members 155, 157 mounted 180° apart upon the housing 68 adjacent the pulley 124, when the pulley 124, shaft 128 and test cell assembly 138 are rotated through approximately 180° to unload or empty the sample material from the test cell 40 and again right the test cell upon completion of testing. The raised stop member 154 also engages an actuator 156 of a switch 158 when the test cell assembly is in its upright position to provide a signal for control circuits of the moisture tester, to be described below, corresponding to the location of the test cell 40 in either the upright (switch closed) or in the sample removal (switch open) position. It will be noted that the motor 120 preferably comprises an induction-type permanent magnet synchronous motor which is adapted, in conjunction with a motor control circuit described below, to automatically reverse its direction of rotation with the stop member 154 engages the complimentary stop members 155 and 157 so as to automatically right the test cell assembly 38 following the unloading of the sample material therefrom and vice-versa.

Figure 6:
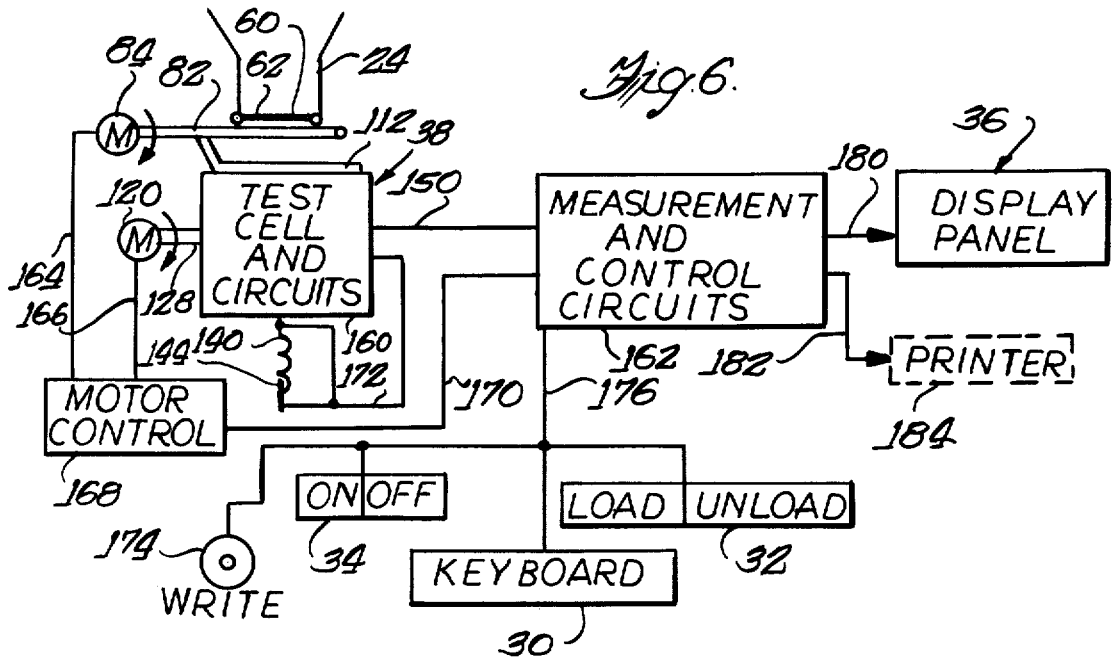
FIG. 6 is a simplified block diagram showing the overall arrangement of the instrument of FIGS. 1 through 5.

Turning now to FIG. 6, a block diagram illustrates the overall arrangement of the moisture tester of FIGS. 1 through 5, including the test sample portion hereinabove described as well as additional measurement and control circuitry to be described in further detail hereinbelow. The portions of the apparatus described hereinabove are indicated by the same numbers in FIG. 6. Test cell circuits 160 including a weighing circuit are mounted as described above, on the printed circuit portion of the plate 46 in the chamber 50 provided therefore in the test cell assembly 38, and connected to the other circuits of the moisture tester via the cable 150 described above. The test cell circuits 160 include a suitable peak detector circuit to be described below, to receive the signals developed across the test cell 40 and provide a suitable peak portion thereof. It will be appreciated that the mounting of these circuit components on the plate 46 in the chamber 50, adjacent the test cell 40 substantially eliminates "cable effects" such as noise, cable capacitance, static or the like which might otherwise affect the relatively low level portions of test cell signals if transmitted, modified, over the cable 150. Cable 150 connects test cell circuits 160 with measurement and control circuits 162. Lines 164 and 166 connect the motors 84 and 120, respectively with a motor control circuit 168 which is in turn connected to the measurement and control circuit 162 via line 170. The weight sensor comprising coil 140 and core member 144 is connected to the weighing circuit portion of the test cell circuits 160 by line 172. The keyboard 30, load/unload switch 32 and on/off switch 34, together with a write switch 174, are connected via line 176 to the measurement and control circuits 162. Display circuits associated with the display panel 36 are connected via a line 180 to the measurement and control circuits 162. A line 182 connects the measurement and control circuits 162 to a printer 184 which may optionally be provided separate from the moisture tester to provide a written record of the measurement taken thereby.

Briefly, the operation of the moisture tester is as follows: Instructions from the control panel 28 and specifically from the actuation of the load/unload switch 32 to the load position provide instructions to the control circuit portion of the measurement and control circuits 162 via line 176 causing the control circuit to activate the motor control 168 via the line 170 to rotate the motor 84 via line 164 for rotating the shaft 82 to actuate the doors 60 and 62 and the strike off assembly 106 as described above. A quantity of the sample material is thus released from the hopper 24 into the test cell 40 and adjusted to a predetermined constant volume by the strike off arm 112, as described above. The measurement and control circuits 162 initiate measurements of temperature, weight and moisture content of the sample in the test cell and provide for correlation and display of the measurements via the line 180 and the display panel 36 or for printing of the measurements via the line 182 and printer 184 in accordance with operator instructions via the keyboard 30. When the measurements have been completed, the operator may actuate the load/unload switch 32 to the unload position, thereby signaling the measurement and control circuits 162 via line 176 to activate the motor control 168 via line 170 for rotating the motor 122 via line 166 to unload or remove the sample material from the test cell as described above. The foregoing as well as additional operative aspects of the moisture tester, including the keyboard 30, measurement and control circuits 162 and display circuits 178 are described in additional detail hereinbelow.

Referring now to FIG. 7, the electrical components of the moisture tester are shown in block diagrammatic form, along with a simplified diagrammatic representation of the sample handling components of the moisture tester described in detail above. It will be noted that elements of FIG. 6 are repeated in FIG. 7 and are to be understood as comprising the same elements as the like numbered elements of FIG. 6. The measurement and control circuits 162 are illustrated in greater detail in FIG. 7 and include an input/output circuit 190 which receives signals from the test cell circuits 160 via the line 150 and from the keyboard 30, load/unload switch 32, on/off switch 34 and write switch 174 via the line 176. The input/output circuit 190 is connected via a line 192 to a central processing circuit 194. The central processing circuit 194 is connected via a line 180 to the display circuits 178 and via a line 182 to the printer 184. Also provided as part of the measurement and control circuits 162 are a program memory 195 and a constant and calibration memory 197 connected via lines 196 and 198, respectively, to the central processing circuit 194.

The foregoing circuits will be described in detail hereinbelow. However, it is advantageous to give a general description, at this point, of the operation of the circuit blocks thus far described.

As described above, the test cell 40 is constructed as a capacitor and is connected as part of a circuit or electrical network in which the other components are of known fixed values. This network is included as part of the test cell circuits 160. The test cell circuits 160 also receive inputs from the temperature sensors 146 and 147. The measurement and control circuits 162 include means for applying signals at predetermined frequencies to the network including the test cell capacitor. As described above, voltage readings are taken across the test cell capacitor when the test cell is empty and again when the test cell is filled with sample material with signals of at least two different frequencies sequentially applied to the test network. In this manner, the dielectric constant of the sample can be inferred from the voltages measured across the test cell, compared to the voltages measured across the test cell when its field region is devoid of material, and related to the moisture content of the sample in the test cell. As also described above, this application of signals and taking of voltage measurements at two frequencies substantially eliminates the effects of conductance of the test cell on the dielectric constant so inferred. The line 150 connects the test cell circuits to the input/output circuit 190 which receives signals from the test cell circuits representative of the voltages developed across the test cell when the test cell is empty and is filled with sample material at each of the applied frequencies. The input/output circuit 190 also receives signals from the test cell circuits 160 representative of the temperature and weight of the sample as sensed by the temperature sensors 146 and 147, and the weight sensor comprising the coil 140 and core member 144.

The foregoing moisture, weight and temperature signals are put into suitable form in the input/output circuits 190 to be transferred via the line 192 to the central processing circuit 194. The central processing circuit 194 includes measurement circuits adapted to obtain the moisture content of the sample by performing a series of operations upon the foregoing received signals. As at least four voltage measurements must be made across the test cell prior to obtaining the moisture content of the sample, the central processing circuit 194 is adapted to store in an electronic memory portion thereof the voltage values obtained in each such measurement, until the four measurements have been completed. The weight and temperature measurements are also stored in the electronic memory until the central processing unit is ready to perform the necessary operations to derive the moisture content of the sample therefrom.

A first value of moisture content based on the voltage measurements only may be obtained by the equation: $M_A = K1 + K2X + K3 \log(X + K4)$, where $X = G2 + K5 (G5/G2)$; $M_A$ is value of moisture content as determined only from the voltage values obtained; K1, K2, K3, K4 and K5 are empirically determined constants from recorded data on specific materials; G2 is a log function of the ratio of loaded cell voltage to empty cell voltage at the first measurement frequency, and G5 is a log function of the ratio of loaded cell voltage to empty cell voltage at the second measurement frequency.

In the case of farm grains, the measure moisture content must be corrected according to the relation between the bulk density of the sample and a predetermined standard bulk density. Since the weight and volume of the sample are known, the bulk density thereof may be readily computed by the central processing unit 194. To correct the moisture value $M_A$ obtained above for the measured bulk density of the sample, $M_A$ must be multiplied by the ratio of a standard density for the material being measured to the measured density for the sample, according to the equation: $M_{DC} = M_A \times D$ standard/D sample. Where $M_{DC}$ is the value of moisture content corrected for sample density, $M_A$ is the moisture content as calculated above, D standard/D sample is the ratio of standard density of the material to the density of the sample under test. The standard densities of farm grains are published in the Official Grain Grading Standards of the United States.

Temperature compensation of the calculated moisture content is provided by adding to the calculated moisture value $M_{DC}$ an amount proportional to the product of the moisture value $M_{DC}$ and the difference between the temperature of the sample and a reference standard temperature: $M_2 = M_{DC} + K6 M_{DC}(T_S - T_{STD})$.

In the above calculations it will be noted that a number of predetermined constants are used to derive the moisture content of the sample as corrected for temperature and density thereof. The constant and calibration memory 197 comprises an electronic memory adapted to store data corresponding to the appropriate constants K1, K2, K3, K4, K5, K6, D Standard, $T_{STD}$ for a plurality of different materials such as farm grains, to adapt the moisture tester for accurately testing each of these commodities. The constants K1 through K6 are different for each material and are empirically determined from data recorded on respective materials. The standard reference temperature is chosen as an appropriate standard temperature for the material being measured, and in the case of farm grains, is chosen at 77° F. (25° C.). The standard bulk densities in the case of farm grains for each material are those published as described above. The volume of the sample is held constant by the apparatus as described above and its value is also stored in the constant and calibration memory 197.

The keyboard 30 is used by the operator to identify the material being tested and produces a signal corresponding thereto via the line 176 to the input/output circuits 190, which provide appropriate signals via the line 192 to the central processing circuit 194 for selecting via the line 198 the appropriate constants out of the memory 197 to calculate, together with the measurements made on the sample, the corrected moisture content for the sample thus identified. The central processing circuit 194 is then adapted to produce appropriate signals on line 180 or line 182 to the display circuits for providing a visual display of the moisture content or to a printer 184 to provide a written record thereof. It will also be noted that the central processing unit 194 is adapted to receive and execute commands from the keyboard 30 via line 176 the input/output circuit 190 and the line 192 to display or print figures corresponding to the measured temperature or measured density of the sample as well as the final corrected moisture as derived by the central processing circuit 194. The write button 174 may be used by the operator to command the central processing circuit 194 via the lines 176 the input/output circuit 190 and the line 192 to write new constants into the constant and calibration memory 197, as for example, to adapt the moisture tester for testing different materials or a broader range of values of moisture for materials whose constants are already stored therein.

As disclosed above, the control portion of the measurement and control circuits 162 is adapted to automatically control the loading, volume adjustment and sequence of measurement taking and indication-producing of the test cell and measurement and display circuits in accordance with operator instructions via the keyboard 30. The central processing circuit 194 is adapted to perform this function in accordance with information stored in a programmed memory such as the program memory 195, or in other electronic memory devices which will be described in detail hereinbelow.

Referring now to FIGS. 8–15, the circuits included in the block diagram of FIG. 7 are illustrated in detail. FIGS. 8 and 9 illustrate respectively the test cell circuits 160 and weight circuits, also included therein. Referring first to FIG. 8, the test cell capacitor 40 is represented by the parallel combination of a resistor 200 with a capacitor 202, connected to ground at one end thereof. The temperature sensing diodes 146 and 147 are connected in series between ground and a terminal 204, the cathode of diode 147 being connected to ground, the cathode of diode 146 being connected to the anode of diode 147, and the anode of diode 146 connected at terminal 204. A test signal is received at terminal 206 which is connected to the input of a buffer amplifier 208 whose output is connected to a test network including a resistor 210, connected at its opposite end to a terminal 216 at one side of the test cell capacitor 40 to form a voltage divider network. A voltage representative of the value of the test cell capacitor 40, represented by the parallel combination of a resistor 200 and a capacitor 202, is thus produced from the test signal by the test network at the terminal 216. The terminal 216 is connected to an AC coupling network comprising a capacitor 212 in series with a resistor 214 to ground, the junction of the resistor 214 with the capacitor 212 being connected to the input of a second buffer amplifier 218. A calibration network comprising the parallel combination of resistor 220, capacitor 222 and variable capacitor 224 is selectively connectable in parallel with the test cell capacitor 40 at the terminal 216 thereof, by a relay 226 which may be energized by operator command from the keyboard via the terminal 228 thereof to connect the opposite end of the calibration network to ground thereby including the parallel combination of resistor 220, capacitor 222 and variable capacitor 224 in the circuit for checking the operation of the moisture tester. The output of the buffer amplifier 218 is connected to an input 228 of a peak detector circuit comprising a high speed comparator 230, diodes 232 and 234, resistors 236, and 238 and 240 and capacitors 242 and 244. The input 228 comprises the non-inverting input of the comparator 230, whose output is connected to the anode of diode 232 which has its cathode connected in series with the resistor 236 and a feedback line 248 to the inverting input of the comparator 230. Resistor 240 and capacitor 244 are connected in parallel between the feedback line 248 and ground. The line 248 is also connected to the non-inverting input 250 of an operational amplifier 252 which has its output at terminal 254 connected via a line 256 to its inverting input 258. Thus, an output or peak detector signal at terminal 254 is proportional to the peak voltage developed by the test signal at terminal 216 across the test cell capacitor 40, represented by the parallel combination of the resistor 200 with the capacitor 202.

Referring now to FIG. 9, the weight sensor comprising the coil 140 and core member 144 is represented as a variable inductor. The weighing circuit comprises an oscillator whose output frequency is varied according to the value of the variable inductor comprising the coil 140 and core member 144. The weighing circuit oscillator comprises an operational amplifier 260 which has a resistor 262 connected across its two inputs. One end of the resistor 262 is also connected to a terminal 264 between capacitors 266 and 268 which are connected in series between a positive voltage supply and a first output 270 of the operational amplifier 260. The coil 140 is connected in parallel with the series capacitors 266 and 268 between the positive voltage supply and the first output 270 of the operational amplifier 260. A second output, at terminal 272, of the operational amplifier 260 receives a frequency signal therefrom proportional to the weight as sensed by the weight sensor comprising the coil 140 and core member 142. The output 272 is connected in series with the base terminal 274 of a PNP transistor 276 via a resistor 278. The transistor 276 has its emitter terminal connected to a positive voltage supply and its collector terminal connected in series with the base terminal 280 of a NPN transistor 282 via a resistor 284. The transistor 282 has its collector terminal connected via resistor 286 to a positive voltage supply, its emitter terminal connected to ground and its base terminal connected to ground via a resistor 288. An output terminal 290 is connected to the collector of the transistor 282 and carries a signal whose frequency is proportional to the weight of the sample. The frequency range of the weight signals may be chosen by choosing appropriate component values and may be, for example, in the range of 32 Kilohertz.

Figure 10A:
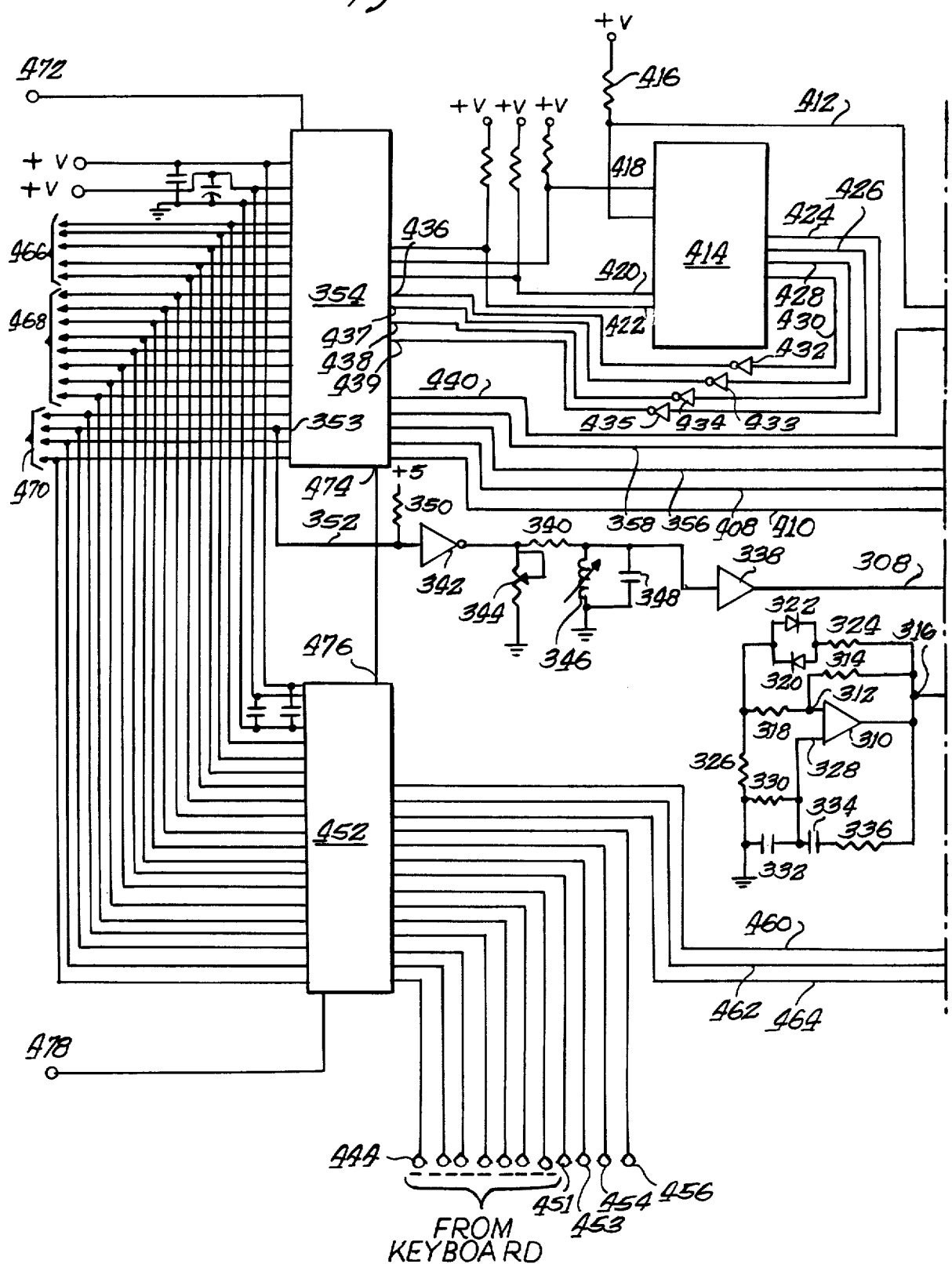
FIGS. 10A and 10B are detailed schematic diagrams of the input/output circuit of FIG. 7.
Figure 10B:
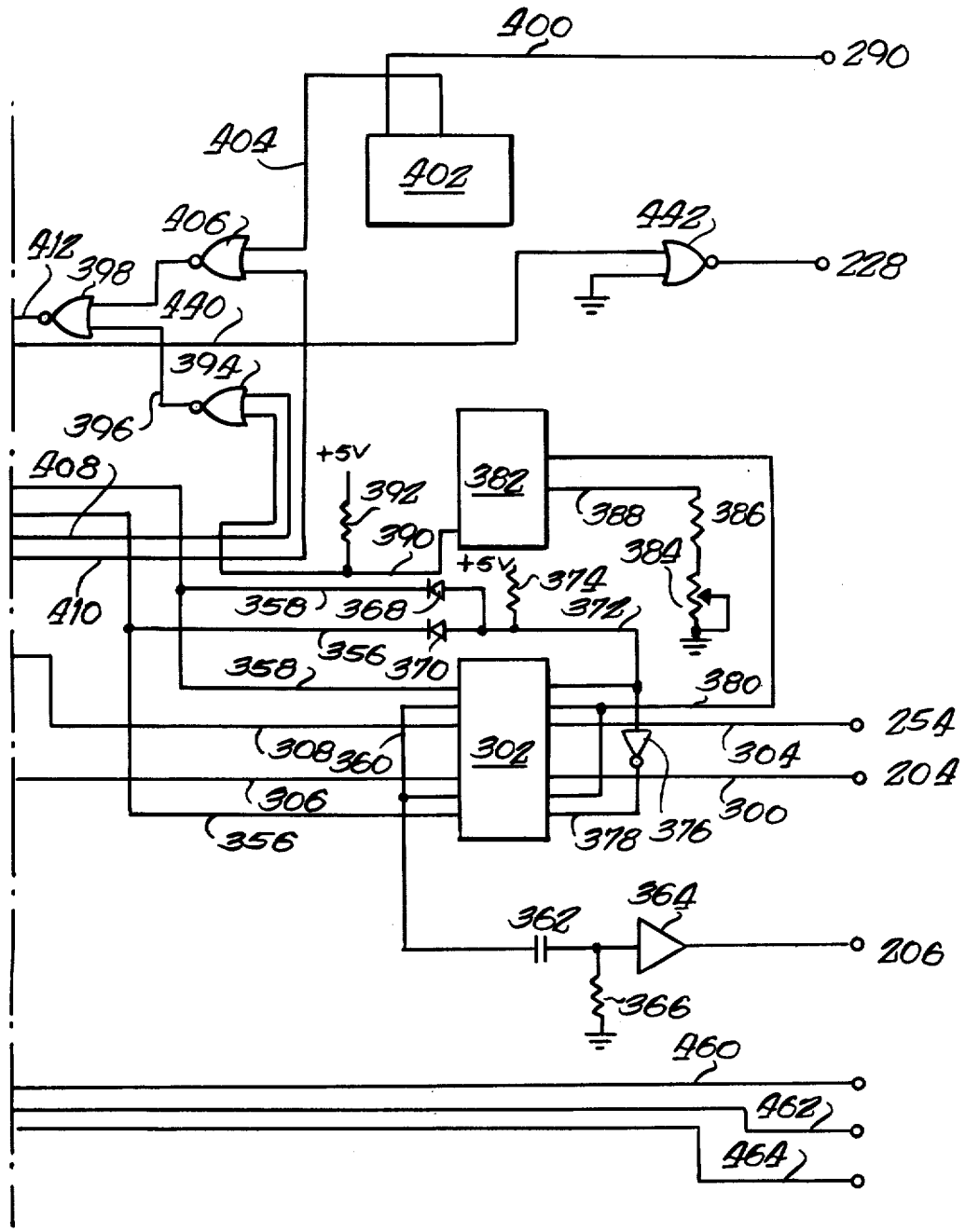

Referring now to FIGS. 10A and 10B, the input/output circuit 190 is illustrated in detail. Terminals 204, 206, 228, 254 and 290 are the same terminals as the like-numbered terminals of the circuits of FIGS. 8 and 9 and are again illustrated in FIG. 10B to show the interconnections between the circuits of FIG. 8 and FIG. 9 with the circuit of FIGS. 10A and 10B. The terminal 204, which carries the temperature signal, is connected via a line 300 to one input of an analog multiplexer 302. The terminal 254, which carries the peak detector signal is connected via a line 304 to a second input terminal of the analog multiplexer 302. The analog multiplexer 302 has two additional inputs connected to lines 306 and 308, which carry test signals developed by two sources shown in FIG. 10A.

Referring now to FIG. 10A, a first signal is supplied to the test network by an oscillator whose output is connected to line 306 and comprises an operational amplifier 310 which has a first input 312 connected via a resistor 314 to an output 316 thereof on the line 306. The input 312 is also connected via a resistor 318 to the cathode of a diode 320 and the anode of a diode 322. The opposite ends of the respective diodes 320 and 322 are joined and connected in series with a resistor 324 to the output terminal 316. The junction of the resistor 318 with diodes 320 and 322 is connected via a resistor 326 to ground. A second input 328 of the operational amplifier 310 is connected via the parallel combination of the resistor 330 and a capacitor 332 to ground. The input 328 is also connected via the series combination of a capacitor 334 and a resistor 336 to the output terminal 316. The components of this oscillator have their values chosen to determine the frequency of the sinusoidal output thereof which may be, by way of example, on the order of 5 kilohertz. The line 308 is connected to an output of a buffer amplifier 338 whose input is connected via a resistor 340 to the output of a buffer amplifier 342. A variable resistor 344 is connected between the output of a buffer amplifier 342 and ground. A variable inductor 346 and a capacitor 348 are connected in parallel between the input of a buffer amplifier 338 and ground to provide a sinusoidal signal to the buffer 338. The input of buffer amplifier 342 is connected via a resistor 350 to a positive voltage supply and via a line 352 to a terminal 353 of a peripheral storage unit (PSU) 354. The terminal 353 carries a second signal for the test network which is supplied to the analog multiplexer 302 via the buffer amplifiers 342 and 338 and associated circuitry described above and via the line 308. This second signal is developed by the central processing circuit 194 as will be described below and may be of a frequency, for example, on the order of 2 megahertz.

The PSU 354 also has outputs on lines 356 and 358 connected to control inputs of the multiplexer 302 for selecting either the signal on line 306 or that on line 308 as the output of the multiplexer 302 on the line 360. The signal selected as the output on line 360 is connected via a capacitor 362 to an input of a buffer-driver s364, the input also being connected via a resistor 366 to ground and the output thereof being connected to the terminal 206, the input terminal of the test cell circuits of FIG. 8, as described above. The lines 356 and 358 are OR-ed via diodes 368 and 370 to a line 372 which is also connected via a resistor 374 to a positive voltage supply. The line 372 comprises another input line to the multiplexer 302 and is connected via an inverter 376 to yet another input line 378 of the multiplexer 302. The lines 372 and 378 comprise control inputs to the multiplexer 302 for selecting as an output thereof on a line 380 either the signal on the line 300 which corresponds to the temperature signal at the terminal 204 or the signal on the line 304 which corresponds to the peak detector signal at the terminal 254.

The line 380 is connected to an input of a voltage-to-frequency converter 382. The conversion factor of the voltage-to-frequency converter 382 is set by a variable resistor 384 connected thereto by a resistor 386 via the line 388. This factor may be, for example, on the order of 20 kilohertz/volt. The voltage-to-frequency converter 382 has its output on line 390 connected to one input of a two input NOR gate 394 and via a resistor 392 to a positive voltage supply. Thus, the voltage-to-frequency converter 382 produces an output signal on line 390 whose frequency is proportional to the voltage of the signal on line 380. The NOR gate 394 has its output on a line 396 connected to one input of a two input NOR gate 398.

The weight signal at terminal 290 is connected via a line 400 to an input of a divider circuit 402 which divides the frequency thereof to a suitable value for the following stages to receive. The divider 402 may be, by way of example, a divide-by-ten divider circuit. The divider 402 has an output on the line 404 connected to one input of a two input NOR gate 406 whose output is connected to the second input of the two input NOR gate 398. The opposite inputs of the NOR gates 394 and 406 are connected via the lines 408 and 410, respectively, to outputs of the PSU 354 which provide control signals to the gates 394, and 406 to select as the output on line 412 of the gate 398 either the weight signal from the line 404 or the signal on the line 390 which may be either the peak detector or temperature signal, previously selected as described above. The signal thus selected on the line 412 is connected to an input of a 5 decade counter 414 and via a resistor 416 to a positive voltage supply. The 5 decade counter may be of the type designated MC14534 and manufactured by Motorola. The 5 decade counter 414 is connected via lines 418, 420 and 422 at the control inputs thereof to receive appropriate control signals from the PSU 354. Each of the lines 418, 420 and 422 are suitably biased by respective resistors running to a positive voltage supply. The 5 decade counter 414 is adapted to multiplex signals out corresponding to the input signals received on the line 412 thereof in BCD data form on output lines 424, 426, 428 and 430, as controlled by the signals on lines 418, 420 and 422 thereof. The BCD coded data on the lines 424 through 430 are connected via buffers 432, 433, 434 and 435 to four inputs 436, 437, 438 and 439, respectively, of the PSU unit 354. A line 440 from the PSU 354 is connected to one input of a two input NOR gate 442, the other input of which is connected to ground. The output of the NOR gate 442 is connected to the terminal 228 which is connected to the relay 226 of FIG. 8 for selectively connecting the calibration network comprising resistor 220 and capacitors 222 and 224 into the test network for calibration purposes, as described above. The signal applied from the PSU 354 via the line 440 to the NOR gate 442 determines whether the test calibration network will be so connected or will remain out of the network.

The four-by-four button array keyboard 30 is connected to inputs 444 through 451 respectively of a second peripheral storage unit (PSU) 452, inputs 444 through 447 providing a respective row signal for each push button and inputs 448 through 451 providing a respective column signal for each push button whereby the 16 push buttons are identified by signals at the inputs 444 through 451, respectively, by a pair of signals corresponding to the row and column position of each. Similarly, inputs 453 and 454 of the PSU 452 are connected to receive signals from the load-unload switch 32 of FIG. 7 representing the load and unload positions thereof respectively, and input 456 of the PSU 452 is connected to the write button 174 of FIG. 7 to provide a signal therefrom to indicate the actuation thereof. Three additional inputs to the PSU 452 on lines 460, 462 and 464 represent, respectively, the signals from the switches 158, 88 and 77 of FIGS. 2 through 4, thereby providing indication of the test cell being unloaded, the strike off function being completed and the hopper doors being opened, respectively. It will be understood that the respective switches 77, 88, 158 each are provided with suitable connections to a voltage supply (not shown) for providing suitable signals as described. The PSU's 354 and 452 also have corresponding ones of three groups of input/output lines thereof, designated generally 466, 468, and 470, connected in common which are further described hereinbelow. A control line 472 is connected to a control input of the PSU 354 and similarly, a control line from the PSU 354 at terminal 474 thereof is connected to a similar control input terminal 476 of the PSU 452 and a control line exits therefrom to the terminal 478.

Figure 11A:
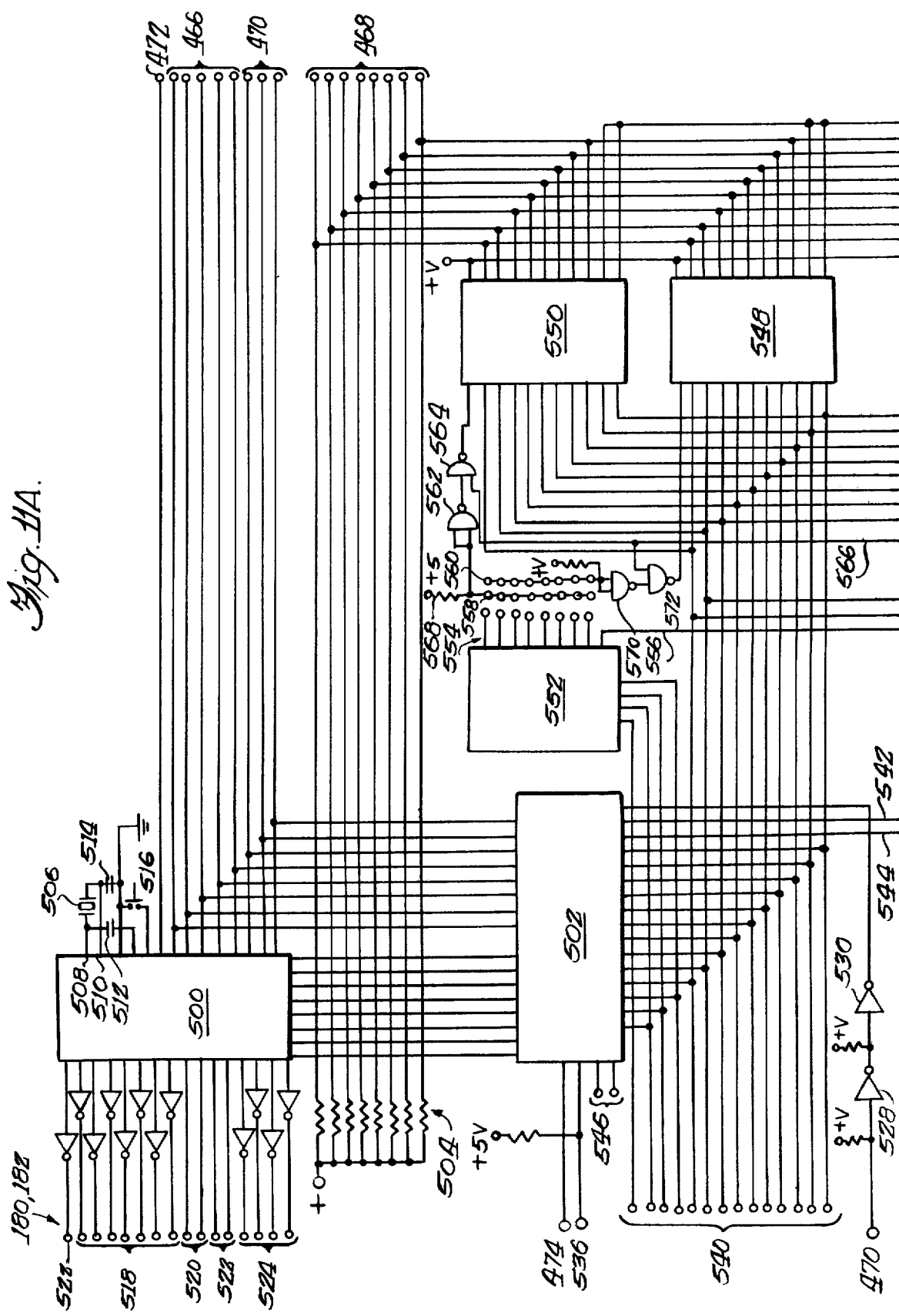
FIGS. 11A and 11B are a detailed schematic diagram of the central processing unit circuits of FIG. 7.
Figure 11B:
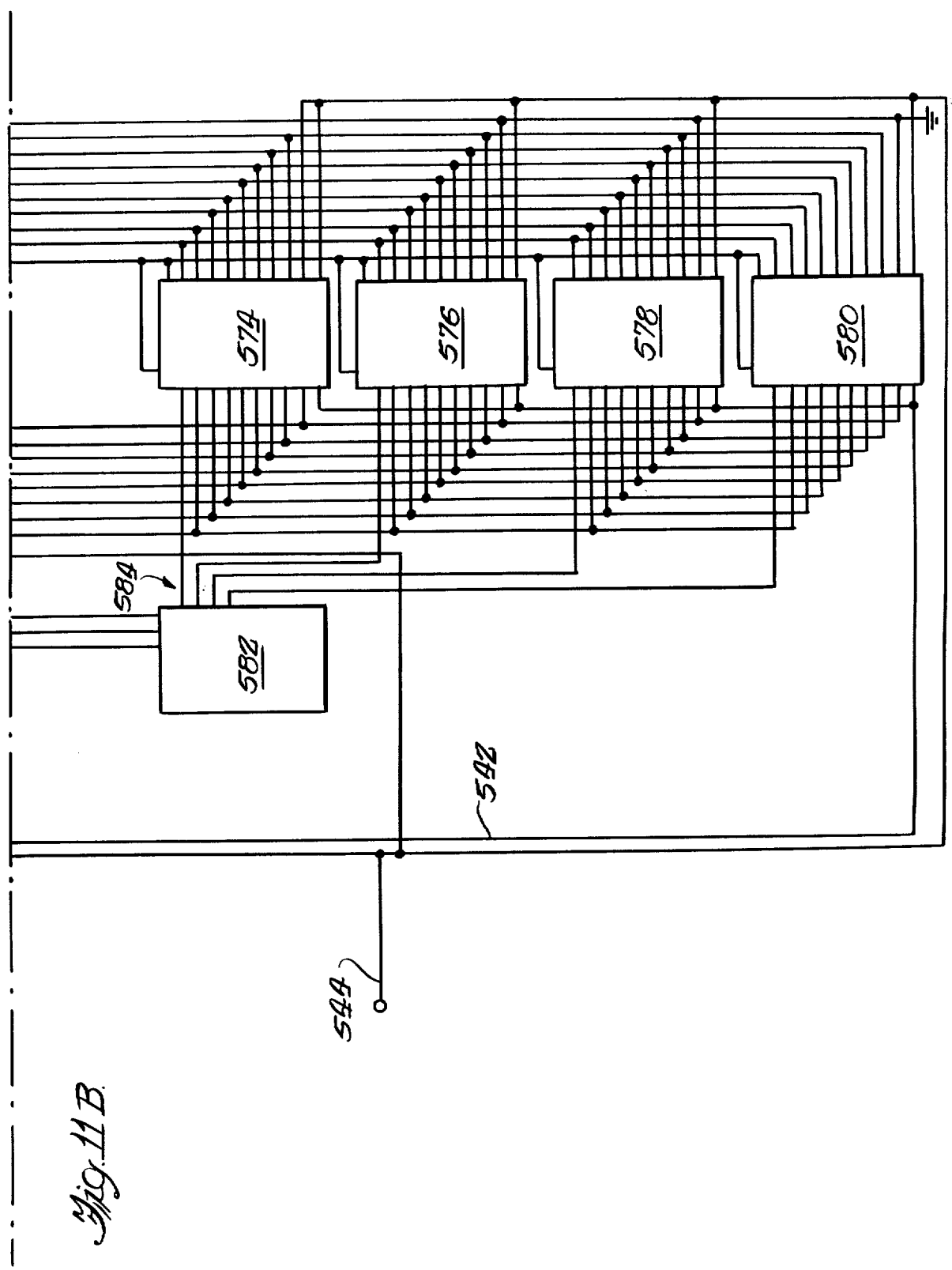

Referring now to FIGS. 11A and 11B, the central processing circuit 194 of FIG. 7 is illustrated in detail. The central processing circuit includes a central processing unit (CPU) 500 which includes control terminals connected to the lines 466, 472 and three of the lines 470 of the peripheral storage unit 354 of FIG. 10A and bidirectional data terminals connected to the lines 468 of the peripheral storage units 354 and 452, of FIGS. 10A and 10B. The lines 468 serve as bidirectional data bus lines for the system. Control signals are transmitted on the lines 466 and 470, which originate in the CPU 500 and control the operation of the respective peripheral storage units 354 and 452 connected thereto. The control lines 466 and 470 and the bidirectional data lines 468 are also connected to corresponding terminals of a static memory interface (SMI) unit 502. The bi-directional data lines 468 are each connected via suitable, pull-up resistors, designated generally 504 to a positive voltage supply. The central processing unit 500 includes an internal oscillator for generating appropriate clock signals for sequencing of overall system functions, via one of the control lines 470. The main clock oscillator frequency is controlled via a crystal element 506 connected at one end thereof to a terminal 508 of the CPU 500 and at the other end thereof to a terminal 510 of the CPU 500. The external connections for the clock oscillator portion thereof are made to suitable external elements such as capacitors 512 and 514, a reset switch 516 and to ground. These connections are made in the manner suitable for setting the frequency of the internal clock oscillator of the CPU 500, to a frequency of substantially two megahertz. The central processing unit 500 includes a plurality of output lines corresponding generally to the connecting lines 180 and 182 the block diagram of FIG. 7 for providing appropriate output signals to the display circuits 178 and printer 184. The individual lines of the display and printer outputs 180, 182 are as follows: the lines 518 carry appropriate signals from the CPU 500 to operate both the display circuits and the printer; the lines 520 carry signals to the display circuits only; the lines 522 and 524 carry signals to the printer only. It will be noted that the lines 518 and 524 each include an inverter-type buffer, designated generally 526 having an input connected to the corresponding terminal of the CPU 500 and an output comprising an individual one of the lines 518 and 524, respectively. The remaining one of the four control lines 470 of the peripheral storage unit 354 of FIG. 10A is connected to an input of the static memory interface 502 via inverters 528 and 530 connected in series and each having a pull-up resistor 532 and 534, respectively, to a positive voltage supply at its respective input. An additional control line 536 is connected to a terminal of the static memory interface 502 and has a pull-up resistor 538 to a positive voltage supply connected thereto. The line 536 receives a suitable control signal from a printer which may be connected externally to the instrument.

The static memory interface (SMI) 502 receives control inputs via the lines 466 and 470 from the central processing unit 500 and is adapted to receive and transmit data to and from the central processing unit 500 via the data bus lines 468. The SMI 502 is adapted to provide an appropriate data interface between the central processing unit 500 and the 8-bit data output thereof connected on the data bus lines 468, and memory devices to be described below. The static memory interface 502 is provided with 16 address lines, designated generally 540 and 546 to address the memory devices and with control lines 542 and 544 to provide suitable control signals for the memory devices in response to control signals from the CPU 500 via the lines 466 and 470. In the embodiment shown for purposes of illustrating the invention, the two address lines designated generally 546 are not used.

Suitably wired sockets 548 and 550 are provided for inserting read-only memory devices of 1024 by 8 bit configuration and preferably of the ultra-violet erasable and electrically programmable type. Suitable memory devices may optionally be installed in the sockets 548 and 550 to accommodate additional read-only memory as will be explained in detail hereinbelow. Suffice it to say that the sockets 548 and 550 have a plurality of bi-directional data input/output lines connected in common with corresponding ones of the data bus lines 468 and 10 address lines connected in common with corresponding ones of the last ten of the address lines 540 of the static memory interface 502.

A decoder 552 is provided including four inputs connected to the first four of the address lines 540 of the static memory interface 502. The decoder 552 is adapted to receive address signals from the static memory interface and decode them onto eight outputs thereof designated generally 554 and a ninth output 556 thereof. The eight outputs 554 of the decoder 552 are selectively connectable to one or both of two groups of corresponding terminals connected along two lines designated generally 558 and 560 which are connected to appropriate logic for selecting one of the memory devices which may be optionally inserted in the sockets 548 and 550 as described above, to be addressed by the address lines 540 of the static memory interface 502. The line 558 is connected to both inputs of a two input NAND gate 562 whose output is connected to one input of a two input NAND gate 564 whose output is connected to a chip select input of the socket 550. The opposite input of the NAND gate 564 is connected via a line 566 to the control line 544 from the static memory interface 502. A pull-up resistor 568 to a positive voltage supply is also connected to the line 558. Similarly, the line 560 is connected to a pull-up resistor to a positive voltage supply and to the two inputs of a two input NAND gate 570. The output of the NAND gate 570 is connected to one input of a two input NAND gate 572 whose output is connected to the chip select terminal of the socket 548. The other input of the NAND gate 572 is also connected to the line 566 from the control line 544 of the SMI 502.

Similarly, four sockets 574, 576, 578 and 580 are provided for accommodating up to four random access memories of 256 by 8-bit configuration, which may be inserted to provide additional random access memory capacity. The sockets 574, 576, 578 and 580 are provided with connections to a suitable positive voltage supply, bi-directional data lines connecting corresponding data input/output terminals thereof with the data bus lines 468, and connections to the control lines 542 and 544 of static memory interface 502. A second decoder 582, substantially identical to the decoder 552 is provided having a first input connected to the line 556 from the output of the decoder 552 and two inputs connected to the first two of the ten address lines 540 from the address inputs of the sockets 548 and 550. The decoder 582 includes four output lines designated generally 584 which are connected to the chip select inputs of the four sockets 574, 576, 578 and 580, respectively. Thus, the decoder 582, in response to signals from the control lines 542 and 544, the line 556 from the decoder 552, and the address lines 540 of the static memory interface 502, is adapted to select and address a random access memory device which may be optionally installed in one of the sockets 574–580 to read and write data therefrom via the system data bus lines 468 connected thereto.

In the instrument according to a preferred embodiment of the present invention, none of the four sockets 574, 576, 578 and 580 are occupied by random access memories (RAM'S). However, in an alternate embodiment, one or more RAM'S may be provided to expand the data handling capacity of the instrument. The aforementioned control and address signals are adapted to effect the storage of data in such random access memories from multiple readings taken across test cell 40 of FIG. 8. Similarly, and under the control of the aforementioned decoder 582 and control lines 542 and 544 of the static memory interface 502, RAM'S in the sockets 574 through 580 transfer data stored therein via the data bus lines 468 to the central processing unit 500, as called for thereby.

Figure 12:
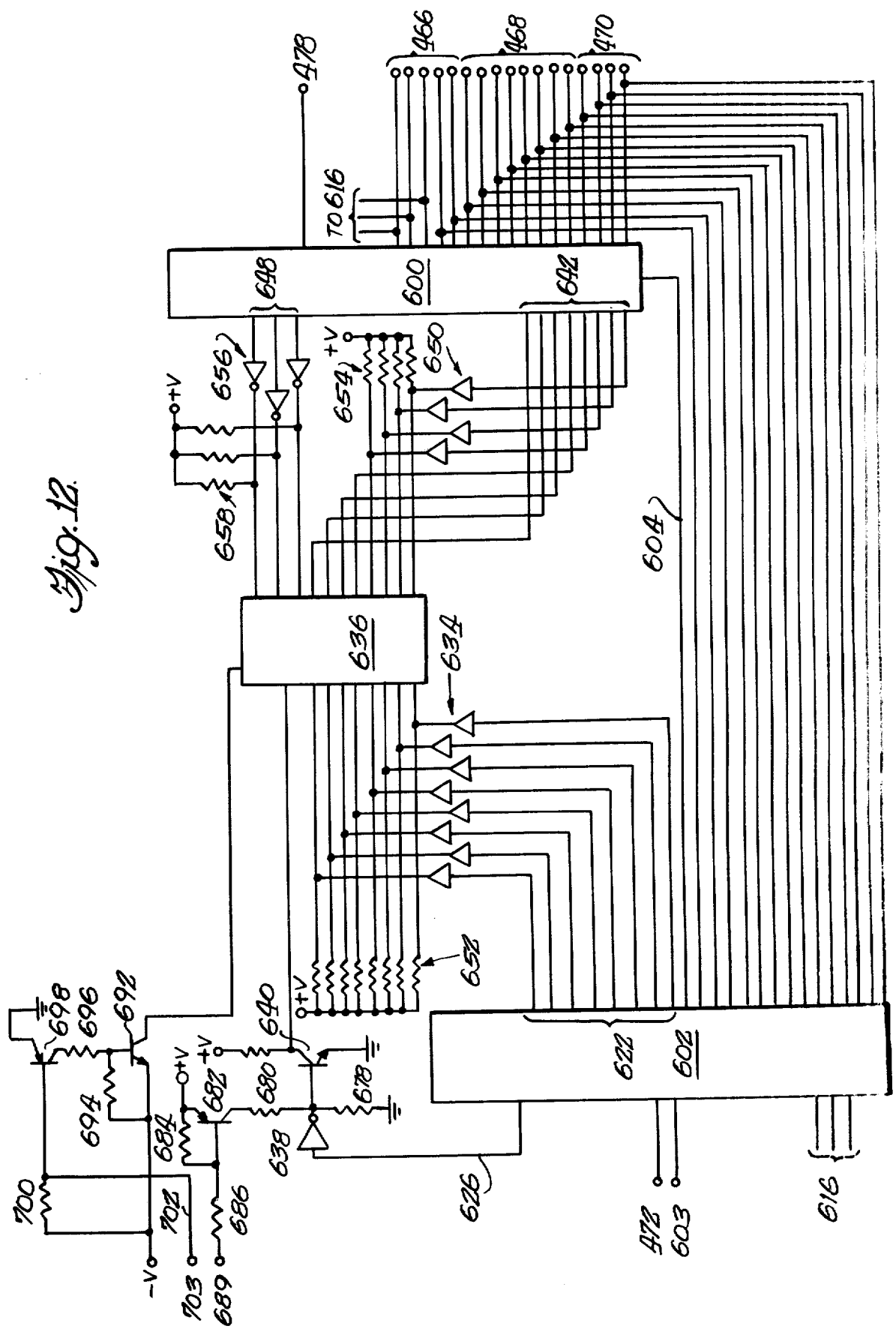
FIGS. 12 and 13 are detailed schematic diagrams of the memory circuits of FIG. 7.

Referring now to FIG. 12 the memory circuits 197 of FIG. 7 are illustrated in detail. Peripheral storage units 600 and 602 are substantially identical to the peripheral storage units 354 and 452 of FIG. 10A hereinbefore described. The peripheral storage units 600 and 602 include inputs from the control lines 466 and 470 to receive control signals from the central processing unit 500 of FIG. 11A and are also provided with input/output terminals connected to the data bus lines 468. It will be noted that the PSU 602 is connected via lines 616 to three of the lines 466. The peripheral storage units 600 and 602 each include an additional control input at terminals 478, 472, respectively, which are the same as the like numbered terminals of FIG. 10A. It will be noted that the signals on a terminal 603 of the PSU 602 correspond to the signals on a common line of the keyboard 30 and control switches 32 and 34 of FIG. 7, respectively, for providing a suitable indication of the operation thereof to the peripheral storage unit 602 which is adapted to provide a suitable control signal in response thereto. A line 604 connects a control terminal of the PSU 600 to a similar terminal of the PSU 602 to carry suitable control signals therebetween.

The peripheral storage unit 602 includes eight terminals designated 622 connected as address lines to a memory chip 636 via eight buffers, designated generally 634. A line 626 is connected as a chip select line to the memory chip 636 via an inverter 638 connected to the base electrode of a transistor 640 whose collector electrode is connected to the chip select input of the memory chip 636. The memory chip 636 preferably comprises an electrically erasable and programmable read-only memory of 256 by 4-bit configuration. The peripheral storage unit 600 includes four input and four output lines designated generally 642, which are connected as data lines to the data input and output terminals of the memory chip 636. The lower four data input lines 642 are connected to the memory chip 636 via suitable buffers designated generally 650. The buffers 634 and 650 are provided with suitable pullups to a positive voltage supply comprising resistors designated generally 652 and 654, respectively. Suitable control signals are also provided to the memory chip 636 via lines 648 of the PSU 600 which are connected to suitable control inputs of the memory chip 636 via three inverter-type buffers, designated generally 656. The buffers 656 are provided with suitable pull-ups to a positive voltage supply comprising resistors 658. Protection is provided for the chip select input of the memory chip 636 from the transients during power up/down switching by the transistor 640 and associated elements. The base electrode of the transistor 640 is connected via a resistor 678 to ground and via a resistor 680 to the collector terminal of a PNP transistor 682. The emitter terminal of the transistor 682 is connected to a positive voltage supply and is connected via a resistor 684 to the base electrode thereof. The base electrode of the transistor 682 is connected via a resistor 686 to a terminal 689 to receive a suitable signal from a power up/down sensing circuit, to be described below to protect the chip select input of the memory chip 636 during power switching. A voltage supply terminal 690 of the chip 636 is also protected during power on/off switching by a transistor 692 and associated elements. The collector electrode of the transistor 692 is connected to the power supply input 690 and the emitter electrode thereof is connected to a negative voltage supply and via a resistor 694 to the base electrode thereof. The base electrode of the transistor 692 is connected via a resistor 696 to the collector electrode of a PNP transistor 698 whose emitter electrode is connected to ground. The base electrode of the transistor 698 is connected via a resistor 700 to a negative voltage supply and via a line 702 connected to a terminal 703 to receive an appropriate signal from the aforementioned power up/down sensing circuits to protect the power supply input 690 of the chip 636 from transients during power on/off switching. The memory circuit of FIG. 12 is adapted to provide storage for a sufficient number of constants for the instrument to calculate the moisture content of a plurality of different materials. It will be noted that the peripheral storage units 600 and 602 are substantially identical to the peripheral storage units 354 and 452 of FIGS. 10A and 10B.

The central processing unit 500 and static memory interface 502 of FIG. 11 together with the peripheral storage units 354 and 452 of FIG. 10A and the peripheral storage units 600 and 602 of FIG. 12 comprise the basic units of a microprocessor, preferably of the type generally designated F8 and manufactured by Fairchild. The central processing unit 500 preferably comprises an integrated circuit of the type generally designated 3850 and manufactured by Fairchild. Similarly, the peripheral storage units 354, 452, 600 and 602 preferably comprise integrated circuits of the type designated 3851 and manufactured by Fairchild and the static memory interface 502 comprises an integrated circuit of the type designated 3853 and manufactured by Fairchild. The structure and function of these units is described in publications entitled "F8 User's Guide" and "Guide To Programming The F8 Micro Computer", copyright 1976, published by the Fairchild Camera and Instrument Corporation, which are incorporated herein and by reference. Briefly, the central processing unit 500 includes suitable components for directing the carrying out in proper sequence of the measurement taking of the moisture tester via the test cell and temperature sensors and weight sensor of FIGS. 8 and 9, the accumulation of data therefrom and calculation and display of the moisture content of particular materials desired to be measured, in accordance with instructions via the keyboard 30 and switches 32 and 34, and with instructions contained in memory portions of the peripheral storage units 354, 452, 600 and 602. The peripheral storage units 354, 452, 600 and 602 include suitable input/output ports for connection to the other elements and components of the moisture tester as described above, as well as permanent memory storage capacity for the complete set of instructions required by the CPU 500 to control the overall operation of the moisture tester. The CPU 500 includes sufficient random access memory capacity to store measurement data as accumulated from the test cell 40 until the data is used by the CPU 500 to calculate the moisture content of the material being tested. The static memory interface 502 is adapted to provide a suitable interface between the CPU 500 and the optional additional memory devices 574 through 580 of FIG. 11B to store additional measurement data therein as accumulated and to return this data to the CPU 500 as called for to determine other constituents of the material being tested therefrom. Similarly, the input/output ports of the PSU's 600 and 602 are utilized as an interface between the CPU 500 and the memory 636 of FIG. 12 to select and transmit to the CPU 500, data contained thereon as called for by the CPU to perform, together with the measurement data, the necessary calculations to determine the moisture content of the material being tested. The CPU 500 provides suitable control signals to all of the other units of the microprocessor via the control lines 466, 470 and 472, described above, and the data bus lines 468 provide bidirectional lines for the transmission of data selectively throughout the system. It will be noted that the sockets 548 and 550 provided in the circuit of FIG. 16A are adapted to receive additional memory units, as described above to supplement, or otherwise alter as desired, the instructions contained in the PSU's 354, 452, 600 and 602 for overall system operation.

Figure 13:
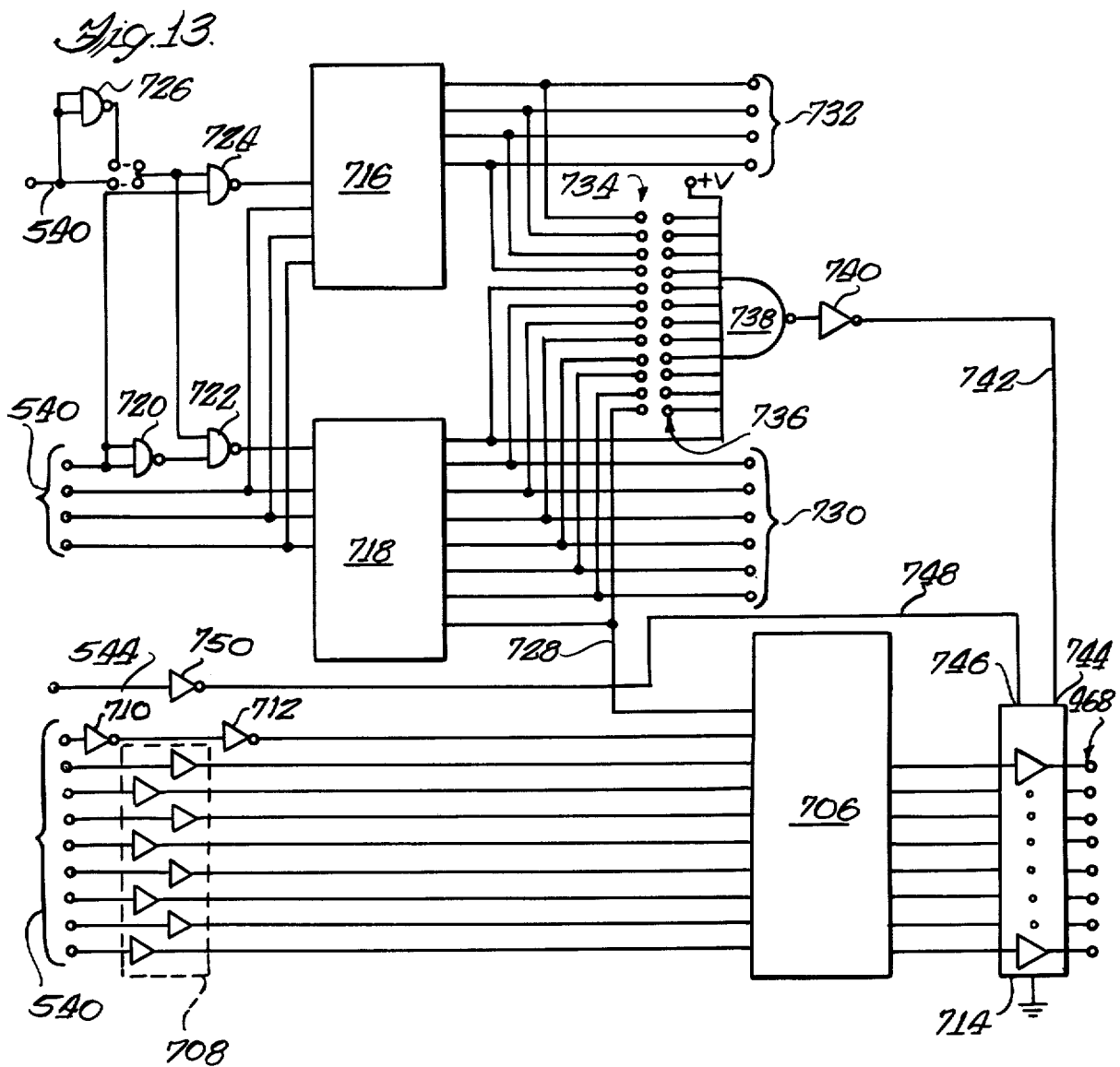

Referring now to FIG. 13, a circuit which may be used in an alternate embodiment of the microprocessor system is illustrated. In the case where it is desirable to provide a set of instructions for the CPU 500 which may be changed or altered as desired, the circuit of FIG. 13 may be employed. In this alternate embodiment, the peripheral storage units 354, 452, 600 and 602 comprise integrated circuits designated 3861 and manufactured by Fairchild rather than the circuits designated 3851 of the preferred embodiment. All external terminals and connections with other elements thereof remain the same as described above. However, the 3861 integrated circuits serve only as peripheral input/output (PIO) circuits and have no memory elements therein for the storage of instructions for the CPU 500. It will be noted, in this regard, that the instructions stored in the memory elements of the 3851 devices are permanent and unalterable once inserted therein. The circuit of FIG. 13, therefore, provides alternative memory capacity for storing the instructions for the system in alterable form in a plurality of memory chips of the ultra violet erasable and electrically programmable ROM type and preferably of a 512 by 8-bit configuration. One such memory chip 706 is illustrated in FIG. 13, but it will be understood that as many as twelve identical memory chips to the chip 706 may be employed in the circuit of FIG. 13, each chip having its corresponding address lines and data lines connected in common with those of the memory chip 706. The memory chip 706 includes nine address inputs connected to nine of the address lines 540 of the static memory interface 502 of FIG. 11A, eight of which are connected thereto via suitable buffers designated generally 708 and the ninth via a series connected pair of invertertype buffers 710 and 712. Data input/output lines of the memory chip 706 are connected to the data bus lines 468 via suitable buffers designated generally 714 which are preferably tri-state buffers. Suitable chip select logic for selecting either the memory chip 706 or one of up to twelve additional chips which may be included as described above, includes decoders 716 and 718. The decoders 716 and 718 each include three inputs connected to three of the remaining address lines 540 of the static memory interface 502 of FIG. 11A. Fourth inputs of the decoders 716 and 718, respectively, are connected to the remaining two address lines 540 of the SMI 502 of FIG. 11A via appropriate logic comprising two-input NAND gates 720, 722, 724 and 726. The first of the remaining two address lines 540 is connected to both inputs of the two-input NAND gate 720 and to one input of the two input NAND gate 724. The output of the NAND gate 720 is connected to one input of the two input NAND gate 722 whose output is connected to the fourth input of the decoder 718. The second inputs of the NAND gates 772 and 724 are connected in common and may be selectively connected directly to the remaining address line 540 or to the output of the NAND gate 726, both of whose inputs are connected to the remaining address line 540. Which connection is chosen for the second inputs of the NAND gate 722 and 724 is dependent upon how many memory chips such as the memory chip 706 are utilized in the circuit of FIG. 13. The decoder 718 is adapted to selectively select one of up to eight memory chips via output lines 728 and 730 thereof. The output line 728 is connected to the chip select input of the memory chip 706, while the seven output lines designated 730 are selectively connectable to corresponding chip select inputs of up to seven additional memory chips. Similarly, the decoder 716 includes four output lines 732 which are selectively connectable as chip select lines to the chip select inputs of up to four additional memory chips. The twelve chip select lines 728, 730 and 732 are also connected to twelve corresponding terminals designated generally 734 which are in turn selectively connectable to corresponding ones of twelve terminals designate generally 736 which comprise twelve inputs to a 13 input NAND gate 738 whose thirteenth input is connected to a positive voltage supply. One of the terminals 734 is connected to a corresponding one of the terminals 736 for each memory chip to be used in the circuit of FIG. 13. The output of the NAND gate 738 is connected via an inverter 740 and a line 742 to a common control input 744 of the tri-state buffers 714. Similarly, a second control input 746 of the tri-state buffers 714 is connected via a line 748 and an inverter 750 to the control line 544 of the static memory interface 502 of FIG. 11A. The signals received at the input 744 and 746 of the tri-state buffer 714 are suitable for driving a common control line for the individual buffers of the tri-state buffer 714. The tri-state buffer 714 is preferably of the type generally designated 81LS 95.

Figure 14A:
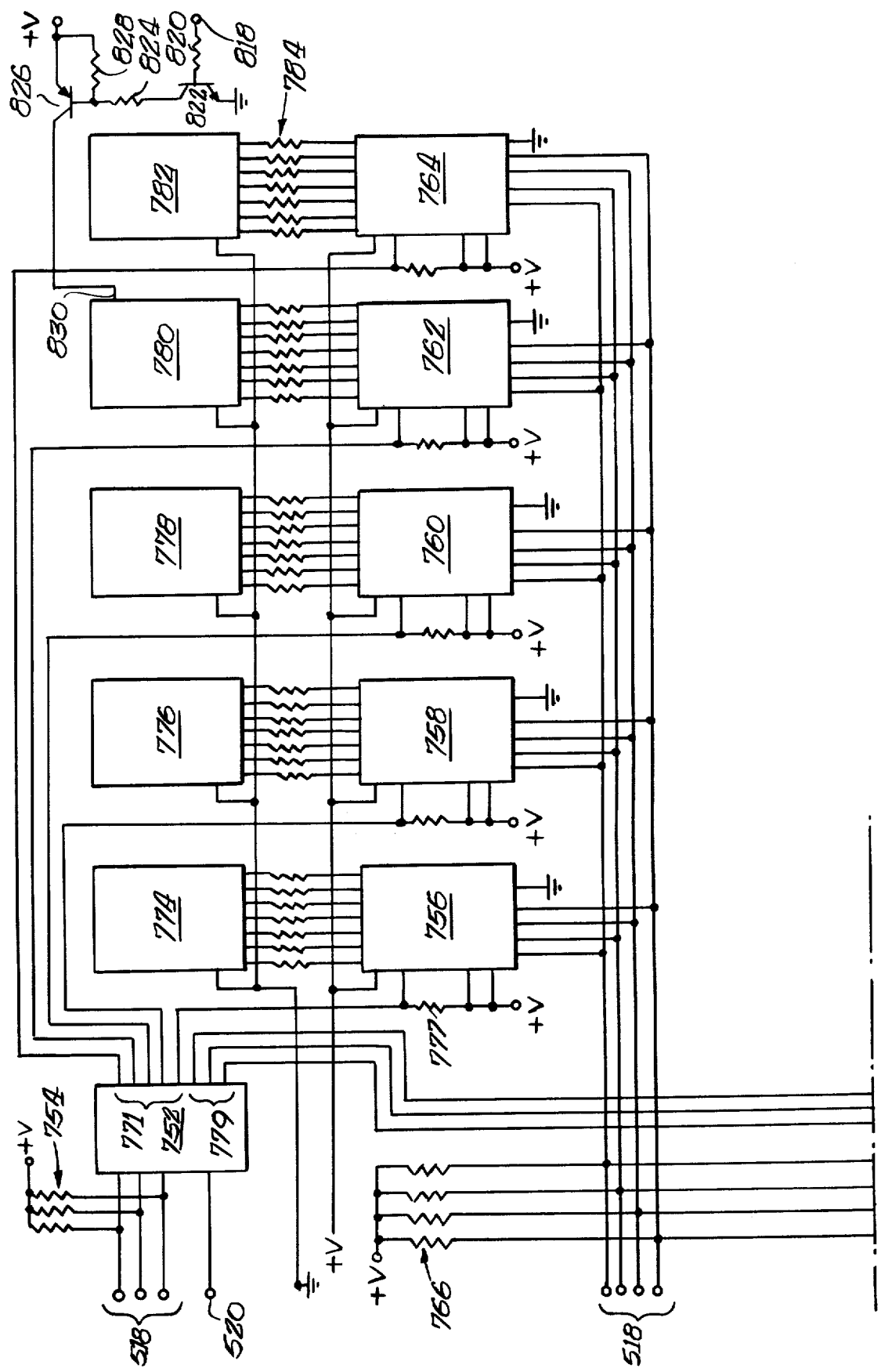

Referring now to FIGS. 14A and 14B, the dipslay circuits 178 of FIG. 7 are illustrated in detail. Three of the seven lines 518 of the central processing unit 500 of FIG. 11A are connected to three inputs of a decoder 752. The three inputs of the decoder 752 are each connected to a suitable pull-up resistor, designated generally 754 to a positive voltage supply. Similarly, the remaining four of the lines 518 from the central processing unit 500 of FIG. 11A, are connected to five latch-decoder-drivers 756, 758, 760, 762 and 764, one of the lines 518 being connected to a corresponding one of four inputs of each latch-decoder-drive. Each of the four lines 518 is similarly provided with a pull-up resistor, designated generally 766 to a positive voltage supply. The four lines 518 connected to the latch-decoder-drivers 756 through 764 are also connected to three latches 768, 770 and 772, each having four inputs, one input of each being connected to a corresponding one of the four lines 518. The decoder 752 includes five output lines, designated generally 771, each of which is connected to a latch enable input of one of the latch-decoder-drivers 756, 758, 760, 762 and 764. Each of the lines 771 is also connected via a suitable resistor 777 to a positive voltage supply. The latch-decoder-drivers 756 through 764 each include suitable connections to a positive voltage supply. Similarly, the decoder 752 includes three lines designated generally 779 connected to the respective enable terminals of the latches 768, 770 and 772. The two control lines 520 of the central processing unit 500 of FIG. 11A are connected to a control input of the decoder 752 and to control inputs of the three latches 768, 770 and 772, respectively. Each of the latch-decoder-drivers 756 through 758 is provided with suitable connections to a corresponding one of five seven-segment numeric displays 774, 776, 778, 780 and 782, via seven suitable current limiting resistors, designated generally 784. Each of the latches 768 and 770 includes eight outputs, designated generally 786 and 788, each of which is connected to an identical circuit, one of which is illustrated: The first one of the eight outputs 786 of the latch 768 is connected via a resistor 790 to the base electrode of a transistor 792 and via a suitable pull-up resistor 794 to a positive voltage supply. The transistor 796 has its emitter electrode connected to ground and a resistor 796 connected between its collector electrode and its emitter electrode. The collector electrode of the transistor 792 is connected to one end of a lamp 798 the other end of which is connected to a positive voltage supply.

Similarly, the latch 772 includes a first output 800 connected via a resistor 802 to the base electrode of a transistor 804 and via a resistor 806 to a positive voltage supply. The transistor 804 has its emitter electrode connected to ground and its collector electrode connected via a resistor 808 to ground. The collector electrode of the transistor 804 is also connected to one side of a lamp 810 whose other side is connected to a positive voltage supply. The latch 772 also includes a pair of outputs 812 and 814 connected to the motor control circuit 168 of FIG. 7 for providing appropriate signals thereto for controlling the operation of the motors 84 and 120, respectively. An output terminal 816 of the latch 772 is connected to a circuit, to be described below, for producing audible signal whenever one of the keys of the keyboard 30 is depressed, to provide a positive indication of the actuation thereof to the operator. An output terminal 818 of the latch 772 is connected to a resistor 820 at the upper right portion of FIG. 14A. The resistor 820 is connected in series from the terminal 818 to the base electrode of a transistor 822 whose emitter electrode is connected to ground. The collector electrode of the transistor 822 is connected via a resistor 824 to the base electrode of a PNP transistor 826. The transistor 826 has its emitter electrode connected to a positive voltage supply, its base electrode connected via a resistor 828 to a positive voltage supply and its collector electrode connected to a terminal 830 of the display element 780.

Figure 18:
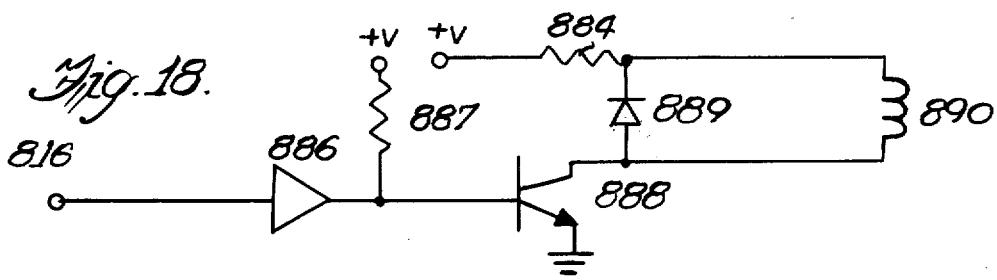
FIGS. 18 and 19 are detailed schematic diagrams of portions of the keyboard circuitry of FIG. 7.
Figure 19:
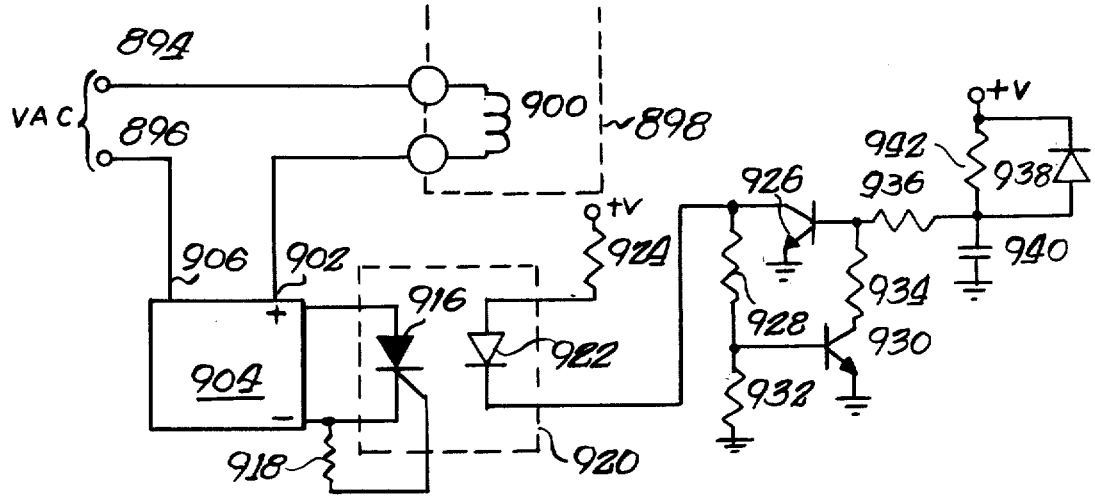

Referring now to FIGS. 18 and 19, the display panel 36 of FIG. 1 is shown in detail and the messages displayed by the several portions thereof are illustrated in tabular form, respectively. The display panel 36 includes the digital display elements 776, 778, 780 and 782 for providing a visual readout of the moisture content of the sample, the sample temperature, the sample density, or the constants stored in the memory of FIG. 12, as selected by operator instructions via the keyboard 30. The display panel 36 also includes the display element 774 for providing a visual, digital identification of a particular group of constants (corresponding to a particular material) selected via the keyboard from the memory of FIG. 12 or providing an error code number for indicating operator errors or any malfunction of the moisture tester. The remaining elements of the display panel 36 comprise a plurality of separate windows including symbols or words which are selectively back lighted by the lamps of FIG. 14B, such as the lamps 798 and 810 illustrated therein. The message window 832 contains a suitable symbol to indicate that the numbers being displayed by the digital display elements 774 through 782 represent a constant stored in the memory of FIG. 12. Similarly, a suitable symbol is included in the window 834 to indicate that an error code is being displayed. The windows 836, 838 and 840 include suitable symbols to indicate that percent moisture, sample temperature, or sample density, respectively, are being displayed by the digits 776–782. The windows 841 through 848 contain suitable messages such as the names of particular commodities or grains to provide visual indication of the identity of the material being tested. The window 850 contains a suitable word or symbol to indicate to the operator that the moisture tester is ready to receive a sample to be tested. The window 852 contains suitable words or symbols to indicate to the operator that data is being collected to update or replace constants stored in the memory of FIG. 12. The window 854 contains words or suitable symbols to indicate to the operator that the limits for which the moisture tester has been calibrated have been exceeded by the test procedure currently in progress. The window 856 contains a suitable word or symbol to indicate to the operator that the moisture tester is currently performing measurements on the sample being tested.

Figure 17:
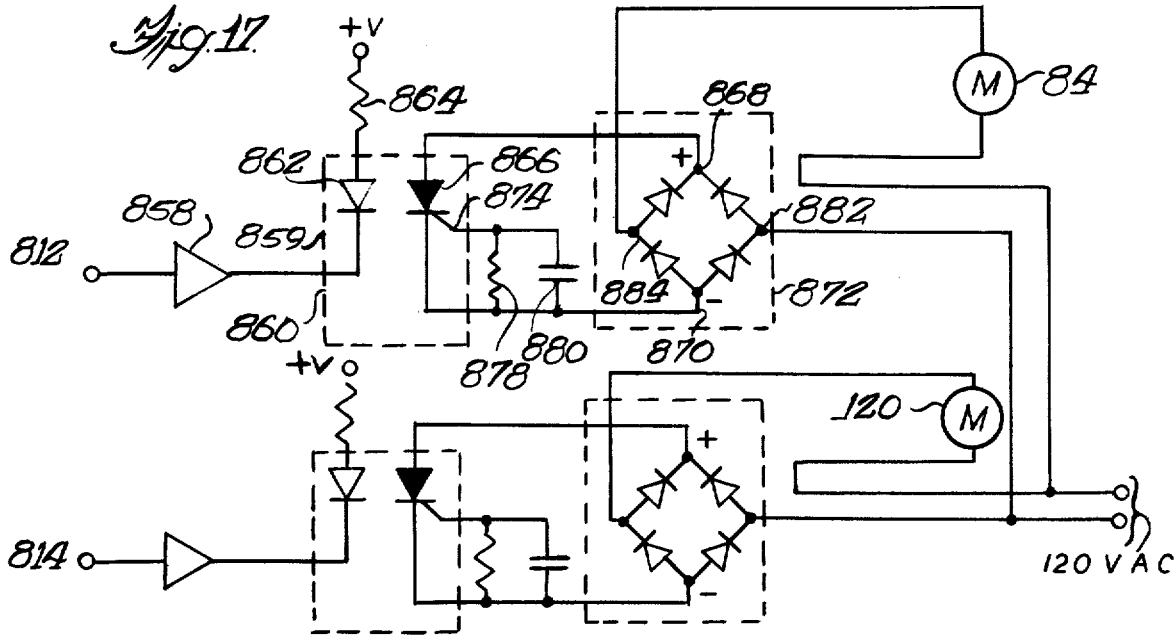
FIG. 17 is a detailed schematic diagram of the motor control circuits of FIG. 7.

Referring now to FIG. 17, the motor control circuits 168 of FIG. 7 are illustrated in detail. It will be noted that the motor control circuits for controlling the motors 84 and 120 in response to control signals developed at the terminals 812 and 814 of FIG. 14B, respectively, are identical. Therefore, only the circuit for controlling a motor 84 will be described in detail. The terminal 812 is connected via a buffer 858 to an input 859 of an opto-isolator 860. The input 859 comprises the cathode of a light emitting diode (LED) 862, whose anode is connected via a resistor 864 to a positive voltage supply. The opto-isolator 860 also includes a photo-responsive silicone controlled rectifier (SCR) 866, whose anode and cathode are connected across a pair of terminals 868 and 870 of a full wave rectifier 872. The gate electrode 874 of the SCR 866 is connected via the parallel combination of a resistor 878 and a capacitor 880 to the terminal 870 of the full wave rectifier 872. The opposite pair of terminals 882 and 884 of the full wave rectifier 872 are connected to one side of a 120 volt AC line, and to one side of the motor 84, respectively. The side of the motor 84 opposite the terminal 884 is connected to the opposite side of the 120 volt AC line. Thus, the motor 84 is turned on and off by the signals developed at the terminal 812 via the buffer 858 and opto-isolator 860, the SCR 866 thereof acting as a switch, as controlled by the LED 862, for current through the full wave rectifier 872 to the motor 84.

Referring now to FIG. 18, a driver circuit for the audible key closure signal is illustrated. The audible keyboard response driver of FIG. 18 includes an input connected to terminal 816 of the latch 772 of FIG. 14B which activates the driver circuit in response to key closures at the inputs 444 through 451 of the PSU 452 of FIG. 10A. The terminal 816 is connected to an input of a buffer 886 whose output is connected to the base electrode of a transistor 888 and via a resistor 887 to a positive voltage supply. The transistor 888 has its emitter electrode connected to ground and its collector electrode connected to the anode of a diode 889 and to one end of a solenoid 890. The diode 889 and solenoid 890 are connected in parallel between the collector of the transistor 888 and a resistor 884 connected in series to a positive voltage supply. Thus, the driver of FIG. 18 converts the signal from the terminal 816 of the latch 772 to a suitable signal to drive the solenoid 890 to produce an audible sound responsive to the closure of a key on the keyboard 30.

Referring now to FIG. 19, a power up/down circuit for providing suitable signals to the terminals 689 and 703 of the memory circuit of FIG. 12 for protecting the memory chip 636 thereof during power on/off switching is illustrated. Terminals 894 and 896 are connected to a suitable source of AC voltage. A relay 898 includes a coil 900 connected between the AC input terminal 894 and one terminal 902 of a full wave rectifier 904 whose terminal 906 is connected to the terminal 896. The relay 898 includes a movable contactor 908. The contactor 908 has one end thereof 912 connected to ground and the other end thereof selectively movable between a normally closed and a normally open position. In the normally closed position the contactor 908 completes a connection between ground and the terminal 703 of FIG. 12, and when the coil 900 of the relay 898 is energized, the contactor 818 is actuated thereby into contact with its normally open terminal which completes a connection between ground and the terminal 689 of FIG. 12. The coil 900 is energized at power on by the AC voltage at the terminals 894 and 896 via the full wave rectifier 904, the passage of current therethrough being controlled by an SCR 916. The anode of the SCR 916 is connected to the positive terminal and the cathode is connected to the negative terminal of the full wave rectifier 904. A resistor 918 connects the gate electrode of the SCR 916 to the cathode electrode thereof. The SCR 916 is a photo-responsive type SCR and forms part of an opto isolator 920, the other portion thereof comprising a light emitting diode (LED) 922 for selectively energizing the photo responsive SCR 916 into conduction. The LED 922 has its anode connected via a resistor 924 to a positive voltage supply which is energized when power is on. The cathode of the LED 922 is connected to the collector electrode of a transistor 926 and via a resistor 928 to the base electrode of a transistor 930. The transistor 930 has its emitter electrode connected to ground, its base electrode connected via a resistor 932 to ground and its collector connected via a resistor 934 to the base electrode of the transistor 926, whose emitter is connected to ground. The base electrode of the transistor 926 is connected via a resistor 936 to the anode of a diode 938 whose cathode is connected to a positive voltage supply, which is energized when the power is on. The anode of the diode 958 is also connected to one side of a capacitor 940 whose other side is connected to ground, and a resistor 942 is connected in parallel with the diode 938. Thus, when the power is switched on, the positive voltage supplies will be energized, whereby the LED 922 will be energized after a delay provided by the capacitor 940 and resistor 942 thereby causing the SCR 916 to go into conduction, completing the current path through the full wave rectifier 904. Therefore, the AC power at the terminals 894 and 896 will be transmitted via the full wave rectifier 904 to the coil 900 for actuating the movable contactor 908 from its normally closed to its normally open position as described above. Similarly, when power is switched off, the relay 898 is immediately deenergized.

For purposes of affording a more complete understanding of the invention, it is advantageous now to provide a brief functional description of the operation thereof.

The keyboard 30 comprises a four-by-four array of switches, as described above. Ten of these switches may be labelled 0 through 9 and arranged in a similar manner to the well-known arrangement of a push button telephone. The remaining six switches may be labelled with appropriate words or symbols to indicate their use, as will be described below.

A grain sample to be tested is first placed in the hopper 24, up to or exceeding the fill line 56 thereof. The moisture tester is now switched on via the on-off switch 34. Once switched on, the moisture tester, under the control of the microprocessor portion thereof, checks the test cell conditions and performs measurements of the weight and temperature of empty test cell as well as the voltage thereacross with each test signal applied. If any difficulty is detected, the error symbol 834 of the display panel 36 is lighted together with a number on the digital display element 774 to identify the difficulty encountered. If the test cell conditions are satisfactory the measurements are stored in memory and the ready message 850 of the display panel 36 is lighted. One of the numbered switches 1 through 8 is now actuated followed by a switch labelled "grain select" to indicate the identity of the grain loaded into the hopper 24 for testing. A corresponding one of the windows 841 through 848 of the display panel 36 is lighted in response thereto to indicate the identity of the grain thus selected. A measurement of the sample material may now be initiated by operating the load switch 32 of the control panel 28. The measuring message 856 of the display panel 36 will now be lighted. Actuation of the load switch 34 will cause the motor 84 to rotate opening the doors 60 and 62 of the hopper 24 to load the sample into the test cell, and operating the strike-off arm 112 to level off the sample at the top of the test cell, as described above. Measurements are made under the control of the measurement and control circuits as described above. If the values of moisture, density or temperature measured for the sample exceed the limits for which the moisture tester is calibrated, the limit exceeded message of the display panel 36 will be lighted. Otherwise, the testing will be completed and data collected therefrom by the microprocessor and associated elements, as described above. Upon completion of the measurement sequence, the calculated percentage of moisture will be displayed on the display panel 36 and the percent moisture symbol 836 thereof lighted.

If the temperature of the sample is desired, a pushbutton of the keyboard 30 appropriately labelled may be operated to cause the temperature to be displayed on the digital display together with the temperature symbol 838 on the display panel 36. Similarly, another pushbutton of the keyboard 30 may be operated to display digits corresponding to the density of the sample as calculated from the measured weight and constant volume, and to light the density symbol 840 of the display panel 36. It will be noted that the microprocessor is programmed to calculate the sample temperature by extrapolation from the empty test cell temperature and the temperature measurement taken substantially ten seconds after loading.

A self-checking function of the moisture tester may be actuated by depressing another pushbutton of the keyboard 30 labelled "self-check" or the like which causes the test network to be connected into the circuit and a reading to be taken thereof in the normal fashion and compared to a check value stored in memory. If the measurement thus taken varies from the check value by a predetermined amount, a failure message such as the error message 834 of the display panel 36 is lighted.

The constants stored in the memory for testing different grains may be reviewed by depressing a numbered pushbutton followed by the "grain select" pushbutton of the keyboard 30 followed by actuation of a number pushbutton of the keyboard 30 to designate the constant to be reviewed and actuation of a "calibration constant" pushbutton of the keyboard 30. The digital display will show one digit to identify the constant thus selected, and digits representing the value of that constant. The constant symbol 832 will also be lighted to indicate that a constant is being displayed.

To place a new constant into the memory requires the above procedure together with entering on the numbered pushbuttons of the keyboard 30 the constant to be entered and operating the write switch 174.

As a specific example, to which no limitation is intended, an exemplary program for the above-described microprocessor is reproduced hereinbelow. This program comprises an assembly language source program:

Funk Case 47A

| Label | Mnemonic | Operand | Comment |
|-------|----------|---------|---------|
| *'    |          |         |         |
| *.    |          |         |         |
| 'MGII' | DI      |         |         |
|       | LIS      | 4       |         |
|       | OUTS     | 5       | Save    |
|       | CLR      |         | Earom first |
|       | OUTS     | 4       |         |
|       | OUTS     | 9       |         |
|       | OUTS     | 0       |         |
|       | OUTS     | 1       |         |
|       | OUT      | H'20'   |         |
|       | OUT      | H'21'   |         |
|       | OUT      | H'25'   |         |
|       | OUTS     | 6       |         |
|       | OUTS     | H'A'    |         |
|       | OUTS     | H'E'    |         |
|       | OUT      | H'22'   |         |
|       | OUT      | H'12'   |         |
|       | LI       | H'16'   |         |
|       | OUT      | H'24'   | Initialize input |
|       | LIS      | 3       | Select  |
|       | OUT      | H'26'   | Start Timer |
|       | OUT      | H'27'   |         |
|       | DCI      | PRLI    |         |
|       | LR       | 0,DC    | Set up Printer |

| Label | Mnemonic | Operand | Comment |
|-------|----------|---------|---------|
|       | LI       | 0'32'   |         |
|       | LR       | 1,A     |         |
|       | PI       | %FR3    |         |
| SRCK  | LIS      | 1       |         |
|       | LR       | 0,A     |         |
|       | PI       | SETUP   | KHZ RC  |
| KRCUP | PI       | CREAD   | Measure |
|       | LISU     | 6       |         |
|       | LIS      | 3       |         |
|       | LR       | 2,A     |         |
|       | PI       | DPADJ   |         |
|       | PI       | ADD     |         |
|       | DCI      | LOUL    | Limit Check |
|       | LIS      | 1       |         |
|       | LR       | 7,A     |         |
|       | PI       | EMTE    |         |
|       | PI       | LIMCK   |         |
| SMRC  | LIS      | 2       |         |
|       | LR       | 0,A     |         |
|       | PI       | SETUP   |         |
| MRCUP | PI       | CREAD   | MHZ RC  |
|       | LISU     | 6       | Reading |
|       | LIS      | 3       |         |
|       | LR       | 2,A     |         |

| Label | Mnemonic | Operand | Comment | Label | Mnemonic | Operand | Comment |
|---|---|---|---|---|---|---|---|
| | LR | A,QU | Interrupt | | PI | DPADJ | |
| | OUTS | H'C' | | | PI | BM6T7 | |
| | LR | A,QL | | STMH | LIS | 3 | MHZ Reading |
| | OUTS | H'D' | | | LR | 0,A | |
| | LISU | 4 | | | PI | SETUP | |
| | LISL | 2 | | MHUP | PI | CREAD | |
| | LI | H'1F' | | | LISU | 6 | |
| | LR | S,A | | | LIS | 3 | |
| | PI | DCLRAL | Initialize Status: | | LR | 2,A | |
| | LI | H'40' | Busy | | PI | DPADJ | |
| | LR | 8,A | | | LISL | 7 | |
| | PI | BCLR | | | LI | H'13' | |
| | LISU | 4 | | | LR | S,A | |
| | LISL | 6 | | | LI | 0'66' | |
| | CLR | | | | LR | 0,A | |
| | LR | I,A | Zero Date | | LI | 0'35' | |
| | LR | I,A | | | LR | 1,A | |
| | LISU | 7 | | | PI | XFR3 | |
| | LR | I,A | | | PI | ADD | |
| | LR | S,A | | | DCI | HIUL | |
| | JMP | DUMP | Dump Cell and | | LIS | 1 | |
| * | | | Start Measuring | | LR | 7,A | |
| * | | | | | PI | BM7T6 | |
| STKH | CLR | | | | PI | LIMCK | |
| | LR | 0,A | | STWT | LIS | 4 | |
| | PI | SETUP | Setup for KHZ | | LR | 0,A | |
| KHUP | PI | CREAD | Measure | | PI | SETUP | |
| | LISU | 6 | | WAUP | LISU | 6 | Read EC Weight |
| | LIS | 3 | | | LISL | 7 | |
| | LR | 2,A | | | CLR | | |
| | PI | DPADJ | Shift to DP = 3 | | LR | D,A | |
| | PI | BM6T7 | | | PI | DGIN | |
| | LISL | 7 | | | LI | 0'66' | |
| | LI | H'13' | | | LR | 0,A | |
| | LR | S,A | | | LI | 0'22' | |
| | LI | 0'66' | | | LR | 1,A | |
| | LR | 0,A | | | PI | XFR3 | Save Weight |
| | | | | | LI | H'C0' | Counts |
| | | | | | LR | 6,A | IN 20-22 |
| | | | | | LISU | 7 | |
| | LISL | 4 | | | NI | H'68' | |
| | CLR | | | | OI | H'10' | |
| | LR | I,A | | | LR | 8,A | |
| | PI | ERDI | | | JMP | STKH | |
| | LISL | 7 | Check Against | LDS1 | LR | A,8 | |
| | LI | H'10' | Original EC | | NI | H'60' | |
| | LR | S,A | Weight in Earom | | OI | H'41' | |
| | PI | ADD | | | LR | 8,A | |
| | LISU | 7 | | | PI | DCLRAL | |
| | LISL | 7 | | | PI | BCLR | |
| | LIS | H'F' | | DOPN | PI | SMON | Open Doors |
| | NS | S | | | CLR | | |
| | LR | S,A | | | LR | 0,A | |
| | PI | BM7T6 | | | LR | 1,A | |
| | DCI | WTUL | | DRCK | IN | H'21' | |
| | LIS | 2 | | | SL | 4 | |
| | LR | 7,A | | | BM | OPEN | |
| | PI | LIMCK | | | DS | 0 | |
| | LR | A,8 | | | BNZ | DRCK | |
| | OI | 8 | | | DS | 1 | |
| | NI | H'EF' | | | BNZ | DRCK | |
| | LR | 8,A | | STER | PI | SMOF | |
| | PI | BCLR | | | LIS | 7 | |
| | LIS | 2 | | | LR | 0,A | |
| | NS | 8 | Done with EC | | JMP | ERROR | |
| | BNZ | LOAD | Update Load | OPEN | PI | SMOF | |
| | JMP | STKH | If Set, Other- | | LIS | 4 | |
| LOAD | LISU | 3 | wise Repeat EC | | NS | 8 | |
| | LISL | 7 | Reading | | BZ | OPN | |
| | CLR | | | | JMP | CLEN | |
| | LR | S,A | | OPN | PI | SMTM | |
| | PI | DCLR | | | PI | SMON | |
| | LIS | 5 | | | LR | 0,A | |

| Label | Mnemonic | Operand | Comment | Label | Mnemonic | Operand | Comment |
|---|---|---|---|---|---|---|---|
| | LR | 0,A | | | LR | 1,A | |
| | PI | CTRS | | STRK | INS | 4 | |
| | PI | SMTM | Read EC Temp | | IN | H'21' | |
| TPUP | LISU | 6 | | | NI | H'10' | |
| | LISL | 6 | | | BNZ | STKD | |
| | PI | DGIN | | | DS | 0 | |
| | PI | TEMP | | | BNZ | STRK | |
| | LI | 0'76' | | | DS | 1 | |
| | LR | 0,A | | | BNZ | STRK | |
| | LI | 0'25' | | | BR | STER | |
| | LR | 1,A | | STKD | PI | SMOF | |
| | PI | XFR3 | | STLP | INS | 4 | |
| | PI | BM7T6 | | | INS | 4 | |
| | DCI | TPUL | | | INS | 4 | |
| | LIS | 3 | | | DS | 2 | |
| | LR | 7,A | | | DS | 0 | |
| | PI | LIMCK | Check Ambient | | BNZ | STLP | |
| | LI | H'20' | Temp Against | | DS | 1 | |
| | NS | 8 | Limits | | BNZ | STLP | |
| | BNZ | LDS1 | | | CLR | | |
| | PI | CKSUM | If not Cal Data | | LR | 0,A | |
| | BZ | LDS1 | Mode, Do Check- | | PI | CTRS | KHZ Sample |
| | PI | DCLRAL | sum on K's | | PI | SMTM | Reading |
| | LIS | 5 | | | LISU | 4 | |
| | LR | 0,A | | | LISL | 5 | |
| | PI | CCOF | | | PI | DGIN | Save KHZ Counts |
| | LI | H'69' | | | LIS | 3 | @ 43-45 |
| | OUTS | 1 | Checksum Error; | | LR | 0,A | |
| | PI | NABL | Flag and try | | PI | CTRS | MHZ Sample |
| | PI | DSHT | Again | | PI | SMTM | Reading |
| | LR | A,8 | | | LISU | 5 | |
| | LISL | 2 | | | LR | S,A | |
| | PI | DGIN | Save MHZ Counts | | PI | ADD | Compute |
| | LIS | 4 | @ 50-52 | | PI | BM7T6 | Sample EC |
| | LR | 0,A | | | LR | A,8 | Temp |
| | PI | CTRS | | | NI | H'20' | Difference |
| | LIS | 8 | Setup for Weight | | BNZ | TMPCD | |
| | LR | 0,A | | | PI | CCPT | |
| | LI | H'9B' | | | LR | A,6 | |
| | LR | 1,A | | | AI | H'18' | |
| | LI | H'9B' | | | LR | 6,A | |
| | LR | 2,A | | | LISU | 5 | |
| LDLY | DS | 2 | | | LISL | 5 | |
| | BNZ | LDLY | | | PI | ERDI | |
| | DS | 1 | | | BR | TMPE | |
| | BNZ | LDLY | | TMPCD | LISU | 5 | |
| | DS | 0 | 5 Second Delay | | LISL | 6 | |
| | BNZ | LDLY | For Weight | | LI | H'20' | |
| | LISU | 6 | Counting | | LR | S,A | |
| | LISL | 6 | | TMPE | LISL | 4 | |
| | PI | DGIN | | | CLR | | |
| | LISL | 7 | | | LR | 1,A | |
| | LI | H'12' | | | LR | 1,A | |
| | LR | S,A | | | LISL | 7 | |
| | LIS | 2 | | | LIS | 1 | |
| | LISU | 7 | | | LR | S,A | |
| | LR | S,A | Subtract From | | PI | MPY | MPY Diff by |
| | LI | 0'22' | EC Counts | | LR | A,8 | Extrapolation K |
| | LR | 0,A | | | NI | H'20' | |
| | LI | 0'76' | | | BNZ | TDOK | |
| | LR | 1,A | | | LIS | 3 | |
| | PI | XFR3 | | | LR | 2,A | |
| | PI | ADD | | | LISU | 6 | |
| | LIS | 2 | | | PI | DFADJ | |
| | LR | 2,A | | | LISL | 6 | |
| | LISU | 7 | Set DP to 2; | | LR | A,S | |
| | PI | DFADJ | Save in 20-22 | | CI | H'20' | |
| | LI | 0'76' | | | BP | TDOK | |
| | LR | 0,A | | | LIS | 4 | Flag Error |
| | LI | 0'22' | | | LR | 0,A | If Diff>20 |
| | LR | 1,A | | | PI | ERROR | |
| | PI | XFR3 | | TDOK | LISU | 7 | |

| Label | Mnemonic | Operand | Comment |
|---|---|---|---|
|  | PI | SMTM | Wait Rest of |
|  | PI | SMTM | 10 Sec |
|  | PI | SMTM |  |
|  | LIS | 5 |  |
|  | LR | 0,A |  |
|  | PI | CTRS |  |
|  | PI | SMTM | Take Sample Temp |
|  | LISU | 6 |  |
|  | LISL | 6 |  |
|  | PI | DGIN |  |
|  | PI | TEMP |  |
|  | LISU | 7 |  |
|  | LISL | 4 |  |
|  | CLR |  |  |
|  | LR | S,A |  |
|  | LI | O'25' |  |
|  | LR | 0,A |  |
|  | LI | O'66' |  |
|  | LR | 1,A |  |
|  | PI | XFR3 |  |
|  | LISU | 6 |  |
|  | LISL | 7 |  |
|  | LI | H'14' |  |
|  | LI | O'73' |  |
|  | LR | 1,A |  |
|  | PI | XFR2 |  |
|  | LISU | 6 |  |
|  | LISL | 4 |  |
|  | CLR |  |  |
|  | LR | 1,A |  |
|  | LR | 1,A |  |
|  | LI | H'25' |  |
|  | LR | 1,A |  |
|  | LI | H'12' |  |
|  | LR | S,A |  |
|  | PI | ADD |  |
|  | LIS | 4 |  |
|  | LR | 2,A |  |
|  | LISU | 7 |  |
|  | PI | DPADJ |  |
|  | LI | O'77' |  |
|  | LR | 0,A |  |
|  | LI | O'26' | Save T WRT in 23-26 |
|  | LR | 1,A |  |
|  | PI | XFR4 |  |
|  | LI | O'22' |  |
|  | LR | 0,A |  |
|  | LI | O'56' |  |
|  | LR | 1,A |  |
|  | PI | XFR3 |  |
|  | JMP | JATINT |  |
|  | ORG | H'360' |  |
| TINT | LISU | 2 |  |
|  | LISL | 6 |  |
|  | DS | I |  |
|  | BNZ | TRT | Time out for |
|  | DS | S | Interrupt |
|  | BNZ | TRT |  |
|  | LR | P0,Q |  |
| TRT | EI |  |  |
|  | JMP | KYBD |  |
| JATINT | LISU | 5 |  |
|  | LISL | 7 |  |
|  | LIS | 2 |  |
|  | LR | S,A |  |
|  | LI | H'C4' |  |
|  | LR | 6,A |  |
|  | LISU | 6 |  |
|  | LISL | 4 |  |
|  | CLR |  |  |

| Label | Mnemonic | Operand | Comment |
|---|---|---|---|
|  | LISL | 7 |  |
|  | LIS | 4 |  |
|  | LR | S,A |  |
|  | LI | O'25' |  |
|  | LR | 0,A |  |
|  | LI | O'76' |  |
|  | LR | 1,A |  |
|  | PI | XFR3 |  |
|  | PI | ADD |  |
|  | LIS | 4 |  |
|  | LR | 2,A |  |
|  | LISU | 7 |  |
|  | PI | DPADJ |  |
|  | PI | RND24 |  |
|  | LISU | 7 |  |
|  | LISL | 4 |  |
|  | CLR |  |  |
|  | LR | S,A |  |
|  | LIS | 4 |  |
|  | LR | 2,A |  |
|  | PI | DPADJ |  |
|  | LI | O'76' |  |
|  | LR | 0,A | Save Temp in 72,73 |
|  | LI | O'22' | Save Weight |
|  | LR | 1,A | in 20-22 |
|  | PI | XFR3 |  |
|  | PI | BLOG |  |
|  | LI | O'32' |  |
|  | LR | 0,A |  |
|  | LI | O'76' |  |
|  | LR | 1,A |  |
|  | PI | XFR3 |  |
|  | LISU | 7 |  |
|  | LISL | 7 |  |
|  | LI | H'13' | KHZ Log (Samp) |
|  | LR | S,A | Log (EC) |
|  | PI | ADD |  |
|  | LIS | 3 |  |
|  | LR | 2,A |  |
|  | LISU | 7 |  |
|  | PI | DPADJ |  |
|  | LI | O'76' |  |
|  | LR | 0,A |  |
|  | LI | O'32' |  |
|  | LR | 1,A |  |
|  | PI | XFR3 |  |
|  | LI | O'52' |  |
|  | LR | 0,A |  |
|  | LI | O'45' |  |
|  | LR | 1,A |  |
|  | PI | XFR3 |  |
|  | PI | BLOG |  |
|  | LI | O'35' |  |
|  | LR | 0,A |  |
|  | LI | O'76' |  |
|  | LR | 1,A |  |
|  | PI | XFR3 |  |
|  | LISU | 7 |  |
|  | LISL | 7 |  |
|  | LI | H'13' | Same for MHZ |
|  | LR | S,A |  |
|  | PI | ADD |  |
|  | LIS | 3 |  |
|  | LR | 2,A |  |
|  | LISU | 7 |  |
|  | PI | DPADJ |  |
|  | LI | O'76' |  |
|  | LR | 0,A |  |
|  | LI | O'35' |  |
|  | LR | 1,A |  |
|  | PI | XFR3 |  |

| Label | Mnemonic | Operand | Comment |
|---|---|---|---|
| | LR | I,A | |
| | PI | ERDI | |
| | LISL | 7 | |
| | LIS | 2 | |
| | LR | S,A | |
| | PI | MPY | MPY WT Counts by |
| | LIS | 2 | Scale Slope |
| | LR | 2,A | |
| | LISU | 6 | |
| | PI | DPADJ | |
| | PI | RND24 | |
| | LISU | 7 | |
| | LISL | 4 | |
| | CLR | | |
| | LR | S,A | |
| | LI | O'76' | |
| | LR | 0, A | |
| DA1TDP | LI | O'32' | |
| | LR | 0,A | |
| | LI | O'66' | |
| | LR | 1,A | |
| | PI | XFR3 | LD D1 |
| | LISU | 6 | |
| | LISL | 7 | |
| | LIS | 1 | |
| | LR | S,A | |
| | LISU | 5 | |
| | CLR | | |
| | LR | S,A | |
| | PI | MPY | * |
| | PI | CCPT | |
| | LR | A,6 | |
| | AI | H'10' | |
| | LR | 6,A | |
| | LISU | 5 | |
| | PI | LODK | |
| | PI | MPY | LD K5 |
| | LI | O'35' | * |
| | LR | 0,A | |
| | LI | O'76' | |
| | LR | 1,A | |
| | PI | XFR3 | LD D 2 |
| | LISU | 7 | |
| | LISL | 7 | |
| | LIS | 3 | |
| | LR | S,A | |
| | PI | ADD | + |
| | LIS | 3 | |
| | LR | 2,A | |
| | LISU | 7 | |
| | PI | DPADJ | |
| | LI | O'77' | |
| | LR | 0,A | |
| | LI | O'33' | |
| | LR | 1,A | |
| | PI | XFR4 | STO D2' |
| | PI | CCPT | |
| | LIS | H'C' | |
| | AS | 6 | |
| | LR | 6,A | |
| | LISU | 6 | |
| | PI | LODK | LD K4 |
| | PI | ADD | + |
| | LIS | 3 | |
| | LR | 2,A | |
| | LISU | 7 | |
| | PI | DPADJ | |
| | LI | O'76' | |
| | LR | 0,A | |
| | LI | O'45' | |
| | LR | 1,A | |
| | PI | XFR3 | |

| Label | Mnemonic | Operand | Comment |
|---|---|---|---|
| | LR | A,8 | |
| | NI | H'20' | |
| | BZ | MOCOMP | |
| | JMP | CALDAT | If Cal Dat |
| MOCOMP | LISU | 7 | Skip Moistur |
| | PI | NORM | |
| | PI | BM7T6 | LD D2 |
| | PI | INVB6 | 1/X |
| | LISU | 7 | |
| | LISL | 7 | |
| | LR | A,S | |
| | CI | 3 | |
| | BZ | DA1TDP | |
| | LISU | 5 | |
| | LIS | 1 | |
| | LR | S,A | |
| | LR | 6,A | |
| | PI | LODK | LD K3 |
| | PI | MPY | * |
| | PI | BM6T7 | |
| | PI | CCPT | |
| | LIS | 4 | |
| | AS | 6 | |
| | LR | 6,A | |
| | LISU | 5 | |
| | PI | LODK | LD K2 |
| | LI | O'33' | |
| | LR | 0,A | |
| | LI | O'67' | |
| | LR | 1,A | |
| | PI | XFR4 | LD D2' |
| | LISU | 6 | Divide By |
| | LISL | 7 | 100 |
| | DS | S | |
| | DS | S | |
| | PI | MPY | * |
| | PI | ADD | + |
| | PI | CCPT | |
| | LISU | 6 | |
| | PI | LODK | LD K1 |
| | PI | ADD | + |
| | LI | O'77' | |
| | LR | 0,A | |
| | LI | O'33' | |
| | LR | 1,A | |
| | PI | XFR4 | STO %M(A) |
| | LI | O'22' | |
| | LR | 0,A | |
| | LI | O'66' | |
| | LR | 1,A | |
| | PI | XFR3 | |
| | PI | INVB6 | LD BD(S) |
| | LISU | 6 | 1/X |
| | LISL | 7 | |
| | CLR | | |
| | LR | S,A | |
| | PI | CCPT | |
| | LI | H'14' | |
| | AS | 6 | |
| | LR | 6,A | |
| | LISU | 6 | |
| | LISL | 6 | |
| | PI | ERDI | LD K6 |
| | LISL | 7 | |
| | LIS | 1 | |
| | LR | S,A | |
| | LISL | 4 | |
| | CLR | | |
| | LR | I,A | |
| | LR | I,A | * |
| | PI | MPY | |

| Label | Mnemonic | Operand | Comment | Label | Mnemonic | Operand | Comment |
|---|---|---|---|---|---|---|---|
| | PI | BLOG | LOG | | LISU | 6 | |
| | LISU | 6 | | | LIS | 1 | |
| | LISL | 7 | | | LR | 2,A | |
| | DS | S | | | PI | DPADJ | |
| | DS | S | | | BC | WTERR | Look at |
| | PI | CCPT | | | LISL | 6 | BD(AV)/BD(S) |
| | LISU | 5 | | | LR | A,S | Check For |
| | LIS | 8 | | | CI | H'11' | >1.2 or <.8 |
| | AS | 6 | | | BM | WTERR | |
| | CI | 7 | | | | | |
| | BM | WTOK | | | LIS | 5 | |
| WTERR | LISU | 3 | | | LR | S,A | |
| | LISL | 7 | | | LIS | 2 | |
| | LR | A,S | Set LIM EX BIT | | LR | 2,A | |
| | OI | 4 | | | LISU | 7 | |
| | LR | S,A | | | PI | DPADJ | |
| WTOK | LI | O'33' | | | LI | O'76' | |
| | LR | O,A | | | LR | O,A | |
| | LI | O'57' | | | LI | O'31' | |
| | LR | 1,A | | | LR | 1,A | |
| | PI | XFR4 | LD %M(A) | | PI | XFR2 | STO %M |
| | PI | MPY | * | | LISU | 6 | |
| | LI | O'67' | | | LIS | 2 | |
| | LR | O,A | | | LR | 2,A | |
| | LI | O'33' | | | PI | DPADJ | |
| | LR | 1,A | | | BC | PERERR | |
| | PI | XFR4 | STO %M(25) | | PI | CCPT | |
| | LI | O'26' | | | LI | H'14' | |
| | LR | O,A | | | AS | 6 | |
| | LI | O'57' | | | LR | 6,A | |
| | LR | 1,A | | | LISU | 0 | |
| | PI | XFR4 | LD T WRT 25 | | LISL | 0 | |
| | LISU | 5 | | | PI | ERDI | |
| | PI | NORM | | | LISU | 6 | |
| | PI | CCPT | | | LISL | 5 | |
| | LI | H'18' | | | DCI | PERUL | |
| | AS | 6 | | | LR | A,1 | Check % |
| | LR | 6,A | | | SR | 4 | Limits |
| | LISU | 6 | | | ADC | | |
| | LISL | 5 | | | LR | A,S | |
| | PI | ERDI | LD K7 | | CM | | |
| | LISL | 4 | | | BM | PERERR | |
| | CLR | | | | DCI | PERLL | |
| | LR | S,A | | | LIS | H'F' | |
| | LISL | 6 | | | NS | 1 | |
| | LR | 1,A | | | ADC | | |
| | LI | H'11' | | | LR | A,S | |
| | LR | S,A | | | INC | | |
| | PI | MPY | | | CM | | |
| | LISU | 7 | | | BM | PEROK | |
| | LISL | 4 | | PERERR | LISU | 3 | |
| | CLR | | | | LISL | 7 | |
| | LR | 1,A | | | LR | A,S | |
| | LR | 1,A | LD #'1' | | OI | 2 | |
| | LI | H'10' | | | LR | S,A | Set LIM EX |
| | LR | 1,A | | PEROK | PI | PRST | BIT FOR %M |
| | SR | 4 | | | BNZ | DSPER | |
| | LR | S,A | | | LISU | 3 | |
| | PI | ADD | + | | LISL | 7 | |
| | PI | BM7T6 | | | CLR | | |
| | LI | O'33' | | | AS | S | |
| | LR | O,A | | | BNZ | DSPER | |
| | LI | O'57' | | | JMP | PRPER | |
| | LR | 1,A | | DSPER | LI | H'70' | |
| | PI | XFR4 | | | OUTS | 1 | |
| | PI | MPY | LD %M(25) | | PI | NABL | |
| | LIS | 3 | * | | LISU | 3 | |
| | LR | 2,A | | | LISL | 7 | |
| | LISU | 6 | | | LIS | 7 | Display Readings |
| | PI | DPADJ | | | NS | S | |
| | PI | PND24 | | | BZ | NOIS | |
| | LISU | 7 | | | LI | H'6F' | |
| | LISL | 7 | | | OUTS | 1 | |
| | | | | | PI | NABL | |

| Label | Mnemonic | Operand | Comment | Label | Mnemonic | Operand | Comment |
|---|---|---|---|---|---|---|---|
| | LIS | 2 | | | NI | 3 | |
| | NS | S | | | BZ | SIQ | |
| | BNZ | MOIS | | | CI | 2 | |
| | LIS | 4 | | | BNZ | SIC | |
| | NS | S | | | LR | A,8 | |
| | BNZ | WEIGHT | | | OI | 2 | |
| | BR | TEMPER | | | LR | S,A | |
| MOIS | PI | ALOFF | | SIC | JMP | DUMP | |
| | PI | LIDP | | PRPER | PI | PRBK | |
| | LI | H'6B' | | | PI | PRBK | |
| | OUTS | 1 | | | PI | PRBL | |
| | PI | NABL | | | DCI | ELNM1 | |
| | LISU | 3 | | | PI | PRMS | |
| | LISL | 7 | | | PI | PRLN | |
| | LIS | 2 | | | PI | PRBL | |
| | NS | S | | | DCI | ELNM2 | |
| | BZ | MONOR | | | PI | PRMS | |
| | PI | LERLT | | | PI | PRLN | |
| MONOR | DCI | RMOIS | | | PI | PRBK | |
| | PI | DSPLY | | | PI | PRDATE | |
| | BR | SIT | | | PI | PRBK | |
| WEIGHT | PI | ALOFF | | | PI | PRGR | |
| | PI | LIDP | | | PI | PRBK | |
| | LI | H'6D' | | | PI | PRBL | |
| | OUTS | 1 | | | LISU | 3 | |
| | PI | NABL | | | LISL | 7 | |
| | LISU | 3 | | | LIS | 2 | |
| | LISL | 7 | | | NS | S | |
| | LIS | 4 | | | BZ | NOPML | |
| | NS | S | | | PI | PRAST | |
| | BZ | WTNOR | | NOPML | DCI | PMOIS | |
| | PI | LERLT | | | PI | PRNUM | |
| WTNOR | DCI | RBULK | | | DCI | PPER | |
| | PI | DSPLY | | | PI | PRMS | |
| | BR | SIT | | | PI | PRLN | |
| TEMPER | PI | ALOFF | | | PI | PRBL | |
| | LI | H'6C' | | | LISU | 3 | |
| | OUTS | 1 | | | LISL | 7 | |
| | PI | NABL | | | LIS | 4 | |
| | LISU | 3 | | | NS | S | |
| | LISL | 7 | | | BZ | NOPWL | |
| | LIS | 1 | | | PI | PRAST | |
| | NS | S | | NOPWL | DCI | PBULK | |
| | BZ | TPNOR | | | PI | PRNUM | |
| | PI | LERLT | | | DCI | PKGHL | |
| TPNOR | DCI | RTEMP | | | PI | PRMS | |
| | PI | DSPLY | | | PI | PRLN | |
| SIT | PI | RLKY | | | PI | PRBL | |
| SIQ | IN | H'20' | | | LISU | 3 | |
| | BZ | SID | | | LISL | 7 | |
| | IN | H'20' | | | LIS | 1 | |
| | CI | H'81' | | | NS | S | |
| | BNZ | XMOIS | | | BZ | NOPTL | |
| | PI | CLIK | | | PI | PRAST | |
| | BR | MOIS | | NOPTL | DCI | PTEMP | |
| XMOIS | CI | H'82' | | | PI | PRNUM | |
| | BNZ | XWEIGH | | | DCI | PDEGC | |
| | PI | CLIK | | | PI | PRMS | |
| | BR | WEIGHT | | | PI | PRLN | |
| XWEIGH | CI | H'84' | | | LISU | 3 | |
| | BNZ | SID | | | LISL | 7 | |
| | PI | CLIK | | | LIS | 7 | |
| | BR | TEMPER | | | NS | S | |
| SID | IN | H'21' | | | BZ | NOLEM | |

| Label | Mnemonic | Operand | Comment |
|---|---|---|---|
|  | PI | PRBK |  |
|  | PI | PRBK |  |
|  | PI | PRBL |  |
|  | DCI | PLIMEX |  |
|  | PI | PRMS |  |
|  | PI | PRLN |  |
| NOLEM | PI | PRBK |  |
|  | PI | PRBK |  |
|  | PI | PRBK |  |
|  | JMP | DSPER |  |
| CALDAT | LISU | 7 |  |
|  | PI | RND24 |  |
|  | LI | O'76' |  |
|  | LR | 0,A |  |
|  | LI | O'35' |  |
|  | LR | 1,A |  |
|  | PI | XFR2 |  |
|  | LI | O'32' |  |
|  | LR | 0,A |  |
|  | LI | O'76' |  |
|  | LR | 1,A |  |
|  | PI | XFR3 |  |
|  | LISU | 7 |  |
|  | PI | RND24 |  |
|  | LI | O'76' |  |
|  | LR | 0,A |  |
|  | LI | O'32' |  |
|  | LR | 1,A |  |
|  | PI | XFR2 |  |
|  | PI | FRST |  |
|  | BNZ | DSCDAT |  |
|  | JMP | PRCDAT |  |
| DSCDAT | LI | H'70' |  |
|  | OUTS | 1 |  |
|  | PI | NABL |  |
|  | PI | ALOFF |  |
| DSCDAU | LIS | 1 |  |
|  | LR | 0,A |  |
|  | PI | CCOF |  |
|  | DCI | RCDAT1 |  |
|  | PI | DSPLY |  |
|  | PI | HUMM |  |
|  | LIS | 2 |  |
|  | LR | 0,A |  |
|  | PI | CCOF |  |
|  | DCI | RCDAT2 |  |
|  | PI | DSPLY |  |
|  | PI | HUMM |  |
|  | LIS | 3 |  |
|  | LR | 0,A |  |
|  | PI | CCOF |  |
|  | DCI | RCDAT3 |  |
|  | PI | DSPLY |  |
|  | PI | HUMM |  |
|  | LIS | 4 |  |
|  | LR | 0,A |  |
|  | PI | CCOF |  |
|  | DCI | RCDAT4 |  |
|  | PI | DSPLY |  |
|  | PI | HUMM |  |
|  | BR | DSCDAU |  |
| PRCDAT | PI | PRBK |  |
|  | PI | PRBK |  |
|  | PI | PRBL |  |

| Label | Mnemonic | Operand | Comment |
|---|---|---|---|
|  | DCI | PCSHMM |  |
|  | PI | PRMS |  |
|  | PI | PRLN |  |
|  | PI | PRBK |  |
|  | PI | PRBL |  |
|  | DCI | PCAHAM |  |
|  | PI | PRMS |  |
|  | PI | PRLN |  |
|  | PI | PRBK |  |
|  | PI | PRBL |  |
|  | DCI | CD1LAB |  |
|  | PI | PRMS |  |
|  | DCI | CD1NUM |  |
|  | PI | PRNUM |  |
|  | PI | PRLN |  |
|  | PI | PRBL |  |
|  | DCI | CD2LAB |  |
|  | PI | PRMS |  |
|  | DCI | CD2NUM |  |
|  | PI | PRNUM |  |
|  | PI | PRLN |  |
|  | PI | PRBL |  |
|  | DCI | CD3LAB |  |
|  | PI | PRMS |  |
|  | DCI | CD3NUM |  |
|  | PI | PRNUM |  |
|  | PI | PRLN |  |
|  | PI | PRBL |  |
|  | DCI | CD4LAB |  |
|  | PI | PRMS |  |
|  | DCI | CD4NUM |  |
|  | PI | PRNUM |  |
|  | PI | PRLN |  |
|  | PI | PRBK |  |
|  | PI | PRBK |  |
|  | PI | PRBK |  |
|  | JMP | DSCDAT |  |

```
*
*
*
*
*
*
*
*
```

| Label | Mnemonic | Operand | Comment |
|---|---|---|---|
|  |  |  | FILE 2 — Start EC Measurement; setup according to (R0): |
| SETUP | LR | K,P | 0 KHZ EC |
|  | PI | SAVKQ | 1 KHZ RC |
|  | LISU | 2 | 2 MHZ RC |
|  | LISL | 6 | 3 MHZ EC |
|  | LR | A,0 | 4 WT |
|  | CI | 4 | 5 TEMP |
|  | LI | H'7E' |  |
|  | BNZ | SET1 |  |
|  | LI | H'F1' |  |
| SET1 | LR | I,A |  |
|  | LIS | 1 |  |
|  | BNZ | SET2 |  |
|  | LIS | 5 |  |
| SET2 | LR | S,A |  |
|  | LISU | 3 |  |
|  | LISL | 6 |  |
|  | LR | A,0 |  |
|  | LR | S,A |  |

| Label | Mnemonic | Operand | Comment |
|---|---|---|---|
| | PI | CTRS | |
| | LI | H'FE' | |
| | OUT | H'27' | |
| | EI | | |
| | JMP | KYBD | |
| CTRS | LR | K,P | I/O Board setup; |
| | DCI | STATBL | input select & |
| | LR | A,0 | counter reset |
| | ADC | | |
| | LM | | |
| | OUT | H'24' | |
| | PI | DLAY | |
| | CLR | | |
| | OUT | H'25' | |
| | LI | H'20' | |
| | OUT | H'25' | |
| | PK | | |
| CREAD | LR | K,P | read grain from |
| | LISU | 4 | counter, result |
| | LISL | 5 | in B6 |
| | PI | DGIN | |
| | JMP | BLOCK | |
| DCLRAL | LR | K,P | clear 5-digit |
| | PI | SAVKQ | display all |
| | PI | ALOFF | top messages |
| | LR | A,8 | |
| | NI | H'6B' | |
| | LR | 8,A | |
| | LIS | H'F' | |
| | LR | 0,A | |
| | PI | CCOF | |
| | LR | A,QU | |
| | LR | KU,A | |
| | LR | A,QL | |
| | LR | KL,A | |
| | LR | P,K | |
| DCLR | LISU | 4 | clear 4-digit |
| | LISL | 0 | display |
| | LI | H'FF' | |
| | LR | I,A | |
| | LR | S,A | |
| | JMP | DSWT | |
| BM6T7 | LISL | 4 | move B6→B7 |
| | LIS | 4 | |
| | LR | 0,A | |
| B671 | LISU | 6 | |
| | LR | A,S | |
| | LISU | 7 | |
| | LR | I,A | |
| | DS | 0 | |
| | BNZ | B671 | |
| | POP | | |
| BM7T6 | LISL | 4 | |
| | LIS | 4 | |
| | LR | 0,A | B7→B6 |
| B761 | LISU | 7 | |
| | LR | A,S | |
| | LISU | 6 | |
| | LR | I,A | |
| | DS | 0 | |
| | BNZ | B761 | |
| | POP | | |
| DPADJ | LR | K,P | |
| | PI | NORM | |

| Label | Mnemonic | Operand | Comment |
|---|---|---|---|
| | LIS | H'F' | Shift |
| | NS | S | B(⊕ISARU) |
| | COM | | so DP=(R2) |
| | INC | | return carry |
| | AS | 2 | set if |
| | BP | DPNOR | DP>(R2) |
| | AI | H'FF' | |
| | PK | | |
| DPNOR | LIS | H'F' | |
| | NS | S | |
| | COM | | |
| | INC | | |
| | AS | 2 | |
| | BZ | DPNRT | |
| | LR | A,S | |
| | LR | 1,A | |
| | CLR | | |
| | LR | S,A | |
| | PI | RSH | |
| | LR | A,1 | |
| | INC | | |
| | LR | S,A | |
| | BR | DPNOR | |
| DPNRT | COM | | |
| | PK | | |
| TEMP | LR | K,P | Compute temp |
| | PI | SAVKQ | (°C) from |
| | LISL | 7 | counts in B6 |
| | LI | H'10' | |
| | LR | S,A | |
| | LI | H'C8' | |
| | LR | 6,A | |
| | LISU | 7 | |
| | LISL | 4 | |
| | CLR | | |
| | LR | I,A | |
| | PI | ERDI | |
| | LISL | 7 | |
| | CLR | | |
| | LR | S,A | |
| | PI | ADD | |
| | DCI | TMPS | |
| | LISU | 5 | |
| | PI | LDOP | |
| | PI | BM7T6 | |
| | PI | MPY | |
| | LISU | 7 | |
| | LISL | 4 | |
| | CLR | | |
| | LR | I,A | |
| | LR | I,A | |
| | LI | H'25' | |
| | LR | I,A | |
| | LIS | 2 | |
| | LR | I,A | |
| | PI | ADD | |
| | LISU | 7 | |
| | LIS | 4 | |
| | LR | 2,A | |
| | PI | DPADJ | |
| | PI | RND24 | |
| | LISU | 7 | |
| | LIS | 4 | |
| | LR | 2,A | |

| Label | Mnemonic | Operand | Comment | Label | Mnemonic | Operand | Comment |
|---|---|---|---|---|---|---|---|
| | PI | ADJ | | | LR | A,0 | |
| | LR | r0,Q | | | LR | S,A | |
| RND24 | LR | K,P | | | LM | | |
| | LISL | 7 | round B(@ISARU) | | LR | 0,A | |
| | LR | A,IS | to 4 digits | | CLR | | |
| | XI | 0'10' | | | AM | | |
| | LR | IS,A | | | BZ | NOBLSD | |
| | CLR | | | | LR | A,S | |
| | LR | D,A | | | OI | H'F' | |
| | LR | D,A | | | LR | S,A | |
| | LR | D,A | | | DS | 0 | |
| | LI | H'50' | | NOBLSD | BZ | DWLZB | |
| | LR | S,A | | | LISL | 1 | |
| | PI | ADS | | | LR | A,S | |
| | PK | | | | CI | H'F' | |
| XFR3 | LIS | 3 | | | BM | DWLZB | |
| | BR | XFRX | transfer 3 bytes | | OI | H'F0' | |
| XFR2 | LIS | 2 | from @ (R0) to | | LR | S,A | |
| XFRX | LR | 2,A | @ (R1) | | DS | 0 | |
| XLOP | LR | A,0 | | | BZ | DWLZB | |
| | LR | IS,A | | | NI | H'F' | |
| | LR | A,S | | | BNZ | DWLZB | |
| | LR | 3,A | | | LI | H'FF' | |
| | LR | A,1 | | | LR | D,A | |
| | LR | IS,A | | | DS | 0 | |
| | LR | A,3 | | | BZ | DWLZB | |
| | LR | S,A | | | LR | A,S | |
| | DS | 0 | | | CI | H'F' | |
| | DS | 1 | | | BM | DWLZB | |
| | DS | 2 | | | OI | H'F0' | |
| | BNZ | XLOP | | | LR | S,A | |
| | POP | | | | JMP | DSWT | |
| XFR4 | LIS | 4 | | DWLZB | | | |
| | BR | XFRX | | LERLT | LI | H'69' | on |
| DLAY | LI | 60 | .15 sec delay | | OUTS | 1 | |
| DLYN | LR | 0,A | | | JMP | NABL | |
| DLYZ | LR | 1,A | | LIDP | LI | H'79' | dpon |
| DLY1 | DS | 0 | | | OUTS | 1 | |
| | BNZ | DLY1 | | | JMP | NABL | |
| | DS | 1 | | FRDATE | LR | K,P | |
| | BNZ | DLY1 | .5 sec delay | | PI | SAVKQ | date printout |
| | POP | | | | PI | PRBL | (blank if not |
| SMTM | LI | 194 | | | DCI | PDATE | entered since |
| | LR | 0,A | | | PI | PRMS | reset) |
| | LI | 194 | | | LISU | 7 | |
| | BR | DLYN | | | LISL | 0 | |
| SMON | IN | H'21' | | | CLR | | |
| | NI | H'20' | turn on strikeoff | | AS | 1 | |
| | BNZ | SMOK | motor | | BZ | NODPR | |
| | LIS | 6 | | | DCI | PMONTH | |
| | LR | 0,A | | | PI | PRNUM | |
| | JMP | ERROR | | | PI | PRSL | grain name |
| SMOK | LI | H'7D' | | | DCI | PDAY | printout |
| SMET | OUTS | 1 | | | PI | PRNUM | |
| | JMP | NABL | | | PI | PRSL | |
| SMOF | LI | H'75' | off | | DCI | PYEAR | |
| | BR | SMET | | | PI | PRNUM | |
| DSPLY | LM | | display # | NODPR | PI | PRLN | |
| | LR | IS,A | scratchpad, | | LR | P0,Q | |
| | LR | A,I | setup info | FRGR | LR | K,P | grain name |
| | LR | 0,A | @ DC: | | PI | PRBL | printout |
| | LR | A,I | ISAR/#LZB+1/'1' if | | PI | CCPT | |
| | LISU | 4 | if blank lo digit | | LI | H'1C' | |
| | LISL | 1 | | | AS | 6 | |
| | LR | D,A | | | LR | 6,A | |

| Label | Mnemonic | Operand | Comment | Label | Mnemonic | Operand | Comment |
|-------|----------|---------|---------|-------|----------|---------|---------|
|       | LISU     | 0       |         |       | LR       | 6,A     |         |
|       | LISL     | 0       |         | CLIP  | DS       | 5       |         |
|       | PI       | ERDI    |         |       | BNZ      | CLIP    |         |
|       | LR       | A,1     |         |       | DS       | 6       |         |
|       | SR       | 4       |         |       | BNZ      | CLIP    |         |
|       | SL       | 1       |         |       | LI       | H'74'   |         |
|       | LR       | 0,A     |         |       | OUTS     | 1       |         |
|       | SL       | 1       |         |       | PI       | NABL    |         |
|       | SL       | 1       |         |       | PK       |         |         |
|       | AS       | 0       |         | ERDR  | LISU     | 4       |         |
|       | LR       | 0,A     |         |       | LISL     | 0       |         |
|       | LIS      | H'F'    |         | ERDI  | LR       | A,6     | EAROM read; |
|       | NS       | 1       |         |       | COM      |         | return 4 digit |
|       | AS       | 0       |         |       | OI       | 3       | @R6 to @ISAR |
|       | SL       | 4       |         |       | LR       | 6,A     |         |
|       | LR       | 0,A     |         |       | LI       | H'10'   |         |
|       | DCI      | GRTBL   |         |       | OUTS     | 9       |         |
|       | LR       | 0,DC    |         |       | CLR      |         |         |
|       | LR       | A,QL    |         |       | LR       | 5,A     |         |
|       | AS       | 0       |         |       | LIS      | 4       |         |
|       | LR       | QL,A    |         |       | LR       | 4,A     |         |
|       | LR       | A,QU    |         | ERD3  | LIS      | H'C'    |         |
|       | LNK      |         |         |       | OUTS     | 5       |         |
|       | LR       | QU,A    |         |       | LR       | A,6     |         |
|       | LR       | DC,Q    |         |       | OUTS     | 8       |         |
|       | LI       | O'67'   |         |       | LI       | H'10'   |         |
|       | LR       | 4,A     |         |       | OUTS     | 5       |         |
|       | LI       | 16      |         |       | CLR      |         |         |
|       | LR       | 0,A     |         |       | AS       | 5       |         |
|       | PI       | PRMO    |         |       | BNZ      | ERD1    |         |
|       | JMP      | PRLK    |         |       | INS      | 4       |         |
| NABL  | LI       | H'40'   |         |       | SR       | 4       |         |
|       | OUTS     | 0       |         |       | LR       | S,A     |         |
|       | INS      | 4       | "write" pulse | | BR | ERD2 | |
|       | INS      | 4       | to latches | ERD1 | INS | 4 | |
|       | INS      | 4       |         |       | XS       | S       |         |
|       | INS      | 4       |         |       | LR       | I,A     |         |
|       | INS      | 4       |         | ERD2  | DS       | 6       |         |
|       | INS      | 4       |         |       | LR       | A,5     |         |
|       | CLR      |         |         |       | COM      |         |         |
|       | OUTS     | 0       |         |       | LR       | 5,A     |         |
|       | POP      |         |         |       | DS       | 4       |         |
| HUMM  | LR       | K,P     |         |       | BNZ      | ERD3    |         |
| HUMO  | IN       | H'20'   | wait for "CAL", | | LIS | 4 | |
|       | BNZ      | HUMO    | dump, or load | | OUTS | 5 | |
| HUML  | IN       | H'20'   |         |       | CLR      |         |         |
|       | BZ       | DOWN    |         |       | OUTS     | 9       |         |
|       | CI       | H'18'   |         |       | POP      |         |         |
|       | BZ       | CLIKK   |         | ERWR  | LR       | A,6     | EAROM write, |
| DOWN  | IN       | H'21'   |         |       | COM      |         | store 4 digits |
|       | NI       | 3       |         |       | OI       | 3       | in R40-41 to |
|       | BZ       | HUML    |         |       | LR       | 6,A     | @R6 |
|       | CI       | 2       |         |       | NI       | H'FE'   |         |
|       | BNZ      | CKDP    |         |       | OUTS     | 8       |         |
|       | LR       | A,8     |         |       | LI       | H'10'   |         |
|       | OI       | 2       |         |       | OUTS     | 9       |         |
|       | LR       | 8,A     |         |       | LIS      | 8       |         |
| CKDP  | JMP      | DUMP    |         |       | OUTS     | 5       |         |
| CLIK  | LR       | K,P     |         |       | LI       | H'18'   |         |
| CLIKK | LI       | H'7C'   | hit click |     | OUTS     | 5       |         |
|       | OUTS     | 1       | solenoid |      | CLR      |         |         |
|       | PI       | NABL    |         |       | LR       | 1,A     |         |
|       | LR       | 5,A     |         |       | LR       | 0,A     |         |
|       | LIS      | 4       |         | ERW1  | ADC      |         |         |

| Label | Mnemonic | Operand | Comment |
|---|---|---|---|
| | DS | 0 | |
| | BNZ | ERW1 | |
| | DS | 1 | |
| | BNZ | ERW1 | |
| | LIS | 8 | |
| | OUTS | 5 | |
| | LISU | 4 | |
| | LISL | 0 | |
| | LIS | H'C' | |
| | OUTS | 5 | |
| | LIS | 4 | |
| | OUTS | 5 | |
| | LIS | H'F' | |
| | NS | S | |
| | OUTS | 4 | |
| | LR | A,6 | |
| | OUTS | 8 | |
| | CLR | | |
| | OUTS | 5 | |
| | DS | 6 | |
| | LR | A,6 | |
| | OUTS | 8 | |
| | LR | A,I | |
| | SR | 4 | |
| | OUTS | 4 | |
| | LR | A,6 | |
| | NI | H'FC' | |
| | OUTS | 8 | |
| | DS | 6 | |
| | LR | A,6 | |
| | OUTS | 8 | |
| | LIS | H'F' | |
| | NS | S | |
| | OUTS | 4 | |
| | DS | 6 | |
| | LR | A,6 | |
| | OUTS | 8 | |
| | LR | A,S | |
| | SR | 4 | |
| | OUTS | 4 | |
| | LI | H'10' | |
| | OUTS | 5 | |
| | LI | 180 | |
| | LR | 0,A | |
| ERW2 | DS | 0 | |
| | BNZ | ERW2 | |
| | CLR | | |
| | OUTS | 5 | |
| | LIS | 4 | |
| | OUTS | 5 | |
| | CLR | | |
| | OUTS | 4 | |
| | OUTS | 9 | |
| | POP | | |
| PRBL | LISL | 7 | |
| | LI | H'20' | |
| PRB1 | LISU | 5 | |
| | LR | S,A | |
| | LISU | 6 | Clear Print |
| | LR | D,A | Buffer |
| | BR7 | PRB1 | |
| | LI | O'67' | |
| | LR | 4,A | |
| | POP | | |

| Label | Mnemonic | Operand | Comment |
|---|---|---|---|
| PRNM | LI | H'30' | |
| | AS | 0 | |
| PRAC | LR | 0,A | |
| PRR0 | LR | A,4 | |
| | LR | IS,A | Print #in R0 |
| | LR | A,0 | |
| | LR | S,A | |
| | DS | 4 | |
| | POP | | |
| PRDP | LI | H'2E' | |
| | BR | PRAC | |
| PRBK | LR | K,P | |
| | PI | PRBL | Line feed |
| | JMP | PRLK | |
| PRST | INS | 0 | |
| | NI | H'10' | Return printer |
| | BNZ | PRS1 | status: 'zero' |
| | INC | | if ready |
| | POP | | |
| PRS1 | LIS | H'C' | |
| | OUTS | 0 | |
| | INS | 0 | |
| | NI | H'10' | |
| | CLR | | |
| | OUTS | 0 | |
| | BNZ | PRS2 | |
| | COM | | |
| | POP | | |
| PRS2 | SR | 4 | |
| | POP | | |
| MPY | LR | K,P | |
| MPZ | LI | O'67' | |
| | LR | 0,A | 35 x B6 →B6 |
| | LI | O'63' | |
| | LR | 1,A | |
| | PI | XFR4 | |
| | LISU | 6 | |
| | LISL | 4 | |
| | CLR | | |
| WIPE | LR | I,A | |
| | BR7 | WIPE | |
| | LR | S,A | |
| | LISU | 5 | |
| | LR | A,S | |
| | LISU | 6 | |
| | LISL | 3 | |
| | AS | S | |
| | NI | H'1F' | |
| | LR | 2,A | |
| | LISL | 0 | |
| | LIS | 7 | |
| | LR | 1,A | |
| M1 | DS | 1 | |
| | BC | M3 | |
| M2 | LIS | 1 | |
| | NS | 1 | |
| | BNZ | M3 | |
| | LR | A,S | |
| | NI | H'F' | |
| | BR | M4 | |
| M3 | LR | A,I | |
| | SR | 4 | |
| M4 | LR | 0,A | |
| | LR | A,IS | |
| | LR | 3,A | |

| Label | Mnemonic | Operand | Comment |
|-------|----------|---------|---------|
|       | LISU     | 6       |         |
|       | PI       | RSH     |         |
| M5    | CLR      |         |         |
|       | AS       | 0       |         |
|       | BNZ      | M6      |         |
|       | LR       | A,3     |         |
|       | LR       | IS,A    |         |
|       | BR       | M1      |         |
| M6    | LISL     | 4       |         |
| M7    | LISU     | 5       |         |
|       | LR       | A,S     |         |
|       | AI       | H'66'   |         |
|       | LISU     | 6       |         |
|       | ASD      | S       |         |
|       | LR       | I,A     |         |
|       | LR       | A,S     |         |
|       | LNK      |         |         |
|       | LR       | S,A     |         |
|       | BR7      | M7      |         |
|       | DS       | 0       |         |
|       | BR       | M5      |         |
| M8    | LISU     | 6       |         |
|       | CLR      |         |         |
|       | AS       | S       |         |
|       | BNZ      | M9      |         |
|       | LIS      | H'F'    |         |
|       | NS       | 2       |         |
|       | BZ       | M9      |         |
|       | DS       | 2       |         |
|       | BR       | M10     |         |
| M9    | PI       | RSH     |         |
| M10   | LR       | A,2     |         |
|       | LISL     | 7       |         |
|       | LR       | S,A     |         |
|       | LR       | P,K     |         |
|       | JMP      | NORM    |         |
| RSH   | LISL     | 4       |         |
| RSH1  | LR       | A,S     | shift right |
|       | SR       | 4       | B(⊖ISARU) |
|       | LR       | I,A     | 1 digit |
|       | LR       | A,D     |         |
|       | SL       | 4       |         |
|       | XS       | S       |         |
|       | LR       | I,A     |         |
|       | BR7      | RSH1    |         |
|       | CLR      |         |         |
|       | LR       | S,A     |         |
|       | POP      |         |         |
| ADS   | COM      |         |         |
|       | LISL     | 4       |         |
| ADD1  | LISU     | 6       | add B6 to B7 |
|       | LR       | A,S     |         |
|       | AI       | H'66'   |         |
|       | LISU     | 7       |         |
|       | ASD      | S       |         |
|       | LR       | I,A     |         |
|       | LR       | A,S     |         |
|       | LNK      |         |         |
|       | LR       | S,A     |         |
|       | BR7      | ADD1    |         |
|       | POP      |         |         |
| CMP   | CLR      |         |         |
|       | LR       | 1,A     |         |
|       | LISL     | 4       | comp B(⊖ISARU) |
| REDC  | CLR      |         |         |

| Label | Mnemonic | Operand | Comment |
|-------|----------|---------|---------|
|       | AS       | S       |         |
|       | BNZ      | CM1     |         |
|       | AS       | 1       |         |
|       | BNZ      | NOAL    |         |
| CM1   | COM      |         |         |
|       | ASD      | 1       |         |
|       | LR       | S,A     |         |
|       | CLR      |         |         |
|       | LR       | 1,A     |         |
| NOAL  | LR       | A,I     |         |
|       | BR7      | REDC    |         |
|       | POP      |         |         |
| ADD   | LR       | K,P     |         |
| ADDK  | LISU     | 7       |         |
|       | LISL     | 7       |         |
|       | LR       | A,S     |         |
|       | LR       | 1,A     | Add (Signed, |
|       | CLR      |         | floating-pt) |
|       | LR       | S,A     |         |
|       | LISU     | 6       |         |
|       | LR       | A,S     |         |
|       | LR       | 0,A     |         |
|       | CLR      |         |         |
|       | LR       | S,A     |         |
|       | LIS      | H'F'    |         |
|       | NS       | 1       |         |
|       | LR       | 3,A     |         |
|       | LIS      | H'F'    |         |
|       | NS       | 0       |         |
|       | LR       | 2,A     |         |
|       | LR       | 4,A     |         |
| ADL   | COM      |         |         |
|       | INC      |         |         |
|       | AS       | 3       |         |
|       | BZ       | SIGN    |         |
|       | BM       | RSAS    |         |
|       | LISU     | 6       |         |
|       | PI       | RSH     |         |
|       | LR       | A,2     |         |
|       | INC      |         |         |
|       | LR       | 2,A     |         |
|       | LR       | 4,A     |         |
|       | BR       | ADL     |         |
| RSAS  | LISU     | 7       |         |
|       | PI       | RSH     |         |
|       | LR       | A,3     |         |
|       | INC      |         |         |
|       | LR       | 3,A     |         |
|       | LR       | A,2     |         |
|       | BR       | ADL     |         |
| SIGN  | LR       | A,1     |         |
|       | XS       | 0       |         |
|       | SR       | 4       |         |
|       | BNZ      | SUB     |         |
|       | PI       | ADS     |         |
|       | BZ       | ADD4    |         |
|       | LISU     | 7       |         |
|       | PI       | RSH     |         |
|       | LR       | A,2     |         |
|       | INC      |         |         |
|       | LR       | 2,A     |         |
| ADD4  | LR       | A,0     |         |
|       | NI       | H'10'   |         |
|       | AS       | 2       |         |

| Label | Mnemonic | Operand | Comment | Label | Mnemonic | Operand | Comment |
|---|---|---|---|---|---|---|---|
| | LR | S,A | | | BNZ | DPCK | |
| RTDP6 | LISU | 6 | | | LISU | 4 | |
| | LR | A,4 | | | LISL | 1 | |
| | LR | S,A | | | LR | A,I | |
| | LISU | 7 | | | SR | 4 | |
| | LR | P,K | | | CI | 9 | |
| | BR | NORM | | | BM | * | |
| SUB | LR | A,0 | | | LIS | H'F' | |
| | SR | 4 | | | NS | S | |
| | BZ | CMPA | | | CI | 8 | |
| | LISU | 6 | | | BM | * | |
| | BR | EITH | | | DI | | |
| CMPA | LISU | 7 | | | PI | CCPT | |
| EITH | PI | CMP | | | LISU | 4 | |
| | PI | ADS | | | LISL | 2 | |
| | BNZ | QUIT | | | LIS | H'F' | |
| | LISU | 7 | | | NS | S | |
| | PI | CMP | | | AI | H'FF' | |
| QUIT | LIS | 1 | | | SL | 1 | |
| | XS | S | | | SL | 1 | |
| | SL | 4 | | | AS | 6 | |
| | AS | 2 | | | LR | 6,A | |
| | LR | S,A | | | PI | ERWR | |
| | BR | RTDP6 | | | JMP | LTOF | |
| NORM | LISL | 6 | ShiftB(@ISARU) DPCK | | CI | 1 | |
| | LI | H'F0' | left until DP→0 | | BNZ | LDCK | |
| | NS | I | or MSD ≠0 | | DI | | |
| | BNZ | NMNR | | | JMP | DUMP | |
| | LR | A,S | | LDCK | LIS | 8 | |
| | SL | 4 | | | NS | 8 | |
| | BZ | NMNR | | | BZ | NORYET | |
| | DS | D | | | DI | | |
| | LIS | 3 | | | JMP | LOAD | |
| | LR | 0,A | | NORYET | LR | A,8 | |
| NMR1 | LR | A,S | | | OI | 2 | |
| | SL | 4 | | | LR | 8,A | |
| | LR | D,A | | | BR | * | |
| | LR | A,I | | KYPH | DI | | |
| | SR | 4 | | | | | Key sensed |
| | XS | S | | | LIS | 4 | |
| | LR | D,A | | | LR | 6,A | |
| | DS | 0 | | | LR | 5,A | |
| | BNZ | NMR1 | | DLP1 | DS | 5 | |
| | LR | A,I | | | BNZ | DLP1 | |
| | LR | A,S | | | DS | 6 | |
| | NI | H'F0' | | | BNZ | DLP1 | |
| | LR | S,A | | | DCI | TABL | |
| | BR | NORM | | | LIS | H'F' | |
| NMNR | POP | | | | LR | 0,A | |
| * | | | | | IN | H'20' | |
| * | | | | CMPR | CM | | |
| * | | | | | BZ | FFND | |
| * | | | | | DS | 0 | |
| * | | | | | BC | CMPR | |
| * | | FILE 3 | | | JMP | PST | |
| * | | | | FFND | PI | CLIK | |
| * | | | | | LR | A,0 | |
| KYBD | IN | H'20' | | | CI | 9 | |
| | BZ | LDFG | Scan KBD | | BM | CMND | |
| | JMP | KYPH | | | LR | A,8 | |
| LDFG | IN | H'21' | | | NI | H'80' | |
| | NI | 7 | | | BNZ | FNM | |
| | BZ | * | | | LISU | 4 | |
| | CI | 4 | | | LISL | 0 | |
| | | | | | LI | H'FF' | |

| Label | Mnemonic | Operand | Comment |
|---|---|---|---|
|  | LR | I,A |  |
|  | LR | S,A |  |
|  | LR | A,8 |  |
|  | OI | H'80' |  |
|  | LR | 8,A |  |
| FNM | LISU | 4 |  |
|  | LISL | 1 |  |
|  | LR | A,S |  |
|  | SL | 4 |  |
|  | LR | D,A |  |
|  | LR | A,I |  |
|  | SR | 4 |  |
|  | AS | S |  |
|  | LR | D,A |  |
|  | LR | A,S |  |
|  | SL | 4 |  |
|  | AS | 0 |  |
|  | LR | S,A |  |
|  | PI | DSWT |  |
| RELS | PI | RLKY |  |
| RST | LISU | 3 |  |
|  | LISL | 6 |  |
|  | LIS | H'F' |  |
|  | NS | S |  |
|  | DCI | RSTABL |  |
|  | SL | 1 |  |
|  | ADC |  |  |
|  | LM |  |  |
|  | LR | QU,A |  |
|  | LM |  |  |
|  | LR | QL,A |  |
|  | LR | P0,Q | wait for key |
| RLKY | IN | H'20' | to be released |
|  | BNZ | RLKY |  |
|  | LIS | 4 |  |
|  | LR | 6,A |  |
|  | LR | 5,A |  |
| RLP1 | DS | 5 |  |
|  | BNZ | RLP1 |  |
|  | DS | 6 |  |
|  | BNZ | RLP1 |  |
|  | POP |  |  |
| CMND | LR | A,8 |  |
|  | NI | H'6B' |  |
|  | LR | 8,A |  |
|  | LR | A,0 |  |
|  | CI | H'F' |  |
|  | BNZ | CMFWT |  |
|  | PI | PRST | "moisture" |
|  | BNZ | RELS | (date enter) |
|  | LISU | 4 |  |
|  | LISL | 7 |  |
|  | LIS | 1 |  |
|  | NS | S |  |
|  | BNZ | MKWAP |  |
|  | LIS | 1 |  |
|  | LR | S,A |  |
|  | PI | DCLRAL |  |
|  | PI | PPBL |  |
|  | DCI | PENTMO | ("day") |
|  | BR | ALDEC |  |
| MKWAP | LR | A,S |  |
|  | CI | 1 |  |
|  | BNZ | MKPDA |  |
|  | LI | H'11' |  |

| Label | Mnemonic | Operand | Comment |
|---|---|---|---|
|  | LR | LR I,A |  |
|  | LR | A,S |  |
|  | CI | H'FF' |  |
|  | BZ | NOCHM |  |
|  | CI | H'31' |  |
|  | BC | MOLETW |  |
|  | NI | H'F' |  |
| MOLETW | LISU | 7 | Store day |
|  | LISL | 1 |  |
|  | LR | S,A |  |
| NOCHM | PI | DCLRAL | "Month" |
|  | PI | PRBL |  |
|  | DCI | PENTDA |  |
|  | BR | ALDEC | store month |
| MKPDA | CI | H'11' |  |
|  | BNZ | MKPYR |  |
|  | LI | H'21' |  |
|  | LR | I,A |  |
|  | LR | A,S |  |
|  | CI | H'FF' |  |
|  | BZ | NOCHD |  |
|  | CI | H'12' |  |
|  | BC | DALETO |  |
|  | NI | H'F' |  |
| DALETO | LISU | 7 |  |
|  | LISL | 0 |  |
|  | LR | S,A |  |
| NOCHD | PI | DCLRAL | "year" |
|  | PI | PRBL |  |
|  | DCI | PENTYR |  |
|  | BR | ALDEC |  |
| MKPYR | CLR |  | store year |
|  | LR | I,A |  |
|  | LR | A,S |  |
|  | CI | H'99' |  |
|  | BNC | NOCHY |  |
|  | LISL | 6 |  |
|  | LR | S,A |  |
| NOCHY | PI | DCLRAL |  |
|  | PI | PRDATE |  |
|  | BR | DPABLF |  |
| ALDEC | PI | PRMS |  |
|  | PI | PRLN |  |
| DPABLF | PI | PRBK |  |
|  | PI | PRBK |  |
|  | JMP | STKH |  |
| CMFWT | CI | H'E' | weight |
|  | BNZ | CMFTP |  |
|  | LI | H'6D' |  |
|  | OUTS | 1 |  |
|  | PI | NABL |  |
|  | PI | RLKY |  |
| WFWRT | IN | H'20' | wait for |
|  | BNZ | DWWTS | "write" |
|  | IN | H'21' | Button |
|  | CI | H'34' |  |
|  | BNZ | WFWRT |  |
|  | LISU | 4 |  |
|  | LISL | 1 |  |
|  | LR | A,S |  |
|  | CI | H'99' |  |
|  | BC | DWXYZ |  |
|  | LIS | 4 |  |

| Label | Mnemonic | Operand | Comment |
|---|---|---|---|
| | LR | 0,A | |
| | PI | CTRS | if display blank, |
| | LIS | 8 | read & store scale |
| | LR | 0,A | intercept |
| | LI | H'9B' | |
| | LR | 1,A | if not, store |
| | LI | H'9B' | display as scale |
| | LR | 2,A | slope |
| DWDLY | DS | 2 | |
| | BNZ | DWDLY | |
| | DS | 1 | |
| | BNZ | DWDLY | |
| | DS | 0 | |
| | BNZ | DWDLY | |
| | LISU | 4 | |
| | LISL | 1 | |
| | PI | DGIN | |
| | LISL | 7 | |
| | CLR | | |
| | LR | S,A | |
| | LI | H'C0' | |
| | LR | 6,A | |
| | PI | ERWR | |
| | BR | DWWTS | |
| DWXYZ | LI | H'C4' | |
| | LR | 6,A | |
| | PI | ERWR | |
| DWWTS | PI | DCLRAL | |
| | JMP | RST | |
| CMFTP | CI | H'D' | TEMP |
| | BNZ | CMFGR | |
| | LI | H'6C' | |
| | OUTS | 1 | |
| | PI | NABL | |
| | PI | RLKY | |
| PFWRT | IN | H'20' | wait for "write" |
| | BNZ | DWWTS | |
| | IN | H'31' | |
| | CI | H'34' | |
| | BNZ | PFWRT | |
| | LIS | 5 | store $T_{25}$ |
| | LR | 0,A | counts |
| | PI | CTRS | |
| | PI | SMTM | |
| | LISU | 4 | |
| | LISL | 1 | |
| | PI | DGIN | |
| | LISL | 7 | |
| | CLR | | |
| | LR | S,A | |
| | LI | H'C8' | |
| | LR | 6,A | |
| | PI | ERWR | |
| | BR | DWWTS | |
| CMFGR | CI | H'C' | |
| | BNZ | CMFCC | |
| | BR | SEL | |
| ALYT | LI | H'5F' | Grain |
| | LR | 1,A | |
| | LIS | 8 | |
| | LR | 2,A | |
| LTLP | LR | A,1 | |
| | OUTS | 1 | |
| | PI | NAFM | |
| | DS | 1 | |

| Label | Mnemonic | Operand | Comment |
|---|---|---|---|
| | DS | 2 | |
| | BNZ | LTLP | |
| | PI | RLKY | |
| | PI | DCLRAL | |
| | PI | BCLR | |
| | PI | RLKY | |
| | JMP | RST | |
| | LR | A,8 | |
| | NI | H'5F' | |
| | LR | 8,A | |
| | LISU | 4 | |
| | LISL | 0 | |
| | LIS | H'F' | |
| | NS | S | |
| | BZ | ALYT | |
| | CI | 9 | |
| | BM | ALYT | |
| | BNZ | GRLT9 | |
| | LR | A,8 | |
| | OI | H'20' | |
| | LR | 8,A | |
| | PI | PRST | |
| | BNZ | LTOF | |
| | PI | BCLR | |
| | PI | PRBL | |
| | DCI | PCDM1 | |
| | PI | PRMS | |
| | PI | PRLN | |
| | PI | PRBL | |
| | DCI | PCDM2 | |
| | PI | PRMS | |
| | PI | PRLN | |
| | PI | PRBK | |
| | PI | PRDATE | |
| | PI | PRBK | |
| | PI | PRBK | |
| | PI | DCLRAL | |
| | PI | RLKY | |
| | JMP | STKH | |
| GRLT9 | CI | 6 | |
| | BM | LTOF | |
| | LISL | 2 | |
| | SL | 4 | |
| | OI | H'F' | |
| | LR | S,A | |
| | BR | LTOF | |
| CMFCC | CI | H'8' | |
| | BNZ | CMFSC | |
| | LR | A,8 | 'CAL' |
| | NI | H'7F' | |
| | LR | 8,A | |
| | NI | H'20' | |
| | BNZ | RELL | |
| | LISU | 4 | |
| | LISL | 0 | |
| | LIS | H'F' | |
| | NS | S | |
| | BNZ | CMFZ | |
| | PI | PRST | |
| | BNZ | RELL | |
| | JMP | PRCCOF | |
| CMFZ | CI | 8 | |
| | BM | RELL | |
| | LR | 0,A | |
| | LR | A,8 | |

| Label | Mnemonic | Operand | Comment |
|---|---|---|---|
| | OI | 4 | |
| | LR | 8,A | |
| | PI | CCOF | |
| | PI | CCPT | |
| | DS | 0 | |
| | LR | A,0 | |
| | SL | 1 | |
| | SL | 1 | |
| | AS | 6 | |
| | LR | 6,A | |
| | PI | ERDR | |
| | PI | DSWT | |
| | PI | BCLR | |
| | LI | H'68' | |
| | OUTS | 1 | |
| | PI | NABL | |
| | PI | PLKY | |
| | JMP | RELL | |
| CMFSC | LI | 16 | |
| | LR | 2,A | |
| | DCI | LITTBL | self-check |
| | PI | LATCL | |
| RANDOM | LM | | |
| | OUTS | 1 | |
| | PI | NABL | |
| | PI | SMTM | |
| | PI | LATCL | |
| | DS | 2 | |
| | BNZ | RANDOM | |
| | CLR | | |
| | LR | 3,A | |
| NUML | LIS | 4 | |
| | LR | 4,A | |
| DIGL | LR | A,4 | |
| | SL | 4 | |
| | AS | 3 | |
| | OUTS | 1 | |
| | PI | NABL | |
| | DS | 4 | |
| | BP | DIGL | |
| | PI | SMTM | |
| | PI | SMTM | |
| | LR | A,3 | |
| | INC | | |
| | LR | 3,A | |
| | CI | 11 | |
| | BNZ | NUML | |
| | LI | H'78' | |
| | OUTS | 1 | |
| | PI | NABL | |
| | LI | H'6E' | |
| | OUTS | 1 | |
| | PI | NABL | |
| | LI | H'5F' | |
| | OUTS | 1 | |
| | PI | NABL | |
| | LIS | 8 | |
| | NS | 8 | |
| | BNZ | SIRGA | |
| | CLR | | |
| | LR | 0,A | |
| | PI | CTRS | |
| | PI | SMTM | |
| | PI | CREAD | |
| | LISU | 6 | |
| | LIS | 3 | |
| | LR | 2,A | |
| | PI | DPADJ | |
| | LI | 0'66' | |
| | LR | 0,A | |
| | LI | 0'32' | |
| | LR | 1,A | |
| | PI | XFR3 | |
| | LIS | 3 | |
| | LR | 0,A | |
| | PI | CTRS | |
| | PI | SMTM | |
| | PI | CREAD | |
| | LISU | 6 | |
| | LIS | 3 | |
| | LR | 2,A | |
| | PI | DPADJ | |
| | LI | 0'66' | |
| | LR | 0,A | |
| | LI | 0'35' | |
| | LR | 1,A | |
| | PI | XFR3 | |
| SIRGA | LIS | 1 | |
| | LR | 0,A | |
| | PI | CTR3 | |
| | PI | SMTM | |
| | PI | CREAD | |
| | LI | 0'32' | |
| | LR | 0,A | |
| | LI | 0'76' | |
| | LR | 1,A | |
| | PI | XFR3 | |
| | LISU | 7 | |
| | LISL | 7 | |
| | LI | H'13' | |
| | LR | S,A | |
| | PI | ADD | |
| | LIS | 3 | |
| | LR | 2,A | |
| | LISU | 7 | |
| | PI | DPADJ | |
| | PI | RND24 | |
| | LI | 0'76' | |
| | LR | 0,A | |
| | LI | 0'32' | |
| | LR | 1,A | |
| | PI | XFR2 | |
| | LIS | 2 | |
| | LR | 0,A | |
| | PI | CTRS | |
| | PI | SMTM | |
| | PI | CREAD | |
| | LI | 0'35' | |
| | LR | 0,A | |
| | LI | 0'76' | |
| | LR | 1,A | |
| | PI | XFR3 | |
| | LISU | 7 | |
| | LISL | 7 | |
| | LI | H'13' | |
| | LR | S,A | |
| | PI | ADD | |
| | LIS | 3 | |
| | LR | 2,A | |

| Label | Mnemonic | Operand | Comment | Label | Mnemonic | Operand | Comment |
|---|---|---|---|---|---|---|---|
| | LISU | 7 | | | PI | PRBK | |
| | PI | DPADJ | | | CLR | | |
| | PI | PND24 | | | LR | 7,A | |
| | LI | O'76' | | PRCCLP | PI | PRBL | |
| | LR | 0,A | | | DCI | PCC1 | |
| | LI | O'35' | | | LR | A,7 | |
| | LR | 1,A | | | SL | 1 | |
| | PI | XFR2 | | | SL | 1 | |
| | PI | PRST | | | ADC | | |
| | BNZ | DRCSIM | | | PI | PRMS | |
| | PI | PRBK | | | PI | CCPT | |
| | PI | PRBL | | | LR | A,7 | |
| | DCI | PRCSIM | | | SL | 1 | |
| | PI | PRMS | | | SL | 1 | |
| | PI | PRLN | | | AS | 6 | |
| | PI | PRBL | | | LR | 6,A | |
| | DCI | PRCSIM | | | PI | ERDR | |
| | PI | PRMS | | | DCI | PCCOF | |
| | PI | PRLN | | | PI | PRNUM | |
| | PI | PRBK | | | PI | PRLN | |
| | PI | PRBL | | | LR | A,7 | |
| | DCI | CD1LAB | | | INC | | |
| | PI | PRMS | | | LR | 7,A | |
| | DCI | CD1NUM | | | CI | 8 | |
| | PI | PRNUM | | | BNZ | PRCCLP | |
| | PI | PRLN | | | PI | CKSUM | |
| | PI | PRBL | | | BZ | CKOKH | |
| | DCI | CD2LAB | | | PI | PRBK | |
| | PI | PRMS | | | PI | PRBL | |
| | DCI | CD2NUM | | | DCI | INVCM | |
| | PI | PRNUM | | | PI | PRMS | |
| | PI | PRLN | | | PI | PRLN | |
| | PI | PRBK | | CKOKH | PI | PRBK | |
| | PI | PRBK | | | PI | PRBK | |
| | PI | PRBK | | | PI | PRBK | |
| DRCSIM | LI | H'70' | | | JMP | STKH | |
| | OUTS | 1 | | DSWT | LR | K,P | |
| | PI | NABL | | | CLR | | |
| DRCDAU | LIS | 1 | | | LR | 1,A | |
| | LR | 0,A | | | LISU | 4 | Display |
| | PI | CCOF | | | LISL | 0 | register |
| | DCI | RCDAT1 | | | LR | A,S | readout |
| | PI | DSPLY | | | LR | 3,A | |
| | PI | HUMM | | | PI | DSUP | |
| | LIS | 2 | | | LI | H'10' | |
| | LR | 0,A | | | LR | 1,A | |
| | PI | CCOF | | | LR | A,I | |
| | DCI | RCDAT2 | | | SR | 4 | |
| | PI | DSPLY | | | LR | 3,A | |
| | PI | HUMM | | | PI | DSUP | |
| | BR | DRCDAU | | | LI | H'20' | |
| LATCL | LI | H'80' | latch reset | | LR | 1,A | |
| | OUTS | 0 | | | LR | A,S | |
| | INS | 4 | | | LR | 3,A | |
| | INS | 4 | | | PI | DSUP | |
| | INS | 4 | | | LI | H'30' | |
| | INS | 4 | | | LR | 1,A | |
| | INS | 4 | | | LR | A,I | |
| | INS | 4 | | | SR | 4 | |
| | CLR | | | | LR | 3,A | |
| | OUTS | 0 | | | PI | DSUP | |
| | POP | | PI DCLRAL | | LI | H'40' | |
| PRCCOF | PI | PRBK | | | LR | 1,A | |
| | PI | PRBK | | | LR | A,S | |
| | PI | PRGR | | | | | |

| Label | Mnemonic | Operand | Comment |
|---|---|---|---|
| | LR | S,A | |
| | PI | DSUP | |
| | PK | | |
| DSUP | LR | A,3 | |
| | NI | H'F' | |
| | AS | 1 | |
| | OUTS | 1 | |
| | JMP | NABL | |
| LIMCK | LR | K,P | limit check; |
| | PI | SAVKQ | # in B6 compare |
| | LISU | 7 | to limits DC; |
| | PI | LDOP | 0,0,1, error # |
| | XI | H'10' | in R7 |
| | LR | S,A | |
| | PI | ADD | |
| | LISU | 7 | |
| | LISL | 7 | |
| | LR | A,S | |
| | SR | 4 | |
| | BNZ | ULOK | |
| LIMER | LR | A,7 | |
| | LR | 0,A | |
| | JMP | ERROR | |
| ULOK | PI | LDOP | |
| | XI | H'10' | |
| | LR | S,A | |
| | PI | ADD | |
| | LISU | 7 | |
| | LISL | 7 | |
| | LR | A,S | |
| | SR | 4 | |
| | BNZ | LIMER | |
| | LR | P0,Q | |
| SAVKQ | LR | A,KU | |
| | LR | QU,A | |
| | LR | A,KL | |
| | LR | QL,A | |
| | POP | | |
| DUMP | LR | A,8 | |
| | NI | H'22' | |
| | OI | H'40' | dump cell & |
| | LR | 8,A | restart EC |
| | PI | ECLR | |
| | PI | DCLRAL | |
| | IN | H'21' | |
| | NI | H'18' | |
| | CI | H'10' | |
| | BC | STDP | |
| | PI | SMON | |
| | LR | 5,A | |
| | LR | 6,A | |
| DMLP | IN | H'21' | |
| | NI | H'10' | |
| | BNZ | STOF | |
| | INS | 4 | |
| | DS | 5 | |
| | BNZ | DMLP | |
| | DS | 6 | |
| | BNZ | DMLP | |
| DERR | PI | SMOF | |
| | LIS | 6 | |
| | LR | 0,A | |
| | JMP | ERROR | |
| STOF | PI | SMOF | |
| STDP | LI | H'7E' | |

| Label | Mnemonic | Operand | Comment |
|---|---|---|---|
| | OUTS | 1 | |
| | PI | NABL | |
| | PI | SMTM | |
| | IN | H'21' | |
| | NI | H'20' | |
| | BNZ | DMRR | |
| | LR | 0,A | |
| | LR | 5,A | |
| | LR | 6,A | |
| | LIS | 2 | |
| | LR | 1,A | |
| DPLP | IN | H'21' | |
| | NI | H'20' | |
| | BNZ | DPOF | |
| | IN | H'20' | |
| | CI | H'48' | |
| | BNZ | DPLL | |
| | LIS | 1 | |
| | LR | 0,A | |
| DPLL | DS | 5 | |
| | BNZ | DPLP | |
| | DS | 6 | |
| | BNZ | DPLP | |
| | DS | 1 | |
| | BNZ | DPLP | |
| DMRR | LI | H'76' | |
| | OUTS | 1 | |
| | PI | NABL | |
| | BR | DERR | |
| DPOF | LI | H'76' | |
| | OUTS | 1 | |
| | PI | NABL | |
| | CLR | | |
| | AS | 0 | |
| | BNZ | CLEN | |
| | JMP | STKH | |
| CLEN | PI | DLAY | |
| | PI | SMON | |
| DRCK | IN | H'21' | cell clean |
| | SL | 4 | mode |
| | BM | OPEN | |
| | DS | 0 | |
| | BNZ | DRCK | |
| | DS | 1 | |
| | BNZ | DRCK | |
| | BR | DERR | |
| OPEN | PI | SMOF | |
| | CLR | | |
| | LR | 0,A | |
| ERROR | PI | LERLT | error; display |
| | LISU | 4 | and wait for |
| | LISL | 0 | dump |
| | LI | H'FF' | |
| | LR | I,A | |
| | LR | S,A | |
| | PI | CCOF | |
| | PI | DSWT | |
| ERWAIT | IN | H'21' | |
| | NI | 1 | |
| | BC | ERWAIT | |
| | JMP | DUMP | |
| DGIN | IN | H'24' | read I/O |
| | NI | H'10' | counter to |
| | OUT | H'24' | @ISAR |
| | LI | H'30' | |

| Label | Mnemonic | Operand | Comment |
|---|---|---|---|
|  | OUT | H'25' |  |
|  | LIS | 2 |  |
|  | LR | 4,A |  |
| DGLD | IN | H'25' |  |
|  | SL | 4 |  |
|  | LR | S,A |  |
|  | LI | H'70' |  |
|  | OUT | H'25' |  |
|  | LI | H'30' |  |
|  | OUT | H'25' |  |
|  | IN | H'25' |  |
|  | IN | H'25' |  |
|  | NI | H'F' |  |
|  | AS | S |  |
|  | LR | D,A |  |
|  | LI | H'70' |  |
|  | OUT | H'25' |  |
|  | LI | H'30' |  |
|  | OUT | H'25' |  |
|  | DS | 4 |  |
|  | BNZ | DGLD |  |
|  | IN | H'25' |  |
|  | SL | 4 |  |
|  | LR | S,A |  |
|  | POP |  |  |
| CCOF | LISU | 4 |  |
|  | LISL | 2 |  |
|  | LR | A,S | # in R∅→5th display digit |
|  | NI | H'F0' |  |
|  | XS | 0 |  |
|  | LR | S,A |  |
|  | POP |  |  |
| BCLR | LR | K,P |  |
|  | PI | LATCL |  |
|  | LR | A,S | clear lights, relight those that should be on according to R8 |
|  | SL | 1 |  |
|  | BP | RDLP |  |
|  | LI | H'78' |  |
|  | OUTS | 1 |  |
|  | PI | NABL |  |
| RDLP | LR | A,8 |  |
|  | SL | 4 |  |
|  | BP | ERLP |  |
|  | LI | H'6A' |  |
|  | OUTS | 1 |  |
|  | PI | NABL |  |
| ERLP | LR | A,8 |  |
|  | NI | H'20' |  |
|  | BNZ | DTLP |  |
|  | LISU | 4 |  |
|  | LISL | 2 |  |
|  | LR | A,S |  |
|  | SR | 4 |  |
|  | AI | H'FF' |  |
|  | OI | H'58' |  |
|  | OUTS | 1 |  |
|  | BR | KKLP |  |
| DTLP | LI | H'6E' |  |
|  | OUTS | 1 |  |
| KKLP | PI | NABL |  |
|  | LIS | 4 |  |
|  | NS | 8 |  |
|  | BC | SLTKL |  |
|  | LI | H'68' |  |

| Label | Mnemonic | Operand | Comment |
|---|---|---|---|
|  | OUTS | 1 |  |
|  | PI | NABL |  |
| SLTKL | LI | H'10' |  |
|  | NS | 8 |  |
|  | BZ | SLTEL |  |
|  | LI | H'69' |  |
|  | OUTS | 1 |  |
|  | PI | NABL |  |
| SLTEL | PK |  |  |
| CKSUM | LR | K,P |  |
|  | LIS | 7 |  |
|  | LR | 0,A |  |
|  | LI | H'45' |  |
|  | LR | 2,A |  |
| CHK1 | PI | CCPT |  |
|  | LR | A,0 |  |
|  | SL | 1 |  |
|  | SL | 1 | compute checksum on K's return "zero" if ok |
|  | AS | 6 |  |
|  | LR | 6,A |  |
|  | PI | ERDR |  |
|  | LISU | 4 |  |
|  | LISL | 0 |  |
|  | LR | A,2 |  |
|  | AI | H'66' |  |
|  | ASD | I |  |
|  | AI | H'66' |  |
|  | ASD | S |  |
|  | LR | 2,A |  |
|  | DS | 0 |  |
|  | BC | CHK1 |  |
|  | CLR |  |  |
|  | AS | 2 |  |
|  | PK |  |  |
| CCPT | LISU | 4 | R6 pts to K1 of selected grain |
|  | LISL | 2 |  |
|  | LR | A,S |  |
|  | SR | 4 |  |
|  | AI | H'FF' |  |
|  | SL | 4 |  |
|  | SL | 1 |  |
|  | LR | 6,A |  |
|  | POP |  |  |
| LODK | LR | K,P |  |
|  | LISL | 4 | load K from earom; |
|  | CLR |  |  |
|  | LR | I,A |  |
|  | LR | I,A |  |
|  | PI | ERDI |  |
|  | LISL | 7 |  |
|  | LI | H'10' |  |
|  | NS | S |  |
|  | LR | 0,A |  |
|  | LR | A,S |  |
|  | SR | 4 |  |
|  | SR | 1 |  |
|  | XS | 0 |  |
|  | LR | 0,A |  |
|  | PI | RSH |  |
|  | LR | A,0 |  |
|  | LR | S,A |  |
|  | PK |  |  |
| LDOP | LISL | 4 |  |
| LDO1 | LM |  |  |

| Label | Mnemonic | Operand | Comment | Label | Mnemonic | Operand | Comment |
|---|---|---|---|---|---|---|---|
| | LR | I,A | | | DI | | |
| | BR7 | L101 | | | JMP | PRRET | |
| | LM | | | JTPRT | JMP | PRL1 | |
| | LR | S,A | | PRMS | LM | | |
| | POP | | | | LR | 0,A | |
| ALOFF | LR | K,P | | | LM | | load message |
| | DCI | ALOFTB | | | LR | 4,A | to print buffer, |
| | LIS | 6 | | PRMQ | LR | A,4 | format@ DC: |
| | LR | 0,A | Kill top lights; | | LR | IS,A | #chars/buffer |
| ALOFLP | LM | | (K,△, %, °C, KG, | | LM | | location/ |
| | OUTS | 1 | d.p.) | | LR | S,A | ⟨message⟩ |
| | PI | NABL | | | DS | 4 | |
| | DS | 0 | | | DS | 0 | |
| | BNZ | ALOFLP | | | BNZ | PRMQ | |
| | PK | | | | POP | | |
| PRLN | LR | K,P | | PRAST | LI | H'2A' | |
| PRLK | CLR | | print from | | LR | 0,A | '*' |
| | LR | 0,A | print buffer | | JMP | PRRO | |
| | LR | 1,A | | PRSL | LI | H'2F' | |
| PRLX | PI | PRST | | | LR | 0,A | '/' |
| | BZ | PRLG | | | JMP | PRRO | |
| | BP | PRRT | | PRNUM | LR | K,P | load # to print |
| | DS | 0 | | | LM | | buffer from |
| | BNZ | PRLX | | | LR | 2,A | scratchpad, |
| | DS | 1 | | | LM | | format@ DC: |
| | BNZ | PRLX | | | LR | 3,A | # digits before |
| PRRT | PK | | | | LM | | D.P./#afterD.P/ |
| PRLG | CLR | | | | LR | 1,A | # LZB/ISAR/$R_4$ |
| | OUT | H'26' | | | LM | | |
| | LI | O'67' | | | LR | IS,A | |
| | LR | 5,A | | | LM | | |
| | LIS | 1 | | | LR | 4,A | |
| | OUTS | H'E' | | | CLR | | |
| | LI | H'20' | | | LR | 6,A | |
| | OUTS | 0 | | PRNU1 | CLR | | |
| PRL1 | EI | | | | AS | 6 | |
| | CLR | | | | BNZ | PRLOD | |
| | LR | 0,A | | | LR | A,S | |
| | LR | 1,A | | | SR | 4 | |
| PRL2 | DS | 0 | | | BR | PRBOD | |
| | BNZ | PRL2 | | PRLOD | LIS | H'F' | |
| | DS | 1 | | | NS | D | |
| | BNZ | PRL2 | | PRBOD | LR | 0,A | |
| | DI | | | | LIS | 1 | |
| PRRET | CLR | | | | XS | 6 | |
| | OUTS | H'E' | | | LR | 6,A | |
| | OUTS | 0 | | | LR | A,IS | |
| | LIS | 3 | | | LR | S,A | |
| | OUT | H'26' | | | CLR | | |
| | PK | | | | AS | 1 | |
| PRLI | LR | A,S | | | BZ | PRNOBK | |
| | CI | O'47' | | | CLR | | |
| | LR | IS,A | | | AS | 0 | |
| | LR | A,S | | | BNZ | PRSTBK | |
| | BNZ | DWOBY | | | DS | 1 | |
| | LI | H'20' | | | LI | H'20' | |
| DWOBY | OUTS | 1 | | | LR | 0,A | |
| | LI | H'20' | | | PI | PRRO | |
| | OUTS | 0 | | | BR | PRWSB | |
| | LI | H'20' | | PRSTBK | CLR | | |
| | OUTS | 0 | | | LR | 1,A | |
| | DS | 5 | | PRNOBK | PI | PRNM | |
| | LR | A,S | | PRWSB | LR | A,S | |
| | CI | O'46' | | | | | |

| Label | Mnemonic | Operand | Comment |
|---|---|---|---|
| | LR | 13A | |
| | DS | 2 | |
| | BNZ | PRNU1 | |
| | CLR | | |
| | AS | 3 | |
| | BZ | PRNDN | |
| | LR | A,IS | |
| | LR | 5,A | |
| | PI | PRDP | |
| | LR | A,5 | |
| | LR | IS,A | |
| | LR | A,3 | |
| | LR | 2,A | |
| | CLR | | |
| | LR | 3,A | |
| | BR | PRNU1 | |
| PRNDN | PK | | |
| INVB6 | LR | K,P | |
| | LISU | 6 | |
| | LISL | 6 | $\frac{1}{B6} \Rightarrow B5$ |
| | LR | A,I | |
| | SR | 4 | |
| | BNZ | NTDBZ | |
| | LIS | 8 | |
| | LR | 0,A | |
| | JMP | ERROR | |
| NTDBZ | LR | A,KU | |
| | LR | 6,A | |
| | LR | A,KL | |
| | LR | 7,A | |
| | CLR | | |
| | LR | S,A | |
| | LISU | 5 | |
| | LR | S,A | |
| | LISU | 1 | |
| | LISL | 4 | |
| | CLR | | |
| INV1 | LR | I,A | |
| | BR7 | INV1 | |
| | LR | 1,A | |
| | LIS | 5 | |
| | LR | 0,A | |
| INV2 | CLR | | |
| | LR | 2,A | |
| | LISL | 4 | |
| INV3 | LISU | 1 | |
| | LR | A,S | |
| | LISU | 5 | |
| | LR | I,A | |
| | BR7 | INV3 | |
| INV4 | LISL | 4 | |
| | COM | | |
| INV5 | LISU | 6 | |
| | LI | H'66' | |
| | AS | S | |
| | LISU | 5 | |
| | ASD | S | |
| | LR | I,A | |
| | LR | A,S | |
| | LNK | | |
| | LR | S,A | |
| | BR7 | INV5 | |
| | CLR | | |
| | LR | S,A | |
| | BNZ | INV7 | |

| Label | Mnemonic | Operand | Comment |
|---|---|---|---|
| | LISL | 4 | |
| INV8 | LISU | 5 | |
| | LR | A,S | |
| | LISU | 1 | |
| | LR | I,A | |
| | BR7 | INV8 | |
| | LIS | 1 | |
| | AS | 2 | |
| | LR | 2,A | |
| | BR | INV4 | |
| INV7 | LR | A,0 | |
| | SR | 1 | |
| | AI | 0'60' | |
| | LR | IS,A | |
| | LR | A,1 | |
| | COM | | |
| | LR | 1,A | |
| | LR | A,2 | |
| | BZ | INV9 | |
| | SL | 4 | |
| | LR | S,A | |
| | BR | INW1 | |
| INV9 | XS | S | |
| | LR | S,A | |
| INW1 | LISU | 6 | |
| | PI | RSH | |
| | DS | 0 | |
| | BC | INV2 | |
| | LI | 0'62' | |
| | LR | 0,A | |
| | LI | 0'56' | |
| | LR | 1,A | |
| | PI | XFR3 | |
| | LISU | 5 | |
| | LISL | 7 | |
| | CLR | | |
| | LR | S,A | |
| | LR | A,6 | |
| | LR | KU,A | |
| | LR | A,7 | |
| | LR | KL,A | |
| | PK | | |
| BLOG | LR | K,P | |
| BLOGK | LIS | 5 | $\text{Log}_{nc}$ (43-45) $\Rightarrow$ B6 |
| | LR | 2,A | |
| | CLR | | |
| | LR | 3,A | |
| | LR | 0,A | |
| | LR | 1,A | |
| | LISU | 4 | |
| | LISL | 5 | |
| BCDC01 | PI | ROA1B2 | |
| | LR | A,0 | |
| | LR | 4,A | |
| | LR | A,1 | |
| | LR | 5,A | |
| | PI | ROA1B2 | |
| | PI | ROA1B2 | |
| | LR | A,5 | |
| | AS | 1 | |
| | LR | 1,A | |
| | LR | A,4 | |
| | LNK | | |
| | AS | 0 | |

| Label | Mnemonic | Operand | Comment |
|---|---|---|---|
| | CLR | | |
| | AS | 3 | |
| | BZ | BCDHID | |
| | LIS | H'F' | |
| | NS | D | |
| | BR | BCDBOD | |
| BCDHID | LR | A,S | |
| | SR | 4 | |
| BCDBOD | AS | 1 | |
| | LR | 1,A | |
| | LR | A,0 | |
| | LNK | | |
| | LR | 0,A | |
| | LIS | 1 | |
| | XS | 3 | |
| | LR | 3,A | |
| | DS | 2 | |
| | BNZ | BCDC01 | |
| LOG | CLR | | |
| | AS | 0 | |
| | BZ | RER | |
| | INC | | |
| | BZ | RER | |
| | BR | ROK | |
| RER | LIS | 8 | |
| | LR | 0,A | |
| | JMP | ERROR | |
| ROK | CLR | | |
| | LR | 5,A | |
| RESH | LR | A,5 | |
| | INC | | |
| | LR | 5,A | |
| | LR | A,1 | |
| | AS | 1 | |
| | LR | 1,A | |
| | LR | A,0 | |
| | LNK | | |
| | LR | J,W | |
| | AS | 0 | |
| | LR | 0,A | |
| | BC | FND | |
| | LR | W,J | |
| | BNC | RESH | |
| FND | LISU | 5 | |
| | LISL | 4 | |
| | CLR | | |
| | LR | I,A | |
| | LR | I,A | |
| | LR | A,5 | |
| | SL | 4 | |
| | LR | I,A | |
| | LIS | 1 | |
| | LR | S,A | |
| | LR | A,1 | |
| | LR | 3,A | |
| | LR | A,0 | |
| | LR | 2,A | |
| | LIS | 1 | |
| | LR | 6,A | |
| | PI | SHRZ | |
| | LI | H'80' | |
| | XS | 0 | |
| | LR | 0,A | |

| Label | Mnemonic | Operand | Comment |
|---|---|---|---|
| AGN | CLR | | |
| | AS | 2 | |
| | BNZ | XNE0 | |
| | AS | 3 | |
| | BZ | DONE | |
| XNE0 | LR | A,1 | |
| | COM | | |
| | INC | | |
| | LR | J,W | |
| | AS | 3 | |
| | LR | 5,A | |
| | BNC | NOC | |
| | LR | J,W | |
| NOC | LR | A,0 | |
| | COM | | |
| | LR | W,J | |
| | LNK | | |
| | LR | J,W | |
| | AS | 2 | |
| | LR | 4,A | |
| | BC | TGE1 | |
| | LR | W,J | |
| | BC | TGE1 | |
| | PI | SHRZ | |
| | LR | A,6 | |
| | INC | | |
| | LR | 6,A | |
| | BR | AGN | |
| TGE1 | LR | A,4 | |
| | LR | 0,A | |
| | LR | 2,A | |
| | LR | A,5 | |
| | LR | 1,A | |
| | LR | 3,A | |
| | PI | SHRZ | |
| | LI | H'80' | |
| | XS | 0 | |
| | LR | 0,A | |
| | LR | A,6 | |
| | LR | 5,A | |
| DZAG | DS | 5 | |
| | BZ | NOMS | |
| | PI | SHRZ | |
| | BR | DZAG | |
| NOMS | DCI | LOGTB | |
| | LR | A,6 | |
| | AI | H'FF' | |
| | LR | 5,A | |
| | AS | 5 | |
| | AS | 5 | |
| | ADC | | |
| | LISL | 4 | |
| LOOP | LM | | |
| | AI | H'66' | |
| | ASD | S | |
| | LR | I,A | |
| | LR | A,S | |
| | LNK | | |
| | LR | S,A | |
| | BR7 | LOOP | |
| | BR | AGN | |
| DONE | LISU | 6 | |
| | LISL | 4 | |
| | CLR | | |

| Label | Mnemonic | Operand | Comment |
|---|---|---|---|
|  | LR | 1,A |  |
|  | LI | H'50' |  |
|  | LR | I,A |  |
|  | LI | H'12' |  |
|  | LR | I,A |  |
|  | LIS | 3 |  |
|  | LR | S,A |  |
|  | LISU | 5 |  |
|  | LIS | 1 |  |
|  | LR | S,A |  |
|  | PI | NORM |  |
|  | JMP | MPZ |  |
| SHRZ | LR | A,1 |  |
|  | SR | 1 |  |
|  | LR | 1,A |  |
|  | LR | A,0 |  |
|  | SL | 4 |  |
|  | SL | 1 |  |
|  | SL | 1 |  |
|  | SL | 1 |  |
|  | XS | 1 |  |
|  | LR | 1,A |  |
|  | LR | A,0 |  |
|  | SR | 1 |  |
|  | LR | 0,A |  |
|  | POP |  |  |
| R0A1B2 | LR | A,0 |  |
|  | SL | 1 |  |
|  | LR | 0,A |  |
|  | LR | A,1 |  |
|  | AS | 1 |  |
|  | LR | 1,A |  |
|  | CLR |  |  |
|  | LNK |  |  |
|  | AS | 0 |  |
|  | LR | 0,A |  |
|  | POP |  |  |

\*
\*

\*
\*
\*
\*
\*            FILE 4--TABLES

| Label | Mnemonic | Operand | Comment |
|---|---|---|---|
| LOUL | DC | H'00005002' |  |
|  | DC | H'00002002' |  |
| HIUL | DC | H'00004003' |  |
|  | DC | H'00002003' |  |
| WTUL | DC | H'00100000' |  |
|  | DC | H'00100010' |  |
| TPUL | DC | H'00003502' |  |
|  | DC | H'00000502' |  |
| PERUL | DC | H'1015202530' |  |
|  | DC | H'3540455055' |  |
| PERLL | DC | H'0204060810' |  |
|  | DC | H'1214161820' |  |
| RMOIS | DC | H'180301' |  |
| RBULK | DC | H'110301' |  |
| RTEMP | DC | H'3A0400' |  |
| ELNM1 | DC | H'1037' |  |
|  | DC | C'  TRIPET' |  |
|  | DC | C'TE ET  ' |  |

| Label | Mnemonic | Operand | Comment |
|---|---|---|---|
| ELNM2 | DC | H'1037' |  |
|  | DC | C'   REN' |  |
|  | DC | C'AUD   ' |  |
| PMOIS | DC | H'0201011935' |  |
| PPER | DC | H'0130' |  |
|  | DC | C'%' |  |
| PBULK | DC | H'0201011235' |  |
| PKGHL | DC | H'0530' |  |
|  | DC | C'KG/HL' |  |
| PTEMP | DC | H'0400033B35' |  |
| PDEGC | DC | H'0630' |  |
|  | DC | C'GRADES' |  |
| PLIMEX | DC | H'1037' |  |
|  | DC | C'\*LIMITS ' |  |
|  | DC | C'EXCEEDED' |  |
| RCDAT1 | DC | H'190400' |  |
| RCDAT2 | DC | H'1C0400' |  |
| RCDAT3 | DC | H'110400' |  |
| RCDAT4 | DC | H'3A0400' |  |
| PCSAMM | DC | H'0C37' |  |
|  | DC | C'ECHANTIL' |  |
|  | DC | C'LON:' |  |
| PCANAM | DC | H'0837' |  |
|  | DC | C'ANALYSE:' |  |
| CD1LAB | DC | H'022F' |  |
|  | DC | C'D1' |  |
| CD2LAB | DC | H'022F' |  |
|  | DC | C'D2' |  |
| CD3LAB | DC | H'022F' |  |
|  | DC | C'D3' |  |
| CD4LAB | DC | H'022F' |  |
|  | DC | C'D4' |  |
| CD1NUM | DC | H'0400031A2C' |  |
| CD2NUM | DC | H'0400031D2C' |  |
| CD3NUM | DC | H'040003122C' |  |
| CD4NUM | DC | H'0400033B2C' |  |
| STATBL | DC | H'16060A1A1112' |  |
| TMPS | DC | H'00002504' |  |
| PDATE | DC | H'0437' |  |
|  | DC | C'DATE' |  |
| PMONTH | DC | H'0200013932' |  |
| PDAY | DC | H'020000382F' |  |
| PYEAR | DC | H'020000262C' |  |
| GRTBL | DC | C'    MA' |  |
|  | DC | C'IS    ' |  |
|  | DC | C'    SO' |  |
|  | DC | C'JA    ' |  |
|  | DC | C'  BLE T' |  |
|  | DC | C'ENDRE  ' |  |
|  | DC | C'   BLE ' |  |
|  | DC | C'DUR    ' |  |
|  | DC | C'     RI' |  |
|  | DC | C'Z     ' |  |
|  | DC | C'     OR' |  |
|  | DC | C'GE    ' |  |
|  | DC | C'    SEI' |  |
|  | DC | C'GLE    ' |  |
|  | DC | C'    COL' |  |
|  | DC | C'ZA    ' |  |
|  | DC | C'   TOURN' |  |
|  | DC | C'ESOL   ' |  |
|  | DC | C'    SOR' |  |
|  | DC | C'GHO    ' |  |
|  | DC | C'ESCOU' |  |
|  | DC | C'RGEON  ' |  |

| Label | Mnemonic | Operand | Comment | Label | Mnemonic | Operand Comment |
|---|---|---|---|---|---|---|
| | DC | C' AVO' | | * | | |
| | DC | C'INE ' | | * | DC | C"CONTROLE" |
| TABL | DC | H'8182848818484121' | | END | | |
| | DC | H'1142221244241428' | | * | | |
| RSTABL | DC | AL2(STKH) | | * | | |
| | DC | AL2(SRCK) | | * | | |
| | DC | AL2(SMRC) | | * | | |
| | DC | AL2(STMH) | | * | | |
| | DC | AL2(STWT) | | | | |
| PENTMO | DC | H'0437' | | | | |
| | DC | C'JOUR' | | | | |
| PENTDA | DC | H'0437' | | | | |
| | DC | C'MOIS' | | | | |
| PENTYR | DC | H'0537' | | | | |
| | DC | C'ANNEE' | | | | |
| LITTBL | DC | H'68696A6E6F786D6C' | | | | |
| | DC | H'6B7958595A5B5C5D' | | | | |
| | DC | H'5E5F' | | | | |
| PCC1 | DC | H'0237' | | | | |
| | DC | C'K1' | | | | |
| | DC | H'0237' | | | | |
| | DC | C'K2' | | | | |
| | DC | H'0237' | | | | |
| | DC | C'K3' | | | | |
| | DC | H'0237' | | | | |
| | DC | C'K4' | | | | |
| | DC | H'0237' | | | | |
| | DC | C'K5' | | | | |
| | DC | H'0237' | | | | |
| | DC | C'K6' | | | | |
| | DC | H'0237' | | | | |
| | DC | C'K7' | | | | |
| | DC | H'0237' | | | | |
| | DC | C'K8' | | | | |
| PCCOF | DC | H'0400002133' | | | | |
| INVCM | DC | H'0C37' | | | | |
| | DC | C'***ERROM' | | | | |
| | DC | C'E***' | | | | |
| ALOFTB | DC | H'606163656471' | | | | |
| LOGTB | DC | H'000090' | | | | |
| | DC | H'968495' | | | | |
| | DC | H'350798' | | | | |
| | DC | H'890699' | | | | |
| | DC | H'205499' | | | | |
| | DC | H'287799' | | | | |
| | DC | H'638899' | | | | |
| | DC | H'359499' | | | | |
| | DC | H'189799' | | | | |
| | DC | H'599899' | | | | |
| | DC | H'309999' | | | | |
| | DC | H'659999' | | | | |
| | DC | H'829999' | | | | |
| | DC | H'919999' | | | | |
| | DC | H'969999' | | | | |
| | DC | H'989999' | | | | |
| PCDM1 | DC | H'0934' | | | | |
| | DC | C'CAL. INF' | | | | |
| | DC | C'0' | | | | |
| PCDM2 | DC | H'0437' | | | | |
| | DC | C' ' | | | | |
| PRCSIM | DC | H'0934' | | | | |
| | DC | C'VALEUR D' | | | | |
| | DC | C'E' | | | | |
| PRCSIN | DC | H'0835' | | | | |

While a test instrument of the present invention has been shown and described herein a a moisture tester, it will be apparent that the embodiment disclosed is equally applicable to the measuring of the contents of constituents of materials other than moisture. Thus, the instrument disclosed herein is capable of performing measurements of a plurality of constituent contents of a material as well as being adapted to measure such constituent contents of a plurality of different materials.

While a particular embodiment of the present invention has been shown and described herein, various changes may occur to those skilled in the art and will be understood as forming part of this invention insofar as they fall within the spirit and scope of the appended claims.

The invention is claimed as follows:

1. An analysis instrument for measuring the contents of a sample of a material comprising: a test cell for receiving said sample, said test cell comprising a capacitor whose electrical properties are modified in accordance with the dielectric constant of the sample, which dielectric constant is a function of the contents thereof, circuit means including means for applying two electrical signals of different predetermined frequencies to said test cell, means for applying said two electrical signals to said test cell when said test cell is empty and for again applying said two electrical signals to said test cell when said sample is received therein, test circuit means including said capacitor for receiving said applied signals and for producing test signals in response to said applied electrical signals, said test signals corresponding to said dielectric constant of said material, said circuit means further including measurement circuits for receiving said test signals and providing an indication corresponding to said contents of said material in accordance with said test signals.

2. A moisture tester for measuring the moisture content of a sample of a bulk commodity comprising: a test cell for receiving said sample, said test cell comprising a capacitor whose electrical properties are modified in accordance with the dielectric constant of a sample which dielectric constant is proportional to the moisture content thereof, circuit means including means for applying two electrical signals of different predetermined frequencies to said test cell and means for applying said two electrical signals to said test cell when said test cell is empty and again applying said two electrical signals to said test cell when said sample is received therein, test circuit means including said capacitor for receiving applied signals and for producing test signals in response to said applied electrical signals corresponding to said dielectric constant of said sample, said circuit means further including a measurement circuit for receiving said test signals and for providing an indication corresponding to said moisture content in accordance with said test signals.

3. A moisture tester according to claim 2 further including means for producing a weight signal corresponding to the weight of said sample, said measurement circuit further including means for receiving said weight signal and producing a bulk density signal in response thereto corresponding to the bulk density of the sample, and for providing an indication of the bulk density of the sample in accordance with said bulk density signal.

4. A moisture tester according to claim 3 wherein said measurement circuit further includes means for modifying said moisture indication according to the variation of the bulk density of the sample from a predetermined reference bulk density in accordance with said bulk density signal.

5. A moisture tester according to claim 4 further including means for producing temperature signals corresponding to the temperature of said test cell when empty and when filled with said sample, said measurement circuit further including means for receiving said temperature signals and producing an indication of the temperature of the sample in accordance therewith.

6. A moisture tester according to claim 5 wherein said measurement circuit further includes means for modifying said moisture indication according to the variation of said sample temperature from a predetermined reference temperature in accordance with said temperature signals and with said moisture indication.

7. A moisture tester according to claim 6 further including a control panel accessible to an operator thereof and connected to said circuit means, and wherein said circuit means further include control circuit means for automatically controlling, in a sequence, said applications of said two electrical signals to said test cell, said receiving of said test signals, temperature signals and weight signal, said providing of said moisture, bulk density and temperature indications and said modifying of said moisture indication in accordance with predetermined instructions stored therein and with operator instructions from the control panel.

8. A moisture tester according to claim 7 further including a calibration network, selectively connectable to said test cell capacitor in response to operator instructions from the control panel, for checking the operation of the moisture tester.

9. A moisture tester according to claim 8 wherein said measurement and control circuits include microprocessor means for receiving said test signals and for applying a plurality of empirically determined constants to said test signals for calculating said moisture content of said sample and for providing said moisture indication in accordance with said calculated moisture content and for providing said automatic control.

10. A moisture tester according to claim 9 wherein said circuit means further includes display circuit means for providing a visual readout of said moisture content said bulk density and said temperature in accordance with said moisture, bulk density and temperature indications.

11. A moisture tester according to claim 10, wherein said measurement and control circuits further include a peak detector circuit for receiving said test signals and for providing a peak portion thereof to said microprocessor means.

12. A moisture tester according to claim 11 wherein said measurement and control circuits further include an input/output circuit connected to said peak detector circuit for receiving said peak portions of said test signals, said weight signal and said temperature signal and for selectively providing said peak portions and said weight and temperature signals to said microprocessor means.

13. A moisture tester according to claim 12 wherein said measurement and control circuits include nonvolatile memory circuits for storing said plurality of empirically determined constants.

14. A moisture tester according to claim 13 wherein said microprocessor means includes a central processing unit for receiving and storing said test signals, said weight signal and said temperature signal, for calculating said moisture content, for producing said moisture indication, for producing said bulk density signal, and for modifying said moisture indication according to said temperature signal and said bulk density signal, and for providing said automatic control.

15. A moisture tester according to claim 14 wherein said microprocessor means further includes a plurality of peripheral storage units connected to said central processing unit for storing said predetermined instructions and for receiving said operator instructions from said control panel and transmitting said operator instructions to said central processing unit.

16. A moisture tester according to claim 15 wherein selected ones of said plurality peripheral storage units further include input/output ports for connection, respectively, to said input/output circuits and to said memory circuits for receiving and transmitting to said central processing unit said peak portions of said test signals, said weight signals and said temperature signals and for selecting and transmitting to said central processing unit said empirically determined constants as called for thereby.

17. A moisture tester for measuring the moisture content of a sample of a bulk commodity comprising: a test cell for receiving said sample, said test cell comprising a capacitor, and circuit means connected to said capacitor for taking measurements across said capacitor and for providing an indication of said moisture content of said sample in accordance therewith, said circuit means including microprocessor means operating in a predetermined sequence in accordance with a set of predetermined instructions stored therein for taking said measurements and for providing output data corresponding to said moisture content in accordance with said measurements, and visual display means for receiving said output data and providing a visual display corresponding to said moisture content in accordance therewith.

18. A moisture tester according to claim 17 further including means for producing a weight signal corresponding to the weight said sample in said test cell.

19. A moisture tester according to claim 18 wherein said microprocessor means further includes means for receiving said weight signal and calculating therefrom the bulk density of the sample and producing data corresponding to the bulk density of the sample in response thereto.

20. A moisture tester according to claim 19 further including means for producing temperature signals corresponding to the temperature of said test cell when empty and when filled with said sample respectively.

21. A moisture tester according to claim 19 wherein said microprocessor means includes means for receiving said temperature signal and producing data corresponding to the temperature of said sample in accordance therewith.

22. A moisture tester according to claim 18 wherein said microprocessor means further includes means for modifying said data corresponding to said moisture content in accordance with said bulk density data and with said temperature data and the variations thereof from predetermined reference bulk density and temperature data stored therein.

23. A moisture tester according to claim 22 wherein said microprocessor means further includes means for controlling in a sequence, in accordance with said predetermined instructions stored therein, said taking of measurements across the test cell capacitor, said reception of said weight and temperature signals, and said production and modification of said data in response thereto.

24. A moisture tester according to claim 23 wherein said microprocessor means includes a central processing unit for receiving and storing said measurements taken across the test cell capacitor, for performing calculations thereon including the application thereto of data corresponding to a plurality of empirically determined constants to produce said data corresponding to said moisture content, for receiving and storing said weight signal and performing calculations thereon including the application thereto of constant volume data for producing said bulk density data, for receiving and storing said temperature signal and producing said temperature data therefrom, and for modifying said moisture content data in accordance with the variations of said bulk density data and said temperature data from reference bulk density and reference temperature data.

25. A moisture tester according to claim 24 further including memory means connected to said microprocessor means for storing said data corresponding to a plurality of predetermined empirical constants, said reference bulk density and reference temperature data and said constant volume data.

26. A moisture tester according to claim 25 wherein said microprocessor means further includes a plurality of peripheral storage units connected between said central processing unit and said memory means for storing said set of predetermined instructions and for selectively transmitting said data from said memory means to said central processing unit as called for thereby.

27. A moisture tester according to claim 26 wherein said memory means comprises an electrically erasable programmable read only memory and said moisture tester includes means including a control panel accessible to an operator and including said microprocessor means for altering said data stored in said memory.

28. A moisture tester according to claim 27 further including ultra-violet erasable programmable read only memory means connected to said central processing unit for selectively storing predetermined instructions therefore to supplement said predetermined instructions stored in said peripheral storage units and for selectively storing predetermined instructions to alter said predetermined instructions stored in said peripheral storage units.

29. A moisture tester according to claim 28 further including means including a static memory interface connected between said central processing unit and said ultra-violet erasable programmable read only memory means for selecting and transmitting to said central processing unit said predetermined instructions therefrom as called for by said central processing unit.

30. A moisture tester according to claim 29 further including random access memory means connected to said static memory interface for selectively providing additional storage for said measurements taken across said test cell capacitor, said weight signal and said temperature signal.

31. A moisture tester according to claim 25 further including erasable programmable read only memory means connected to said central processing unit for storing said set of predetermined instructions therefore.

32. A moisture tester according to claim 31 wherein said microprocessor means further includes a plurality of peripheral input/output units connected between said central processing unit and said erasable and programmable read only memory means for transmitting said predetermined instructions therefrom to said central processing unit as called for thereby.

33. A tester for measuring a constituent content of a sample of bulk commodity comprising: a test cell for receiving a sample, means for producing a weight signal corresponding to the weight of said sample in said test cell, means for producing a temperature signal corresponding to the temperature of said sample in said test cell, and microprocessor means operating in a predetermined sequence in accordance with a set of predetermined instructions stored therein, for applying predetermined signals to said test cell and receiving test signals therefrom in response to said applied signals, for receiving said weight signal and said temperature signal and for providing output data corresponding to said constituent content of the sample in accordance with said test signals said weight signal and said temperature signal.

34. A tester according to claim 33 further including display means for receiving said output data and providing a visual display corresponding to said constituent content in accordance with said output data.

35. A tester according to claim 33 wherein said microprocessor means includes memory means for storing a plurality of predetermined constants and means for calculating the moisture content of said sample from said test signals, weight signal and temperature signal, and from said predetermined constants, according to said predetermined instructions including the formula:

$$MA = K1 + K2(X) + K3 \log(X + K4)$$

$$X = G2 + K5(G5/G2)$$

$$MDC = MA(DStd/DSA)$$

$$M2 = MDC + K6MCD(TS - TSTD),$$

wherein: MA is a first obtained moisture value, G2 and G5 are log functions of said test signals, K1 through K6 are empirically determined constants comprising a portion of said predetermined constants, MDC is moisture corrected for sample density, DSA is the density of the sample calculated by said microprocessor in accordance with said weight signal, DStd is a standard density comprising a portion of said predetermined constants, M2 is the moisture content of the sample corrected for density and temperature, TS is the temperature of said sample corresponding to said temperature signal, and TSTD is a standard temperatures comprising a portion of said predetermined constants.

* * * * *